United States Patent [19]
Ouchi

[11] Patent Number: 5,882,293
[45] Date of Patent: Mar. 16, 1999

[54] TREATMENT ACCESSORIES FOR ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 855,442

[22] Filed: May 13, 1997

[30] Foreign Application Priority Data

| Sep. 5, 1996 | [JP] | Japan | 8-234945 |
| Sep. 5, 1996 | [JP] | Japan | 8-234946 |
| Sep. 10, 1996 | [JP] | Japan | 8-239083 |
| Feb. 26, 1997 | [JP] | Japan | 9-041720 |
| Mar. 10, 1997 | [JP] | Japan | 9-054437 |
| Mar. 10, 1997 | [JP] | Japan | 9-054438 |
| Mar. 19, 1997 | [JP] | Japan | 9-066398 |
| Mar. 25, 1997 | [JP] | Japan | 9-071064 |
| Mar. 25, 1997 | [JP] | Japan | 9-071065 |

[51] Int. Cl.[6] ........................ A61B 1/00
[52] U.S. Cl. .................. 600/104; 606/205
[58] Field of Search ............. 600/104, 106, 600/107, 117; 606/205, 206, 207, 208, 209; 604/117, 239; 128/774

[56] References Cited

U.S. PATENT DOCUMENTS

| 4,211,214 | 7/1980 | Chikashige et al. . |
| 4,271,845 | 6/1981 | Chikashige et al. . |
| 4,385,631 | 5/1983 | Uthmann ........................ 604/284 |
| 4,645,491 | 2/1987 | Evans ........................ 604/117 X |
| 4,779,349 | 10/1988 | Odenstein et al. . |
| 4,982,727 | 1/1991 | Sato . |
| 5,084,022 | 1/1992 | Claude ........................ 604/117 X |
| 5,217,002 | 6/1993 | Katsurada et al. . |
| 5,217,024 | 6/1993 | Dorsey et al. . |
| 5,320,608 | 6/1994 | Gerrone ........................ 604/117 |
| 5,325,866 | 7/1994 | Krzyzanowski ........................ 606/205 X |
| 5,611,778 | 3/1997 | Brinon ........................ 604/117 |
| 5,693,030 | 12/1997 | Lee et al. ........................ 604/117 |

FOREIGN PATENT DOCUMENTS

| 52-158589 | 5/1977 | Japan . |
| 61-203009 | 12/1986 | Japan . |
| 9724988 | 7/1997 | WIPO . |

OTHER PUBLICATIONS

"Gastrointestinal Endoscopy", Martin B. Grossman, M.D., Clinical Symposia, vol. 32, No. 3, CIBA Pharmaceutical Company, Summit, New Jersey, 1980.

*Primary Examiner*—Beverly M. Flanagan
*Attorney, Agent, or Firm*—Greenblum & Bernstein, P.L.C.

[57] ABSTRACT

The treatment accessory for an endoscope is inserted in or removed from a forceps channel of the endoscope through an inlet of the forceps channel. The treatment accessory includes a treatment device and a flexible shaft. The treatment device is provided at a first end of the flexible shaft. The flexible shaft is provided with a marking at a predetermined portion thereof. The treatment device is located at a predetermined position inside the forceps channel when a predetermined portion of the marking is located at the inlet of the forceps channel.

37 Claims, 65 Drawing Sheets

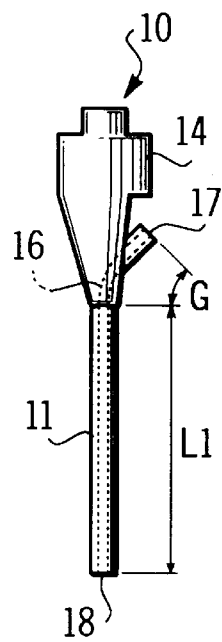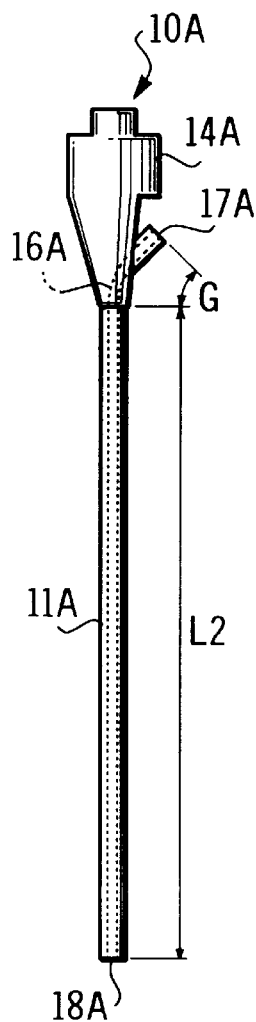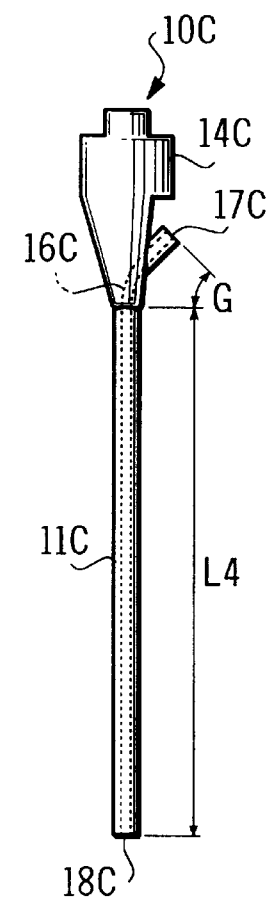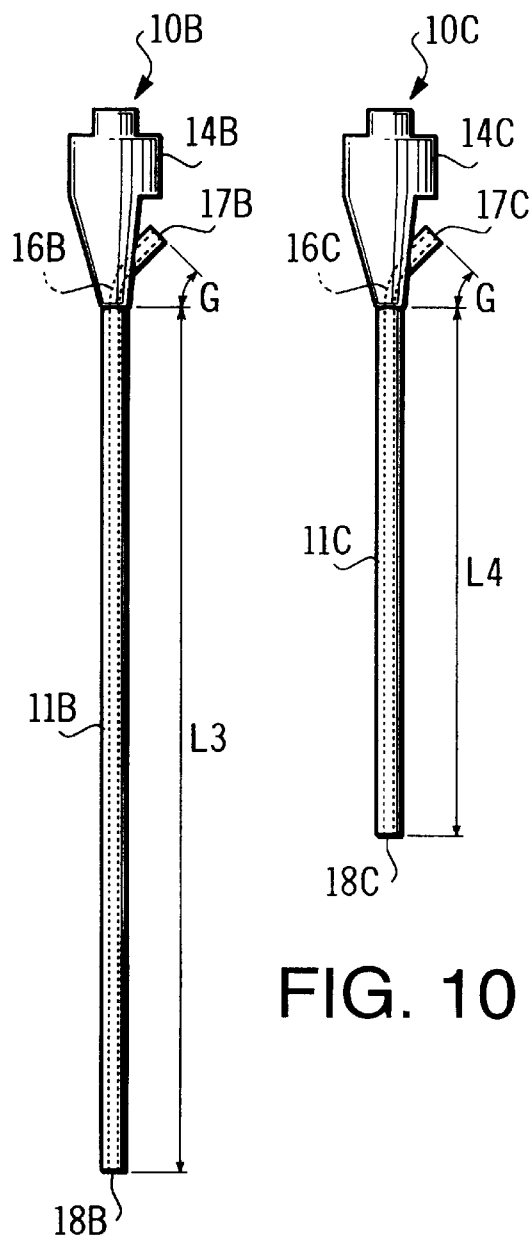
FIG. 7
FIG. 8
FIG. 9
FIG. 10

TREATMENT ACCESSORIES FOR ENDOSCOPE

BACKGROUND OF THE INVENTION

The present invention relates to treatment accessories for an endoscope. During use, a treatment accessory is inserted in a forceps channel of the endoscope; however, as the treatment accessory is being inserted through the forceps channel of the endoscope, before the distal end of the treatment accessory appears in an observing field of the endoscope, the distal end will have already been extended from the end of the forceps channel by a certain amount. Since a treatment device such as a forceps device is connected to the distal end of the treatment accessory, if the treatment accessory is pushed and extended from the forceps channel excessively, the treatment accessory may damage a mucous layer inside a human cavity.

In a conventional treatment accessory, the above problem is prevented, by providing an index mark on a manipulation portion of the treatment accessory such that the extending amount of the treatment accessory is recognized. An example of such a treatment accessory is disclosed in JP Utility Model Provisional Publication SHO 52-158589, and JP Utility Model Provisional Publication SHO 61-203009.

However, since the viscera (human tissue) or the like are continuously moving, once the affected part comes into the observing field, it is preferable that the treatment accessory be pushed quickly through the forceps channel.

In this case, even though an index mark is formed on the treatment accessory, in a quick insertion, the treatment accessory may be inserted more than intended and the viscera (human tissue) may be damaged.

Further, since there are various endoscopes having different lengths of forceps channels, the treatment accessory is generally formed to have a length that is appropriate for use in an endoscope having a forceps channel of a particular length. Accordingly, a plurality of treatment accessories which have different lengths must be available.

However, having a plurality of treatment accessories for endoscopes having different forceps channel lengths is not economical. A long treatment accessory may also be used for an endoscope having a shorter forceps channel, however, if the treatment accessory is relatively long with respect to the forceps channel, there is a risk that when the treatment accessory is inserted in the forceps channel, the treatment accessory may be inserted too far and may damage tissue inside a body.

Further to the above, the treatment accessory should be removed from the forceps channel as soon as the affected part has been treated. However, while the treatment accessory is being removed (pulled out of the forceps channel), it is difficult to judge the length of the treatment accessory, such that, if the treatment device is removed quickly, the flexible shaft may jump on exiting the forceps channel such that a collected sample or other substance may be dislodged and sprinkled around the room.

SUMMARY OF THE INVENTION

It is therefore an object of the present invention to provide an improved treatment accessory can be inserted in the forceps channel quickly without damaging the tissue in the human cavity.

A further object of the invention is to provide an improved treatment accessory which can be used in various endoscopes having forceps channels of different lengths while also allowing a quick insertion of the treatment accessory into the forceps channel of the endoscope.

Yet a further object of the invention is to provide an improved treatment accessory which may be removed from a forceps channel quickly without risk of dislodging a collected sample or spraying tissue or the like around the removal area.

For the above objects, according to the invention, there is provided a treatment accessory for an endoscope, the treatment accessory being inserted in or removed from a forceps channel of the endoscope through an inlet of the forceps channel. The treatment accessory includes a treatment device, a flexible shaft, the treatment device being provided at a first end of the flexible shaft. The flexible shaft is provided with a marking at a predetermined portion thereof, and the treatment device is located at a predetermined position inside the forceps channel when a predetermined portion of the marking is located at the inlet of the forceps channel.

Optionally, it may be arranged such that when the treatment device is located at a position within a predetermined position range inside the forceps channel, the marking is located at the inlet.

Further, the marking may have a predetermined length along an axis of the flexible shaft, and in such a case, when any portion of the marking is located at the inlet, the treatment device is located inside the forceps channel.

Alternatively, the marking may have a predetermined length along an axis of the flexible shaft, and it could be arranged such that the predetermined portion is an end of the marking.

In a further alternative arrangement, the marking has a predetermined length along an axis of the flexible shaft, and when one end of the marking is located at the inlet, the treatment device is located inside the forceps channel, and when the other end of the marking is located at the inlet, the treatment device is extended from the outlet of the forceps channel.

Still optionally, at least one of a color, texture, thickness, and shape of the marking may be different from the other portion of the flexible shaft.

Furthermore, the flexible shaft is provided with at least one other marking, the at least one other marking corresponding to at least one other forceps channel having a length different from the forceps channel.

Yet optionally, the marking may be a ring-like member slidably fitted on the flexible shaft, a predetermined frictional force being generated between the ring-like member and the flexible shaft when the ring-like member is slid on the flexible shaft.

In this case, at least a part of an outer diameter of the ring-like member could be greater than an inner diameter of the forceps channel.

Alternatively, an outer diameter of the ring-like member could be made smaller than an inner diameter of the forceps channel.

Further, the flexible shaft may be provided with at least one position indicating area, which indicates an initial position of the ring-like member.

Further optionally, at least one of a color, thickness, texture, and a shape of the position indicating area may be different from the other portion of the flexible shaft.

Further, the flexible shaft may be provided with a plurality of position indicating areas corresponding to a plurality of forceps channels having different lengths.

In this case, the plurality of position indicating areas could be made different from each other by at least one of a color, texture, thickness, and a shape.

Still optionally, the flexible shaft may be a coil shaft formed from wound coils, and the marking may be formed by a tube member covering the coil shaft. It should be noted that the tube member is made from resin.

According to another aspect of the invention, there is provided a treatment accessory for an endoscope, the treatment accessory being inserted in a forceps channel of the endoscope, the treatment accessory having a shaft and a treatment device provided at a distal end of the shaft, the treatment device being extend from a distal end of the forceps channel when treatment is performed, the shaft being provided with a marking, the marking being located at an inlet of the forceps channel when the treatment device is located at a position close to the distal end of the forceps channel and inside the forceps channel.

Optionally, the shaft may be provided with another marking which is located at the inlet of the forceps channel when the treatment device is located at the distal end of the forceps channel.

Further optionally, the marking comprises a visually recognizable portion. Alternatively, the marking may include a portion recognizable by of a sense of touch.

According to further aspect of the invention, there is provided a treatment accessory for endoscopes, the treatment accessory being inserted in one of a plurality of forceps channels of the endoscopes. The treatment accessory has a shaft, and a treatment device provided at a distal end of the shaft, the treatment device being extended from a distal end of each of the plurality of forceps channels when treatment is performed. The shaft is provided with a plurality of markings, each of the plurality of markings being located at an inlet of a respective one of the plurality of forceps channels when the treatment device is located at a position close to the distal end of the respective one of the forceps channels and inside therein.

Optionally, the plurality of markings may have visually recognizable portions.

Further optionally, the plurality of markings may have different characteristics from each other.

According to a further aspect of the invention, there is provided a treatment accessory having a shaft which is to be inserted in and removed from a forceps channel of an endoscope. A treatment device is provided at a distal end of the shaft, the shaft being provided with a marking, the marking appearing from the forceps channel when the shaft is being withdrawn from the forceps channel when a length of the treatment accessory remaining in the forceps channel is a predetermined length. The predetermined length may be within a range of 10 cm through 30 cm.

Optionally, the marking may be located inside the forceps channel when the treatment device is extended from the forceps channel and used for treating.

Further, the marking has a color different from a color of the other portion of the shaft.

Furthermore, the marking may have a hardness different from the hardness of the other portion of the shaft.

Still further optionally, the marking may include a portion which has an outer diameter different from that of the other portion of the shaft.

According to another aspect of the invention, there is provided a treatment accessory for an endoscope, the treatment accessory being provided with a shaft to be inserted in or withdrawn from a forceps channel of the endoscope. The shaft is provided with a slidable member fitted thereon, and the slidable member, when being contacted with an inlet of the forceps channel, applies a predetermined resistance to the shaft when the shaft is being inserted in the forceps channel.

Optionally, the slidable member is slidable on the shaft along an axial direction of the shaft, a predetermined friction existing between the slidable member and the shaft, the predetermined friction causes the predetermined resistance to the shaft.

Alternatively, the slidable member may be formed from elastic material, the inner diameter of the slidable member being smaller than an outer diameter of the shaft.

Furthermore, the shaft may be provided with a marking which indicates a position where the slidable member is to be initially located.

Further alternatively, the slidable member may be formed to have a cylindrical shape.

Optionally, the slidable member is further provided with a flange portion which has a greater diameter than the inner diameter of the inlet of the forceps channel.

Further optionally, the slidable member may be formed to have substantially a cylindrical shape, a diameter of an end portion of the cylindrical shape being smaller than a diameter of a central portion of the cylindrical shape.

According to a still further aspect of the invention, there is provided a treatment accessory for an endoscope, the treatment accessory being provided with a shaft to be inserted in or withdrawn from a forceps channel of the endoscope. The shaft is provided with a fitted member fitted thereon at a predetermined portion, the fitted member causes a predetermined resistance when the fitted member passes through a slit of a forceps tap.

Optionally, the treatment device further comprises at least one other fitted member.

Further, the fitted member and at-least-one other fitted member is visually distinguishable.

BRIEF DESCRIPTION OF THE DRAWINGS

FIGS. 7 to 10 show various endoscopes having various lengths;

DETAILED DESCRIPTION OF THE PREFERRED EMBODIMENTS

Figure 3:
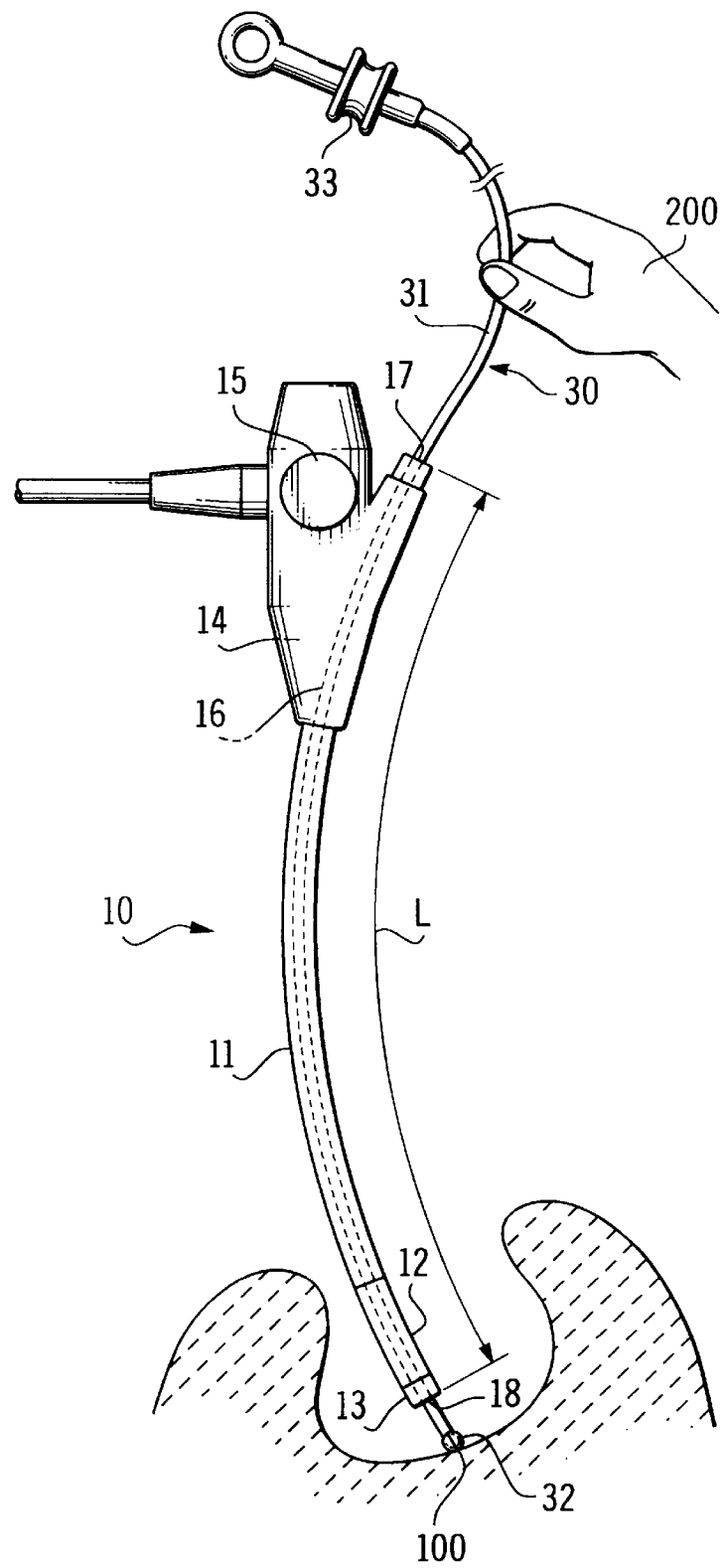
FIG. 3 shows the treatment accessory of FIG. 1 when inserted in a forceps channel of an endoscope and operated by an assistant.

FIG. 3 shows a treatment accessory 30 according to a first embodiment of the invention, when inserted in a forceps channel 16 of an endoscope 10.

The endoscope 10 includes an insertion section 11 which, in use, is inserted in a body cavity. The insertion section 11 is formed as a flexible tube and the proximal end of the insertion section 11 is connected to a manipulation unit 14. The distal end of the insertion section 11 is provided with a bendable portion 12. The bendable portion 12 can be bent by operation of an manipulation knob 15 provided at the manipulation unit 14. At the tip of the bendable portion 12, an end unit 13 accommodating an objective optical system (not shown) is connected.

The forceps channel 16 is formed to extend from an inlet 17 formed on the manipulation unit 14, through the whole length of the insertion section 11, to an outlet 18 formed in the end unit 13. In the description hereinafter, the length of the forceps channel 16, i.e., the distance between the inlet 17 and the outlet 18 is indicated as an FC length L.

The treatment accessory 30 includes a shaft 31, a treatment device 32 that may be movable, and an operating unit 33. The shaft 31 may be, for example, a coil pipe made of closely-wound thin stainless steel wire, or a tube made of a synthetic resin such as tetrafluoraethylene resin. The treatment device 32 is provided at the distal end of the shaft 31 for treating an affected part 100. The treatment device 32 is small enough to pass through the forceps channel 16. The operating unit 33 is provided at the proximal end of the shaft 31 for remotely operating the movable treatment device 32.

Figure 4:
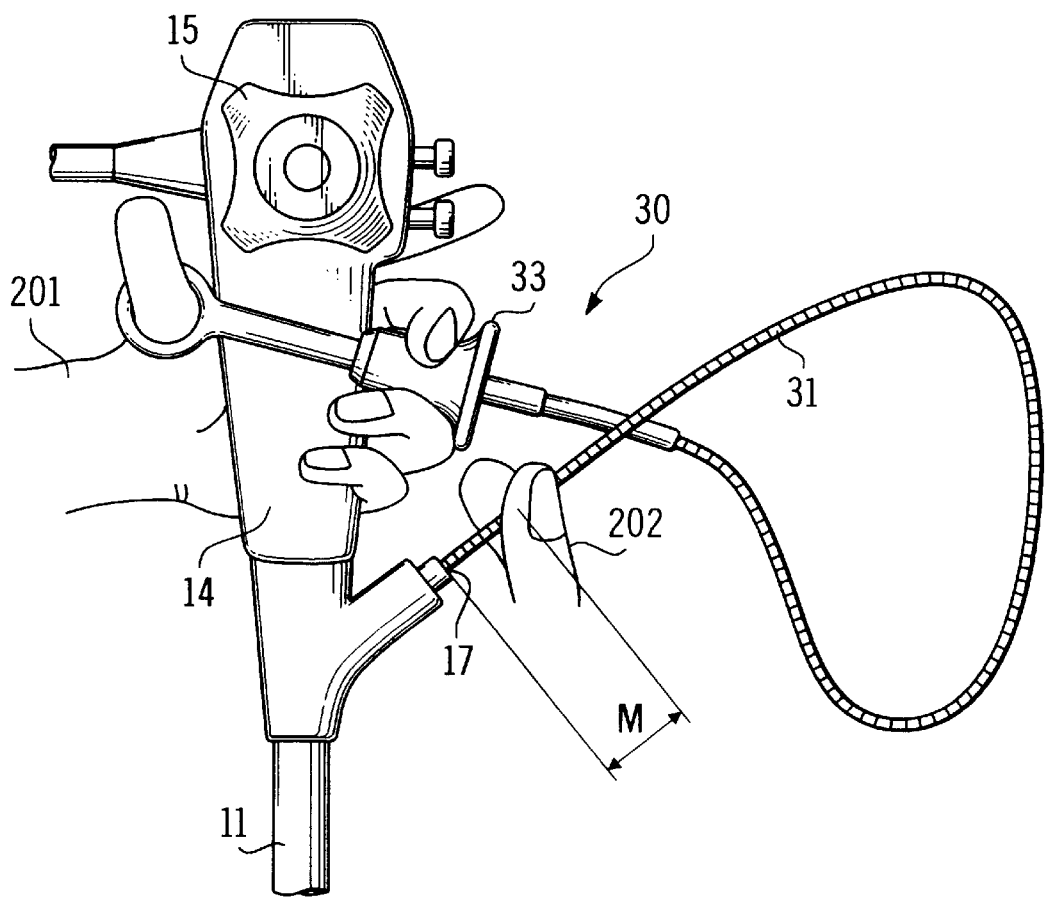
FIG. 4 shows the treatment accessory of FIG. 1 when inserted in a forceps channel of an endoscope and operated by an operator of the endoscope.

In FIG. 3, the endoscope 10 is operated by an operator, and the treatment accessory 30 is operated by an assistant using, for example, a right hand 200. In FIG. 4, both the endoscope 10 and the treatment accessory 30 are operated by a single operator using, for example, a left hand 201 and a right hand 202.

As shown in FIG. 4, the operator operates both the manipulation unit 14 of the endoscope 10 and the operating unit 33 of the treatment accessory 30 with the left hand 201. With the right hand 202, the operator inserts or retracts the shaft 31 of the treatment accessory 30 in the forceps channel 16. A pinch position at which the shaft 31 is pinched by the operator may be different depending on the preciseness of the movement of the treatment accessory 30 required, for example, the pinch position may be a pinch distance M of 10 cm away from the inlet 17 for a general case, or, if a more subtle movement is required, the pinch position may be a pinch distance M of 1 cm.

Figure 2:
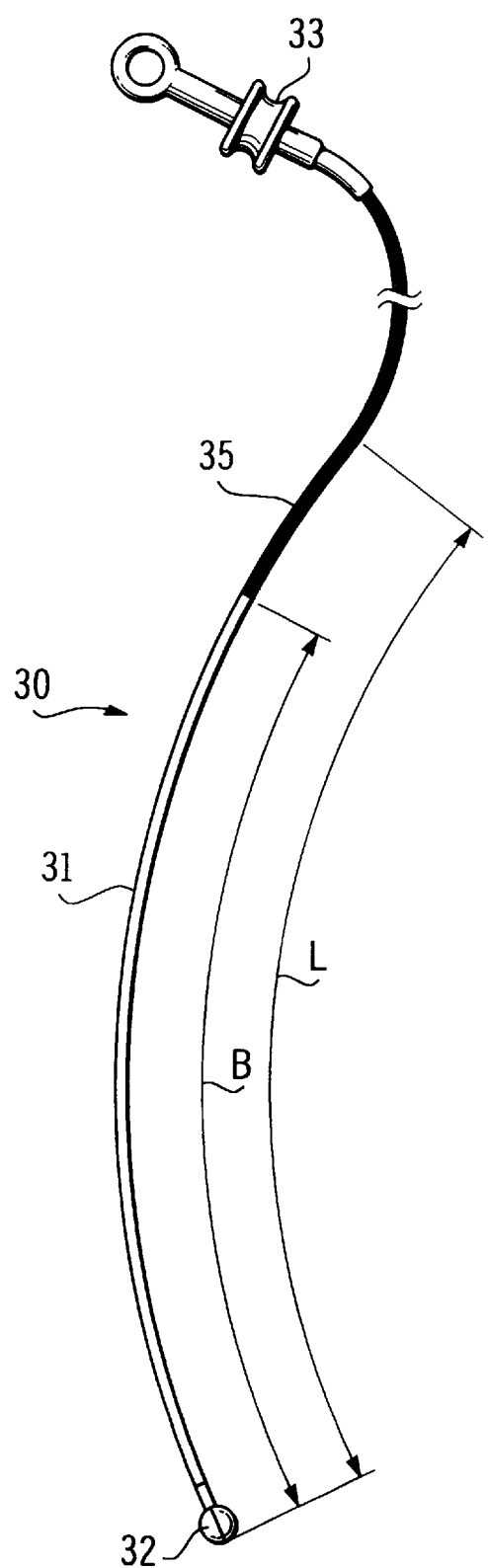
FIG. 2 shows the treatment accessory of FIG. 1.

FIG. 2 shows the treatment accessory 30 according to the first embodiment. The shaft 31 is provided with a marking 35 that runs from the proximal end of the shaft 31 (i.e., where the shaft 31 and the operation unit 33 are connected) to a predetermined distance B from the distal end of the treatment accessory 30.

The marking 35 is a different color than the other portion of the shaft 31 and the distance B is less than the FC length L of the forceps channel 16 by 1 to 20 cm.

Figure 1:
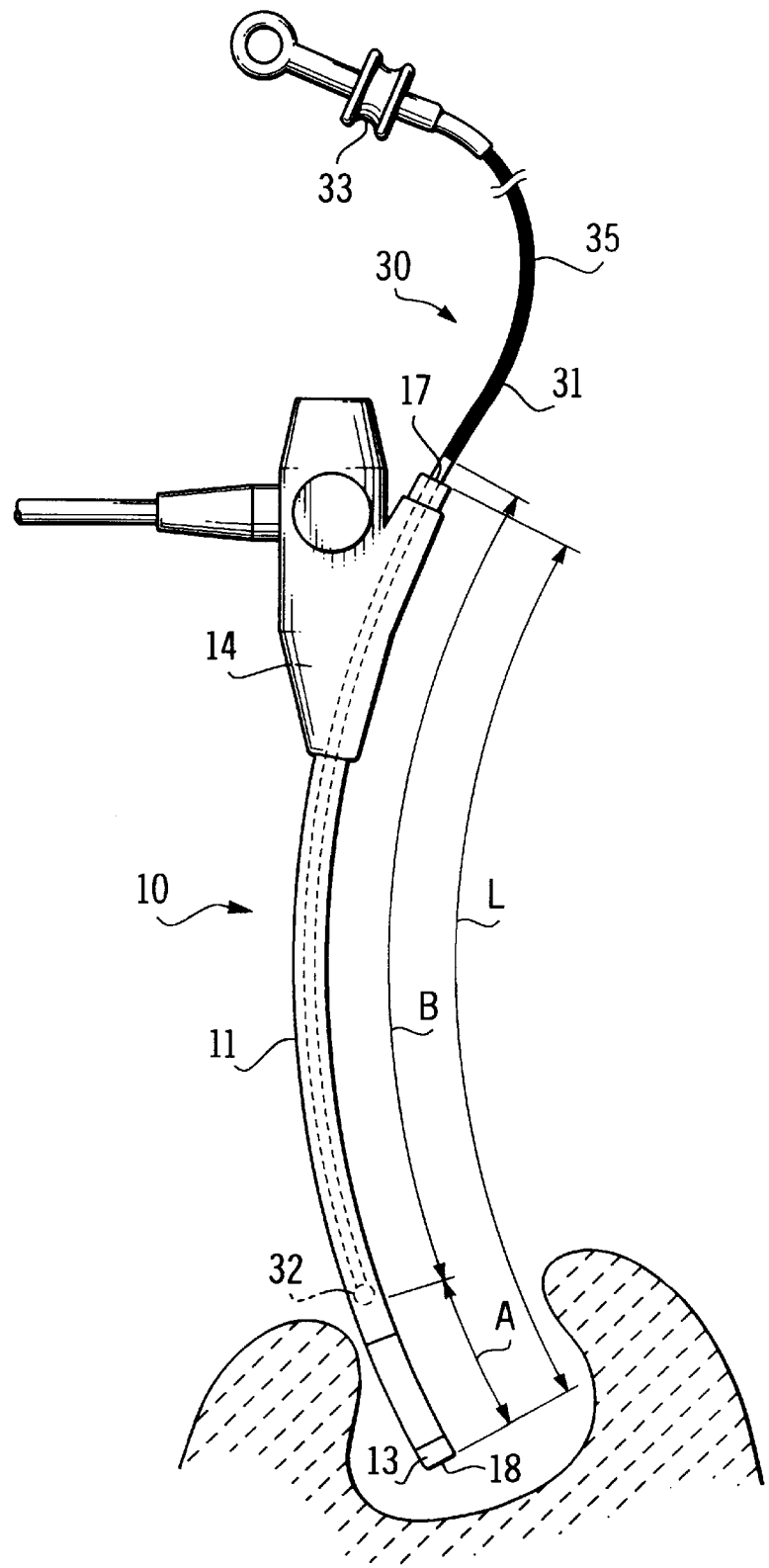
FIG. 1 shows a treatment accessory according to a first embodiment of the invention when inserted in a forceps channel of an endoscope.

FIG. 1 shows the treatment accessory 30 of FIG. 2 being inserted in the forceps channel 16 as the end of the marking 35 is approaching the inlet 17. At this stage, the treatment device 32 at the distal end of the shaft 31 is located inside the forceps channel 16 at a position about a distance A from the outlet 18, where length A=FC length L−distance B.

Thus, the operator may insert the distal end of the treatment accessory 30 quickly until the beginning of the marking 35 (i.e., a border where the color of the sheath 31 changes) reaches the inlet 17, after which the treatment accessory 30 can be inserted more slowly to avoid damaging the tissue in the body cavity C as the treatment device 32 is extended from the outlet 18. Since the length M (see FIG. 4) and the length A are known, the extending amount of the treatment device 32 with respect to the outlet 18 can be controlled easily.

If the operator is operating both the endoscope 10 and the treatment accessory 30, as shown in FIG. 4, the operator may be viewing the observing field of the endoscope 10 and may not see the marking 35. Accordingly, it may be beneficial to form the marking 35 to be noticeable to the sense of touch. For example, by changing the hardness, thickness, the condition of the surface, or the like, of the shaft 31 at the marking 35, or at least the position corresponding to the border of the marking 35 and the other portion of the shaft 31.

The length A, and accordingly, the distance B, may be determined according to the needs of the operator and the assistant. For example, when the operator operates both the endoscope 10 and the treatment accessory 30, it may be preferable that the operator recognizes that the treatment device 32 approaches the outlet 18 earlier. In such a case, the length A may be set to about 5 to 20 cm. On the other hand, if the treatment accessory 30 is operated by the assistant as shown in FIG. 3, the assistant can concentrate on operating the treatment accessory 30 and, accordingly, the length A may be made smaller. For example, the length A can be set to 1 to 10 cm.

Figure 5:
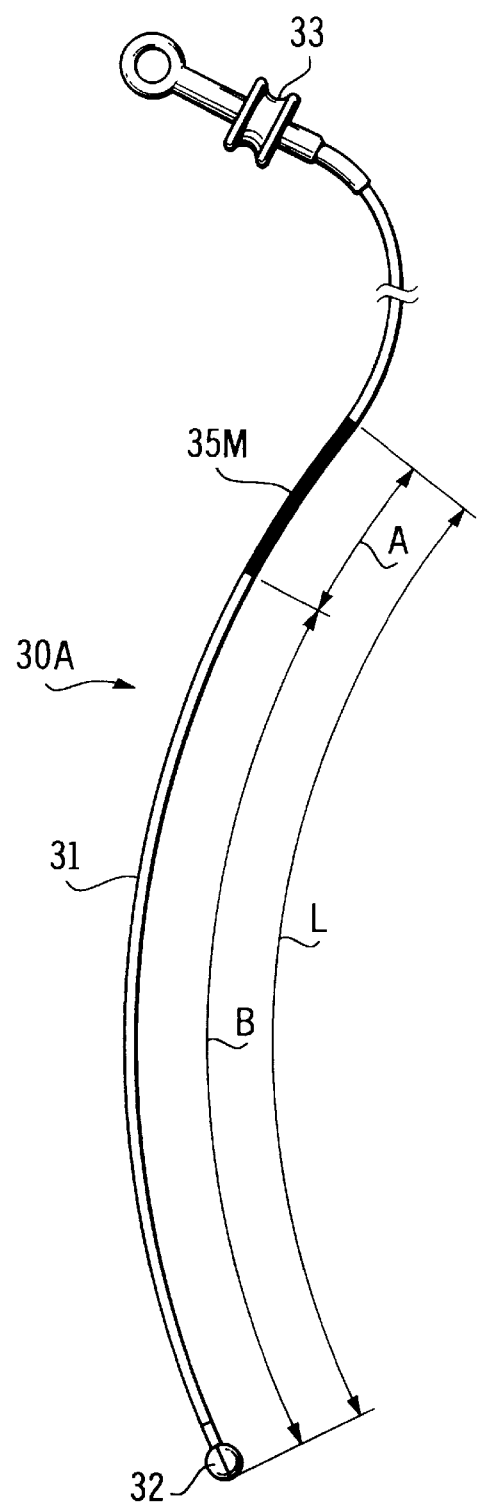
FIG. 5 shows a treatment accessory according to a second embodiment of the invention.

FIG. 5 shows a treatment accessory 30A according to a second embodiment.

In the treatment accessory 30A, a marking 35M is formed between an area from a position that is approximately the FC length L from the distal end of the treatment accessory 30 rather than from the proximal end of the shaft 31, and the predetermined distance B from the distal end of the treatment accessory 30A. In other words, the length of the marking 35M is substantially the same as the length A shown in FIG. 1. With the marking 35M, when the treatment device 32 has reached the end of the forceps channel 16, the marking 35M is entirely inserted into the forceps channel 16, and accordingly the operator can recognize the position of the movable device 32 clearly. That is, when the marking 35M is about to enter the inlet 17 (see FIG. 1), the distance between the distal end of the endoscope 10 and the distal end of the treatment accessory 30A is A, and when the marking 35M has been inserted in the forceps channel 16 entirely, the treatment device 32 has located at the outlet 18 (see FIG. 1).

Figure 6:
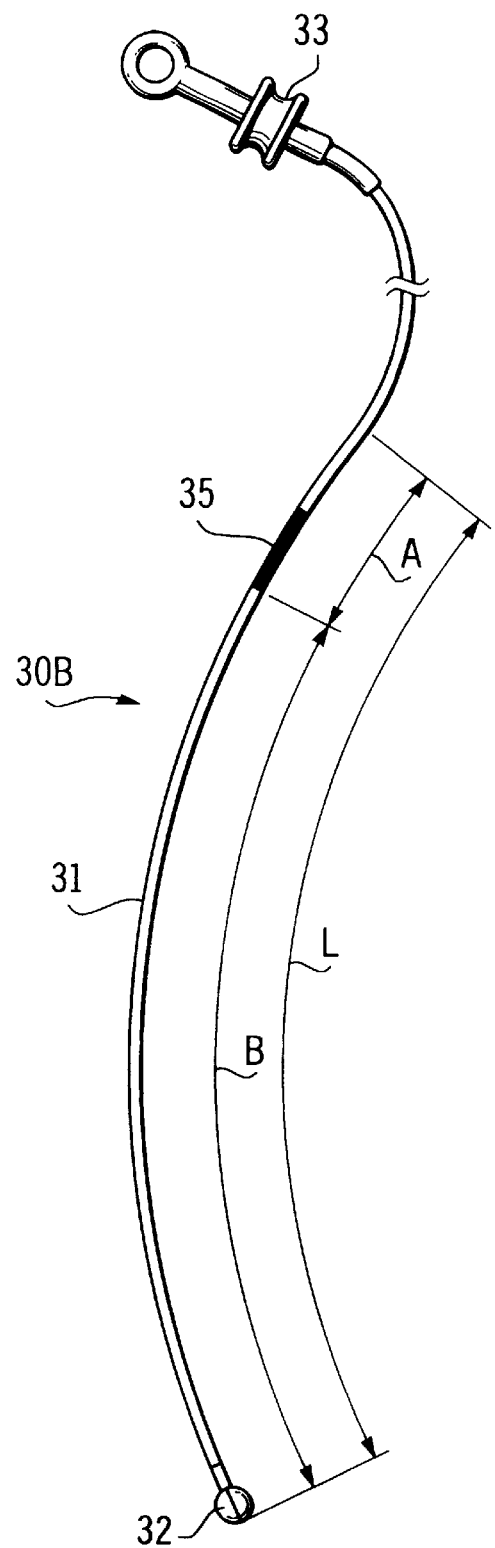
FIG. 6 shows a treatment accessory according to a third embodiment of the invention.

It should be noted that the length of the marking 35 is not limited to a particular value, and can be set accordingly to a smaller length (shown in FIG. 6 as a third embodiment) as long as an operator can recognize that the distal end of the treatment accessory 30 (i.e., the treatment device 32) is located at a predetermined position inside the forceps channel. With such an arrangement, the operator can stop moving the treatment accessory forward before the distal end thereof extends from the distal end of the endoscope 10.

Generally, when a treatment accessory is inserted in the forceps channel, a tap formed from elastic material is attached at the inlet of the forceps channel (see below with regard to FIGS. 20 and 21). The tap has a planner surface formed with a slit, and through the slit, the treatment accessory is inserted in the forceps channel. If a convex, concave or rough portion, or the like which is different from the other portion is formed on a shaft of the treatment accessory as the marking, the operator can feel the passage of such a portion through the slit since the operator can feel a click or a change of resistance, and can stop the inserting operation immediately. In such a case, the length of the marking, i.e., the convex, concave, or rough portion is from 0.5 to 3 cm.

According to the above described first through third embodiments, the marking, or an indicating portion, is provided to indicate that the distal end of the treatment accessory has reached a predetermined position inside the forceps channel. Therefore, when the operator moves the treatment accessory quickly, if he/she stops inserting the treatment accessory immediately when he/she detects the that the marking is at or near the inlet, he/she can stop the movement before the distal end of the treatment accessory extends from the distal end of the forceps channel. Further, since the length between the distal end of the forceps channel and the position where the treatment device is located when the marking is detected is relatively short, by then inserting the treatment accessory by a relatively small amount, e.g., by small pushes, the treatment device can be extended from the distal end of the forceps channel. Therefore, the treatment accessory can be positioned quickly, without a risk of damaging the tissue in a human cavity.

FIGS. 7 through 10 show four different endoscopes 10, 10A, 10B and 10C.

The first endoscope 10 shown in FIG. 7 is the same as that shown in FIG. 1. The endoscope 10 includes the insertion section 11, the length of which is L1. The proximal end of the insertion section 11 is connected to the manipulation unit 14. The forceps channel 16 is formed through the entire length of the insertion section 11, and in the manipulation unit 14, from the inlet 17 to the outlet 18. The length of the forceps channel 16 at a portion from the inlet 17 to a position where the manipulation unit 14 and the insertion section 11 is connected is G. The sum of the lengths L1 and G is equal to the length L shown in FIG. 1.

FIG. 8 shows the endoscope 10A, which has a substantially similar structure to that shown in FIG. 7 or 1.

The second endoscope 10A includes an insertion section 11A having a length L2. The proximal end of the insertion section 11A is connected to a manipulation unit 14A. A forceps channel 16A is formed through the entire length of the insertion section 11A, and in the manipulation unit 14A, from an inlet 17A to an outlet 18A. The length of the forceps channel 16A at a portion from the inlet 17A to a position where the manipulation unit 14A and the insertion section 11A is connected is G. Note that the only substantial difference of the endoscope 10A with respect to the endoscope 10 is the length L2 of the insertion section 11A.

The third endoscope 10B shown in FIG. 9 includes an insertion section 11B having a length L3. The proximal end of the insertion section 11B is connected to a manipulation unit 14B. A forceps channel 16B is formed through the entire length of the insertion section 11B, and in the manipulation unit 14B, from an inlet 17B to an outlet 18B. The length of the forceps channel 16B at a portion from the inlet 17B to a position where the manipulation unit 14B and the insertion section 11B is connected is G. Note that the only substantial difference of the endoscope 10B with respect to the endoscope 10 is the length L3 of the insertion section 11B.

The fourth endoscope 10C shown in FIG. 10 includes an insertion section 11C having a length L4. The proximal end of the insertion section 11C is connected to a manipulation unit 14C. A forceps channel 16C is formed through the entire length of the insertion section 11C, and in the manipulation unit 14C, from an inlet 17C to an outlet 18C. The length of the forceps channel 16C at a portion from the inlet 17C to a position where the manipulation unit 14C and the insertion section 11C is connected is G. Note that the only substantial difference of the endoscope 10C with respect to the endoscope 10 is the length L4 of the insertion section 11C.

The relationship between the lengths of the insertion sections 11, 11A, 11B and 11C is expressed as:

$$L1<L4<L2<L3.$$

The lengths of the forceps channels 16, 16A, 16B and 16C are (L1+G), (L2+G), (L3+G) and (L4+), respectively, which are different from each other.

Figure 11:
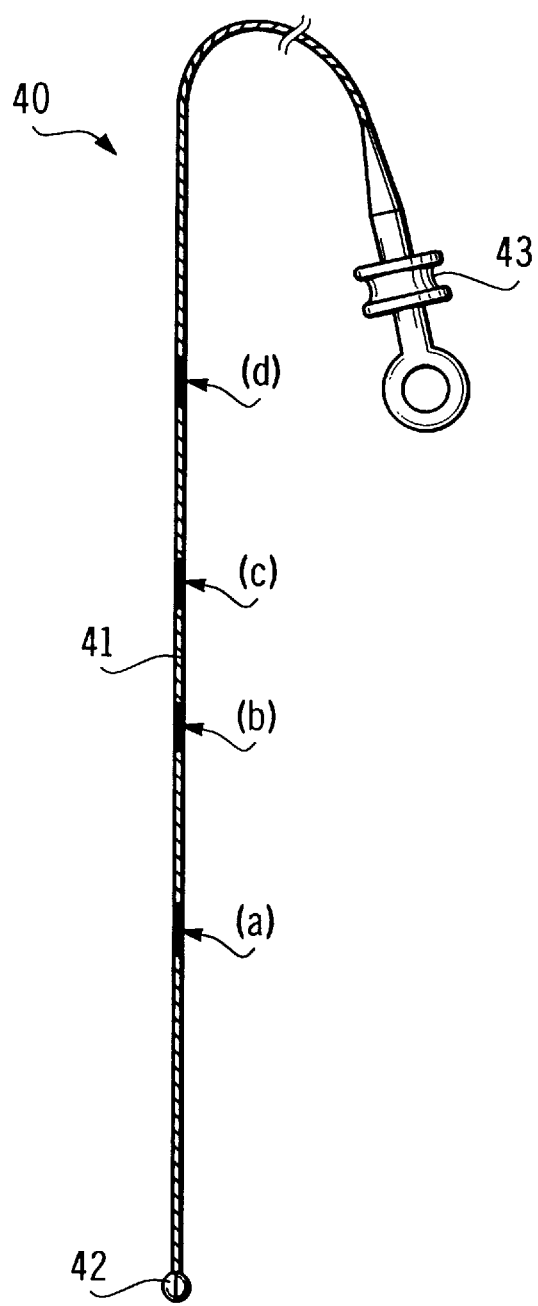
FIG. 11 shows a treatment accessory according to a fourth embodiment of the invention.

FIG. 11 shows a treatment accessory 40 according to a fourth embodiment of the invention. The treatment accessory 40 has a shaft 41 which is made of a closely wound stainless steel wire or a synthetic resin such as tetrafluoraethylene. At the distal end of the shaft 41, a treatment device 42 such as forceps is provided.

The shaft 41 and the treatment device 42 can be slidably inserted in any of the forceps channels 16, 16A, 16B or 16C. The proximal end of the shaft 41 is connected with an operation unit 43 for manipulating the treatment device 42.

As shown in FIG. 11, first to fourth marks (a)–(d) are provided on the shaft 41. The marks (a)–(d) correspond to the lengths of the forceps channels 16, 16A, 16B or 16C. Specifically, the first mark (a) corresponds to the first endoscope 10; the second mark (b) corresponds to the fourth endoscope 10C; the third mark (c) corresponds to the second endoscope 10B; and the fourth mark (d) corresponds to the third endoscope 10C. The four marks (a)–(d) have different colors and/or textures from that of the other portion of the shaft 41.

Figure 12:
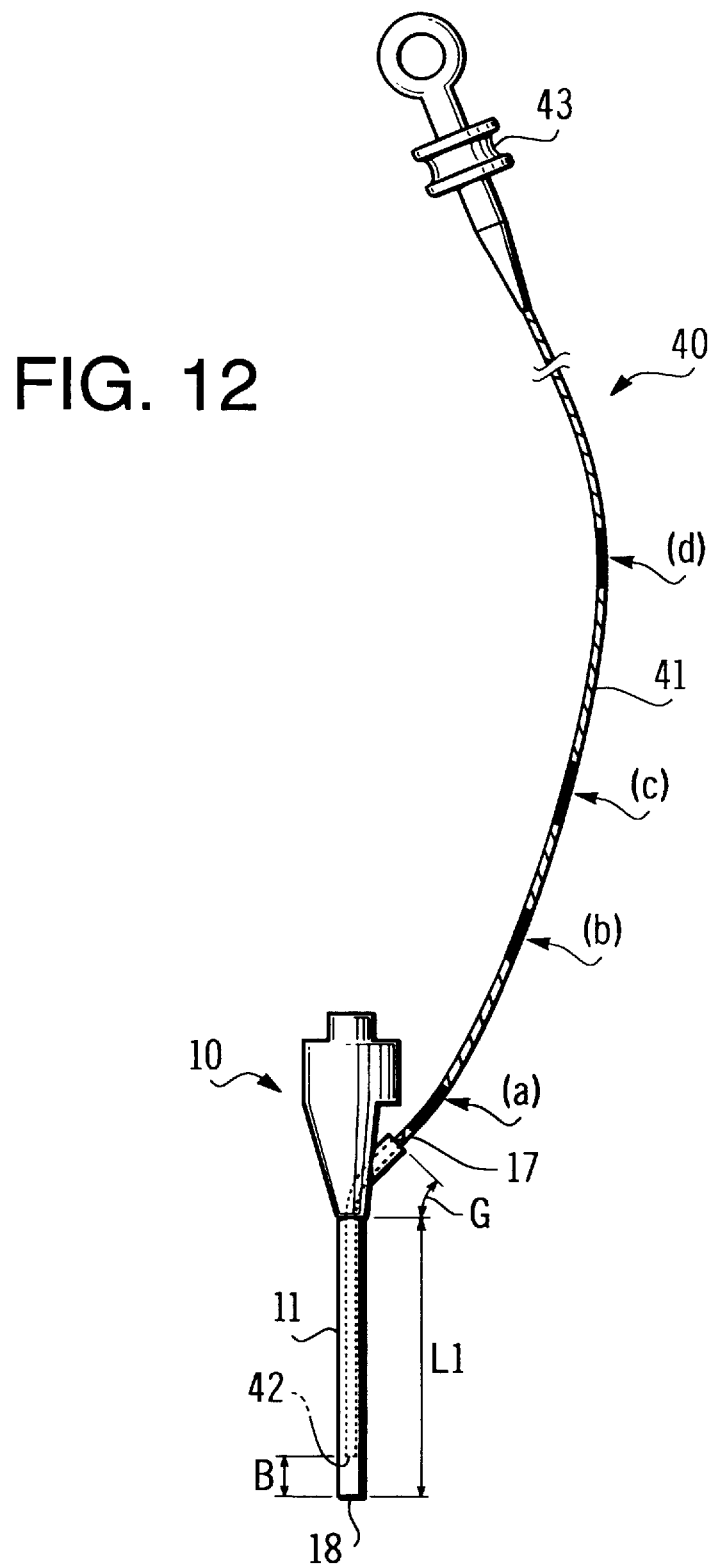
FIG. 12 shows the treatment accessory of FIG. 11 inserted in the endoscope of FIG. 7.

FIG. 12 shows the treatment accessory 40 being used in the first endoscope 10. When the first mark (a) is about to enter the inlet 17, the treatment device 42 is located inside the forceps channel 16 at a position a length B from the outlet 18, where B is 1–10 cm. Thus, the treatment accessory 40 can be quickly inserted in the forceps channel 16 and safely stopped before the treatment device 42 extends from the outlet 18.

Figure 13:
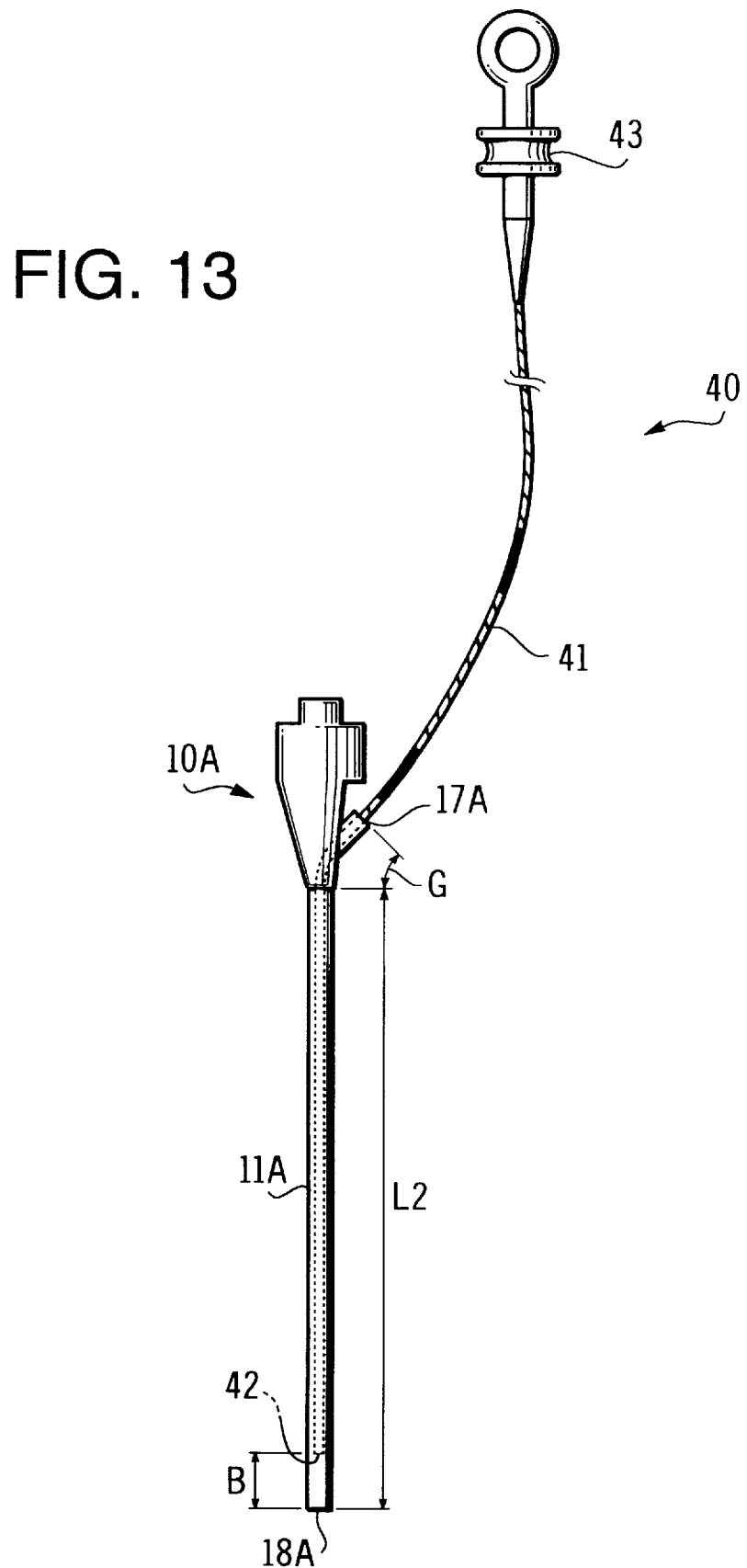
FIG. 13 shows the treatment accessory of FIG. 11 inserted in the endoscope of FIG. 8.

FIG. 13 shows the treatment accessory 40 being used in the second endoscope 10A. When the third mark (c) is about to enter the inlet 17A, the treatment device 42 is located inside the forceps channel 16A at a position a length B from the outlet 18A, where B is 1–10 cm. Thus, the treatment accessory 40 can be quickly inserted in the forceps channel 16A and safely stopped before the treatment device 42 extends from the outlet 18A.

Figure 14:
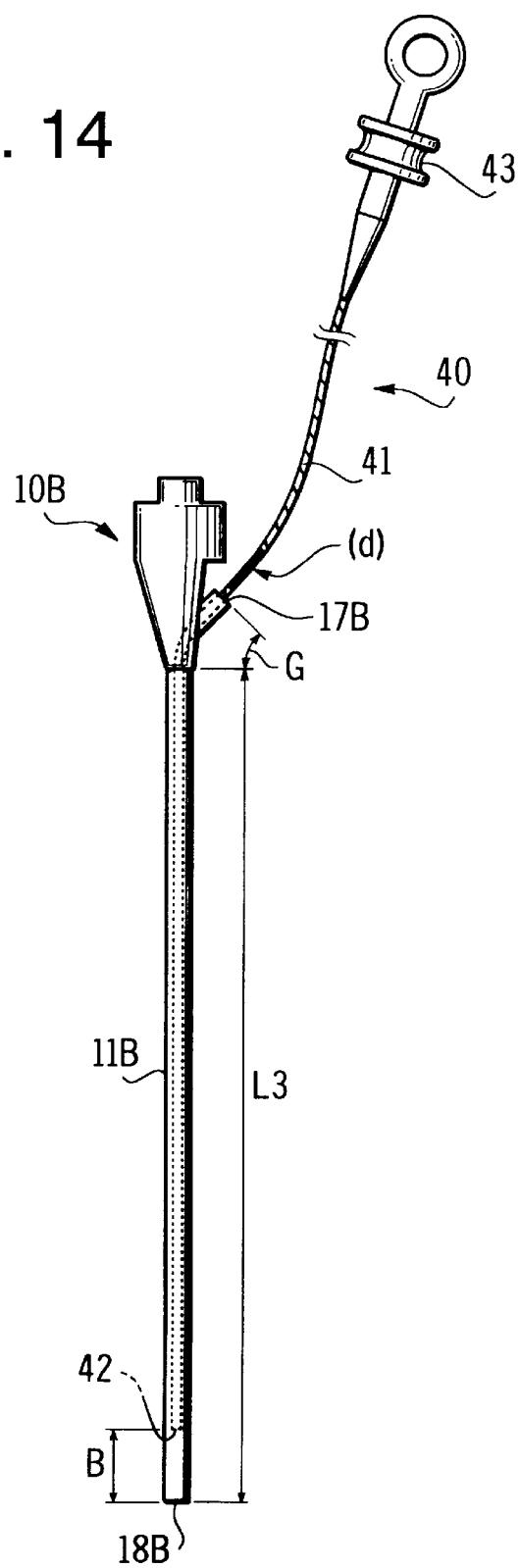
FIG. 14 shows the treatment accessory of FIG. 11 inserted in the endoscope of FIG. 9.

FIG. 14 shows the treatment accessory 40 being used in the third endoscope 10B. When the fourth mark (d) is about to enter the inlet 17B, the treatment device 42 is located inside the forceps channel 16B at a position a length B from the outlet 18B, where B is 1–10 cm. Thus, the treatment accessory 40 can be quickly inserted in the forceps channel 16B and safely stopped before the treatment device 42 extends from the outlet 18B.

As described above, it is preferable, although not necessary, that the four marks (a)–(d) have different colors from each other. In such a case, the color of each mark can be determined in accordance with the length of the forceps channels. Alternatively, the colors of the marks may be determined in accordance with types of endoscopes to which each of the marks correspond. Further alternatively, the color may be determined in accordance with the purpose, or portion of the body to which the endoscope corresponding to each mark is used.

In anyone of the above alternatives, it is advantageous if the inlet of the endoscope has the same color as the mark corresponding thereto.

According to the fourth embodiment, each of the marks indicates that the distal end of the treatment accessory has reached a predetermined position inside the forceps channel. Therefore, when the operator moves the treatment accessory quickly, he/she can stop inserting before the distal end of the treatment accessory extends from the distal end of the forceps channel regardless of the length of the forceps channel. Further, since the length between the distal end of the forceps channel and the position where the treatment device is located when the mark is recognized is relatively short, by inserting the treatment accessory by a relatively small amount, e.g., by small pushes, the treatment device can be extended from the distal end of the forceps channel and may be located at an appropriate position. Therefore, the treatment accessory can be used for various endoscopes and in each endoscope, the treatment accessory can be positioned quickly, without a risk of damaging the tissue in a human cavity.

It should be noted that, in the fourth embodiment, four marks (a) through (d) are provided on the shaft. The number of marks is not limited to four, and could be any number greater than one. In other words, the number and positions of the marks should be determined in accordance with the endoscope for which the treatment accessory is used.

Figure 15:
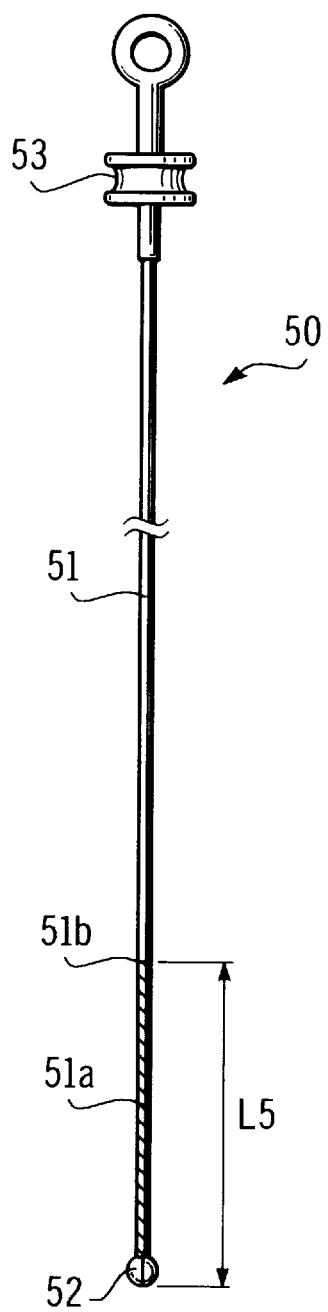
FIG. 15 shows a treatment accessory according to a fifth embodiment of the invention.

FIG. 15 shows a treatment accessory 50 according to a fifth embodiment. The treatment accessory 50 includes a flexible shaft 51 made of a synthetic resin such as tetrafluoraethylene, or a closely wound wire. A treatment device 52 is provided at the distal end of the shaft 51.

The proximal end of the shaft 51 is connected to an operation unit 53 for remotely operating the treatment device 52 by a wire (not shown) inserted through the shaft 51.

A colored area 51a is formed on the shaft 51 from the distal end of the shaft 51 to a condition changing position 51b. The colored area 51a has a different color from the other portion of the shaft 51. A length L5 of the colored area 51a is defined as a length between the condition changing position 51b and the distal end of the treatment device 52.

The length L5 may be adjusted according to the use, i.e., a portion of a human cavity to which the treatment accessory 50 is to be used. For example, the length L5 may be set at approximately 30 cm if the treatment accessory 50 is used in an endoscope for inspection of a large intestine or the like, i.e., having a relatively long insertion section of approximately 150 cm. If the treatment accessory is for an endoscope for bronchial inspection or the like, i.e., having a relatively short insertion section of approximately 50 cm, the length L5 may be set approximately at 10 cm.

In any case, the length L5 is preferably set greater than the amount by which the treatment device 52 extends from the end of the forceps channel when the treatment accessory 50 is used normally such that the condition changing position 1 remains inside the forceps channel during use of the treatment accessory 50. This is in contrast to some conventional treatment accessories that are provided with graduated marks at the distal end of the shaft in order to measure the amount that a treatment accessory extends beyond an outlet of a forceps channel.

Figure 16:
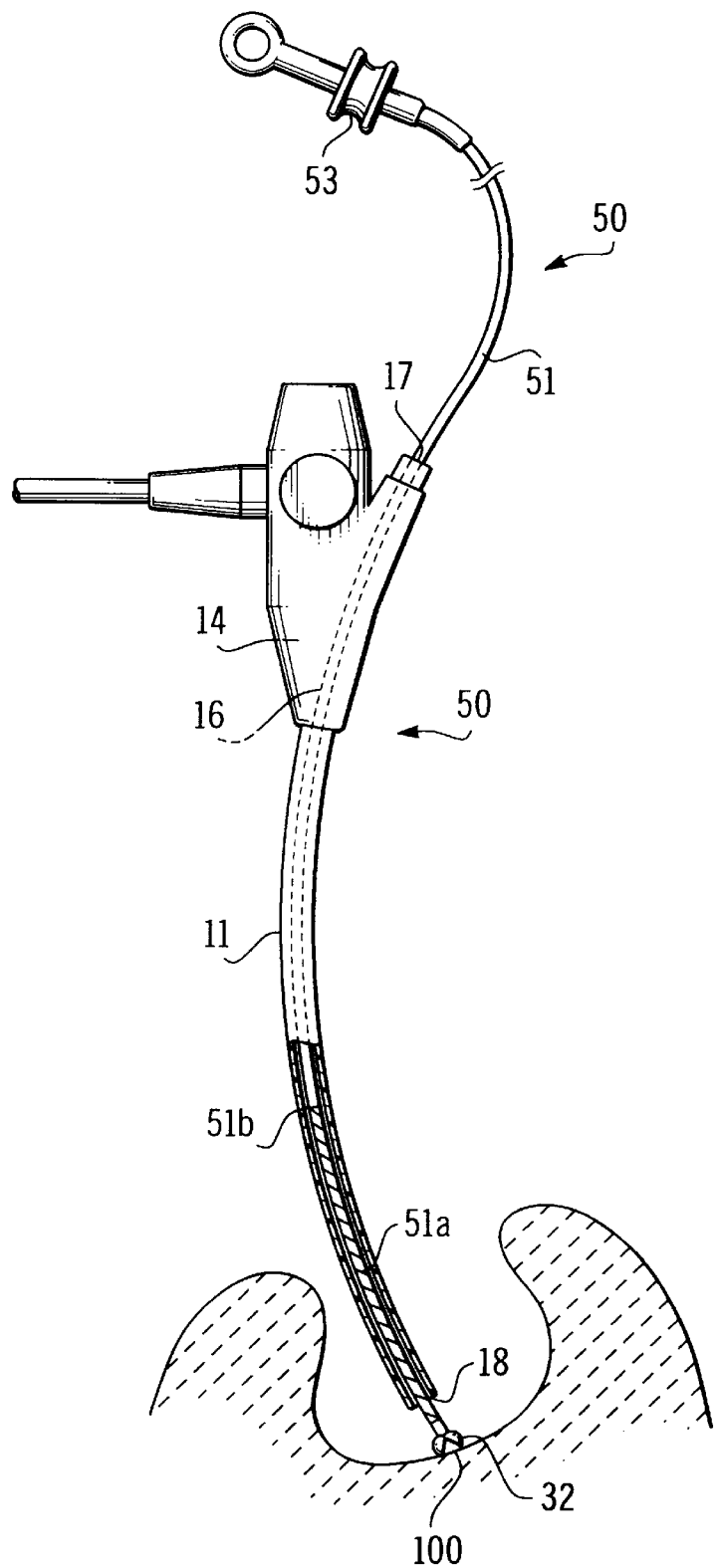
FIG. 16 shows the treatment accessory of FIG. 15 when inserted in a forceps channel of an endoscope.

FIG. 16 shows the treatment accessory 50 shown in FIG. 15 inserted in the forceps channel 16 of the endoscope 10 in order to perform a treatment on an affected part 100.

The endoscope 10 includes the insertion section 11. As described above, the insertion section 11 is a flexible tube for insertion in a human cavity. The proximal end of the insertion section 11 is connected to the manipulation unit 14 (see FIG. 1).

The treatment accessory 50 is inserted from the inlet 17 provided on the manipulation unit 14, and inserted in the forceps channel 16. The treatment device 52 is extended from the outlet 18 formed at the distal end of the insertion section 11, and press contacted onto the affected part 100. As an example, the treatment device 52 is a pair of cup forceps. By operating the operating unit 53, the treatment device 52 is opened or closed and tissue at the affected part 100 is collected.

Figure 17:
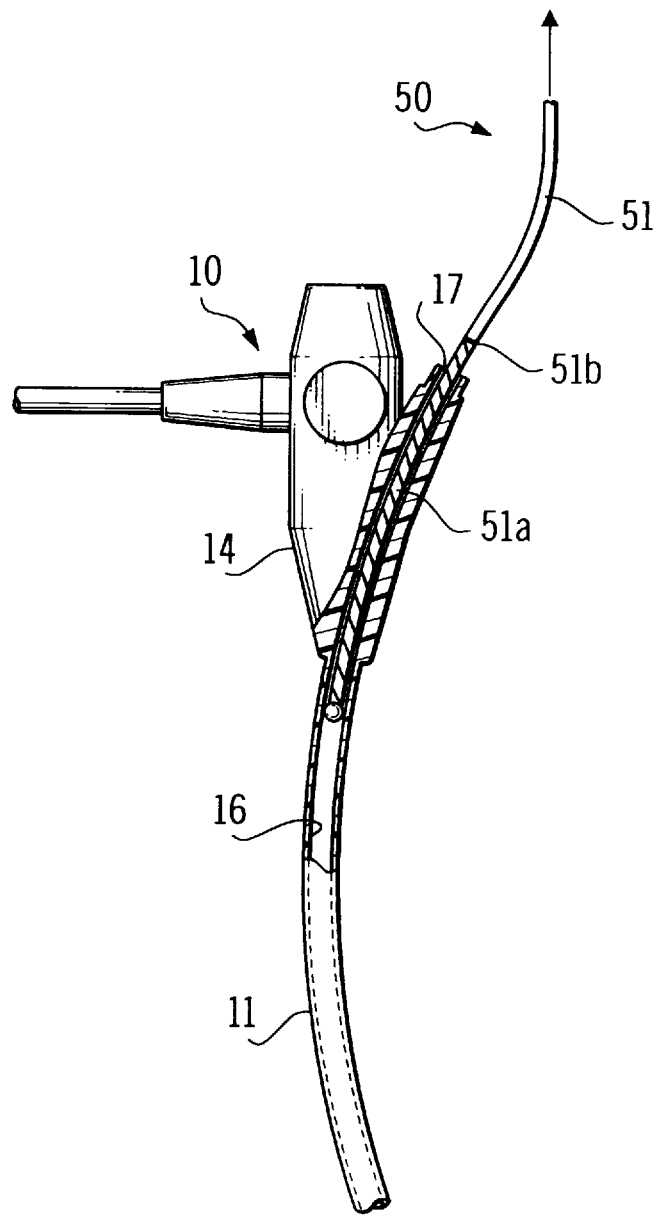
FIG. 17 shows the treatment accessory of FIG. 15 being removed from a forceps channel of an endoscope.

FIG. 17 shows the treatment accessory 50 being removed from the forceps channel 16. Specifically, FIG. 17 shows the state when the condition changing position 51b has just appeared. In this state, an amount of the treatment accessory equal to the length L5 remains inside the forceps channel 16. Accordingly, during removal of the treatment accessory 50, the operator can pull the treatment accessory quickly until the condition changing position 51b appears, after which, the shaft 51 may be pulled more slowly, such that the shaft 51 does not jump or whip upon exiting the forceps channel 16 and thus a loss of collected tissue, sprinkling of adhered fluid can be avoided.

Figure 18:
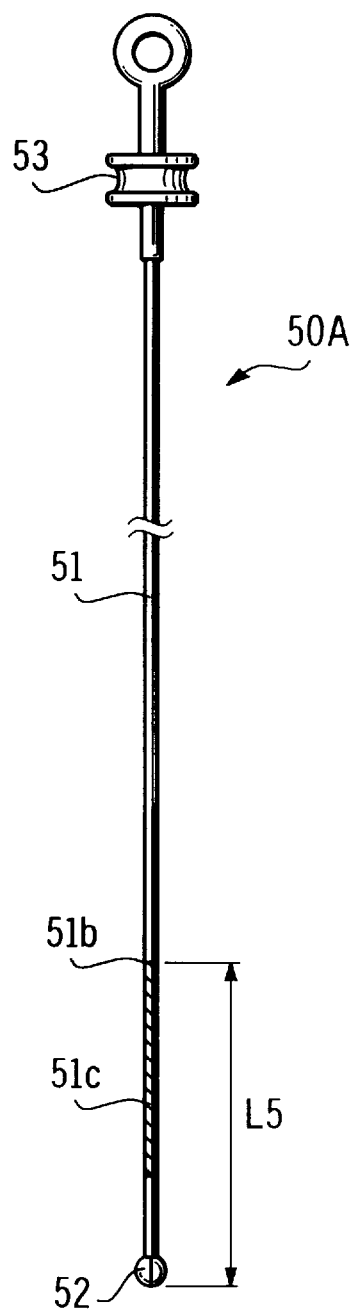
FIG. 18 shows a treatment accessory according to a sixth embodiment of the invention.

FIG. 18 shows a treatment accessory 50A according to a sixth embodiment of the invention. In this sixth embodiment, a colored area 51c is shorter than that of the fifth embodiment in that, the colored area 51c starts at a position which is slightly spaced from the distal end of the shaft 51. With this structure, when the colored area 51c has been completely pulled out of the inlet 17 of the endoscope 10, the operator recognizes that the end of the shaft 51 is about to appear. Thus, the operator can further control the pulling speed and avoid the jumping or whipping of the shaft 51, which allows a quick removal of the treatment accessory 50A from the forceps channel 16.

Figure 19:
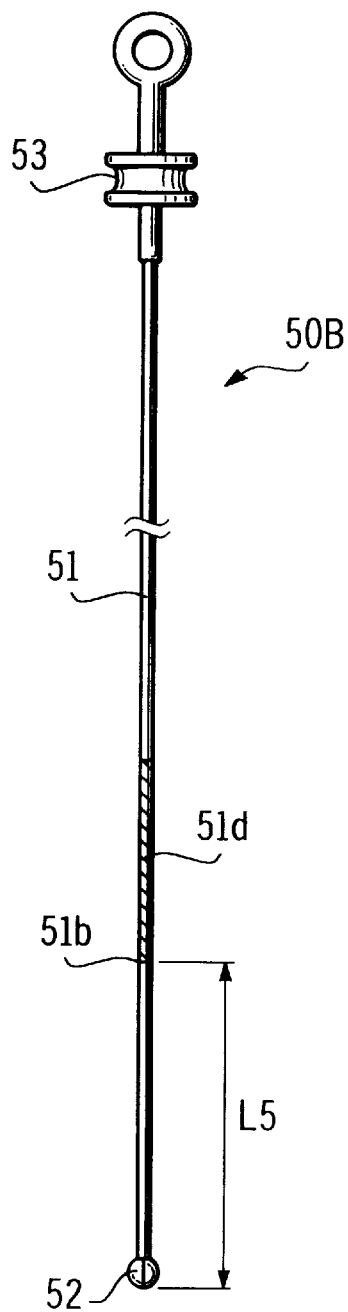
FIG. 19 shows a treatment accessory according to a seventh embodiment of the invention.

FIG. 19 shows a treatment accessory 50B according to a seventh embodiment. In the seventh embodiment, a colored area 51d starts from the condition changing position 51b and extends towards the proximal end of the shaft 51. According to this structure, the operator can recognize that the condition changing position 51b is approaching when the colored area 51d appears from the inlet 17, and reduce the pulling speed accordingly. In this case, the length of the colored area 51d may preferably be set to 1–5 cm.

The colored area 51a (51c, or 51d) is not limited to a colored area, but may be substituted with any distinctive marking and may alternatively be a textured area such that the operator may identify the textured area by touch rather than by sight.

As mentioned before and described in more detail below, generally, when a treatment accessory is inserted in the forceps channel, a tap formed from elastic material is attached at the inlet of the forceps channel. The tap has a planar surface formed with a slit, and through the slit, the treatment accessory is inserted in the forceps channel. If a convex, concave or rough portion, or the like which is different from the other portion is formed on a shaft of the treatment accessory instead of the color area, the operator can feel the passage of such a portion through the slit, i.e., the operator can feel a click or a change of resistance, and can stop the removing operation immediately. In such a case, the length of the mark, i.e., the convex, concave, or rough portion, replacing the color area may range from 0.5 to 3 cm.

Figure 20:
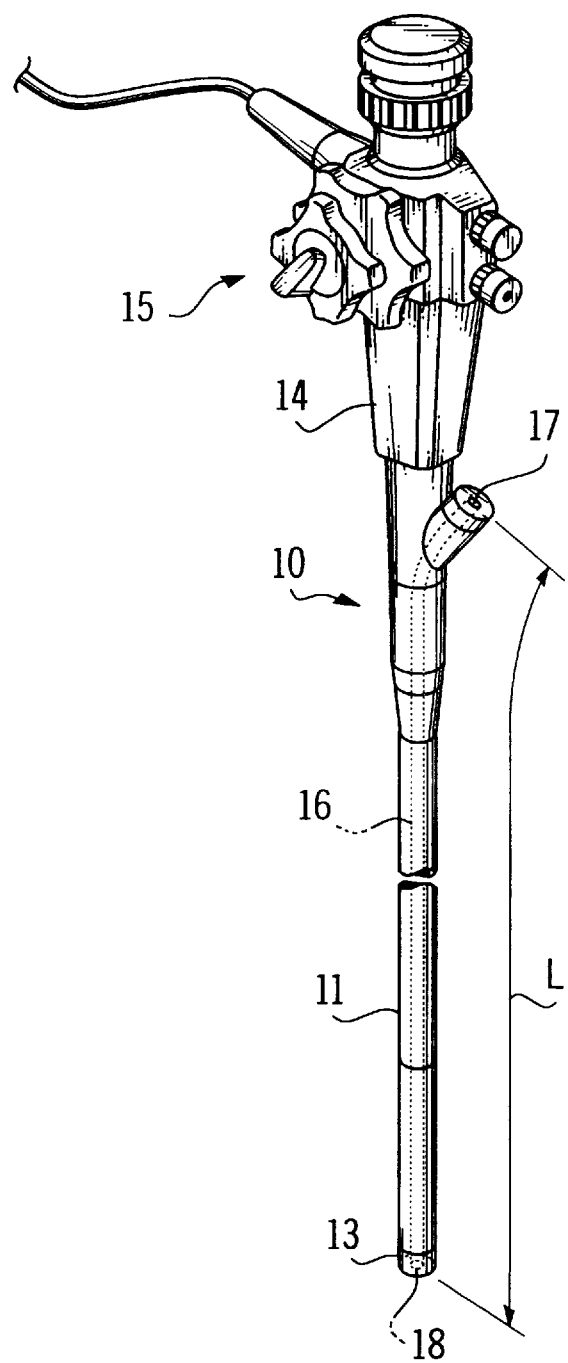
FIG. 20 is a schematic perspective view of an endoscope similar to that shown in FIG. 1.
Figure 21:
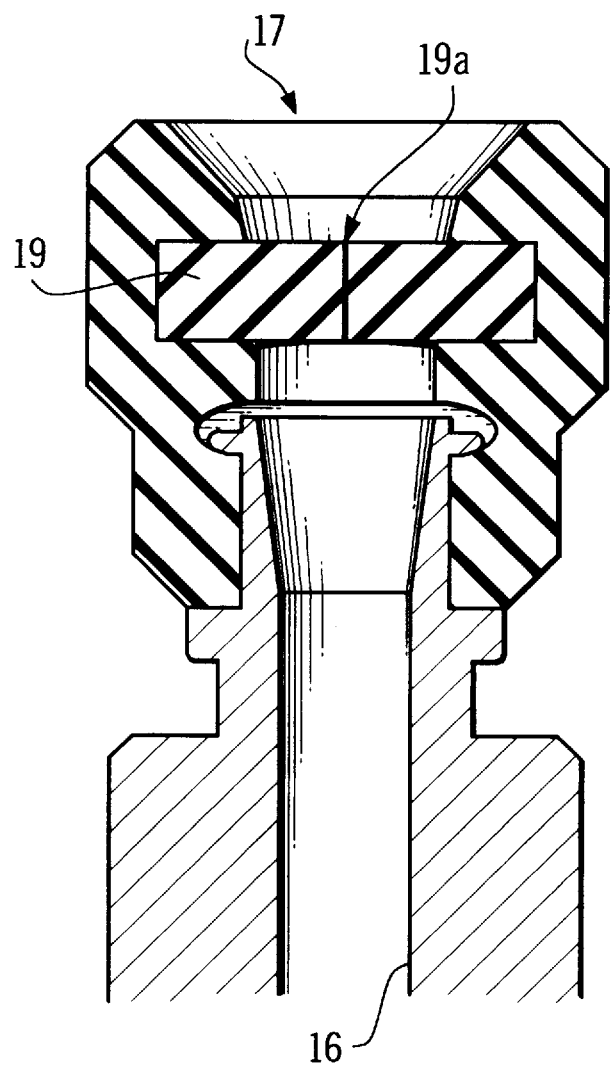
FIG. 21 is a cross-section of a forceps tap of the endoscope of FIG. 20.

FIG. 20 is a schematic perspective view of the endoscope 10 similar to that shown in FIG. 1.

The endoscope 10 includes the insertion section 11 which is to be inserted in a body cavity. The insertion section 11 is formed as a flexible tube and the proximal end of the insertion section 11 is connected to the manipulation unit 14. The distal end of the insertion section 11 is provided with the bendable portion 12, which can be bent by operation of the manipulation knob 15 provided at the manipulation unit 14. At the tip of the bendable portion 12, the end unit 13 accommodating an objective optical system (not shown) is connected.

The forceps channel 16 is formed to extend from an inlet 17 formed on the manipulation unit 14, through the whole length of the insertion section 11, to an outlet 18 formed in the end unit 13. The length of the forceps channel 16, i.e., the distance between the inlet 17 and the outlet 18 is indicated as the FC length L.

At the inlet 17 of the forceps channel 16, a forceps tap 19 for preventing air fed inside the human cavity, fluid inside the body, or the like from leaking back through the forceps channel is attached. An enlarged cross-sectional view of the forceps tap 19 is shown in FIG. 21. The tap 19 is formed from, for example, an elastic rubber plate formed with a slit 19a. The slit 19a is closed due to the elasticity of the rubber plate. A treatment accessory will be inserted through the slit 19a, pushing open the rubber forming the slit 19a. When the treatment accessory has been removed, the slit returns to its original shape. It should be noted that some endoscopes are not provided with the tap 19.

Figure 22:
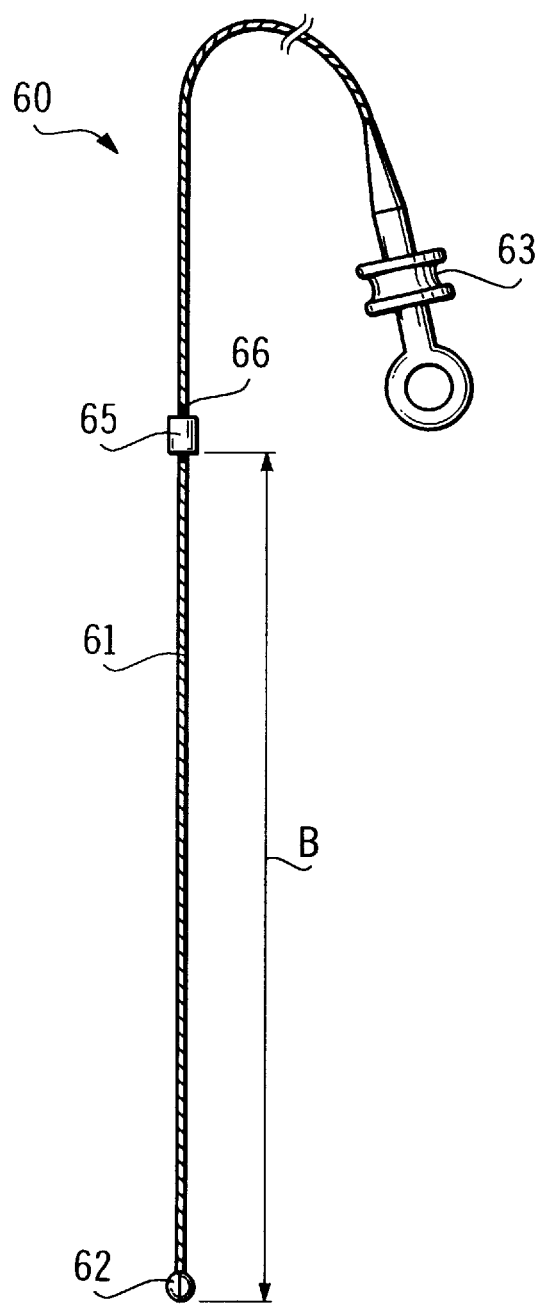
FIG. 22 shows a treatment accessory according to a eighth embodiment of the invention.

FIG. 22 shows a treatment accessory 60 according to an eighth embodiment of the invention.

In this embodiment, the treatment accessory 60 is a biopsy forceps, which has a shaft 61 formed from a closely wound coils having a certain elasticity, and a treatment device 62 (i.e., forceps, in this embodiment) which is provided at the distal end of the shaft 61.

The shaft 61 and the treatment device 62 are slidably inserted in the forceps channel 16 of the endoscope 10.

An operation unit 63 is provided at the proximal end of the shaft 61 for manipulating (e.g., opening and closing the forceps cups) the treatment device 62 through a wire (not shown) which is inserted through the shaft 61.

Figure 23:
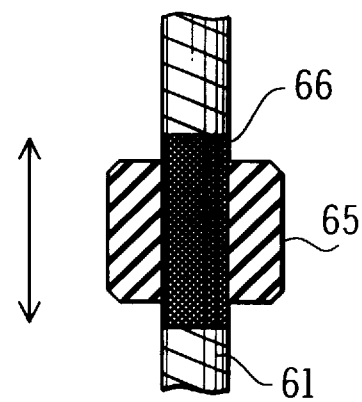
FIG. 23 is a cross-section of a slidable ring of the treatment accessory of FIG. 22.

On the shaft 61, as shown in FIG. 22, at a distance B from the distal end thereof, a slidable ring 65 is fitted. The slidable ring 65, as shown in detail in FIG. 23, is made from rubber or synthetic resin having a certain elasticity, and has a slightly smaller inner diameter than the outer diameter of the shaft 61. Accordingly, the slidable ring 65 is held on the shaft 61 due to the frictional and elastic force generated between the shaft 61 and the slidable ring 65.

On the shaft 61, at the distance B from the distal end of the treatment device 62, a mark area 66 is formed. The mark area 66 has, for example, a different color from the other portions of the shaft 61. By sliding the slidable ring 65 and positioning it on the mark area 66, the slidable ring 65 is located at a predetermined position, i.e., the distance B from the distal end of the treatment accessory 60, accurately.

The slidable ring 65 can slide relative to the shaft 61 along the axial direction of the shaft 61. As described above, there exists a frictional force between the slidable ring 65 and the shaft 61. As the treatment accessory 60 is inserted in the forceps channel 16 of the endoscope 10, the slidable ring 65 reaches and contacts the tap 19 which is attached to the inlet 17 of the forceps channel 16. After the slidable ring 65 has reached the tap 19, only the shaft 61 is inserted further. That is, any slidable ring 65 is prevented by the tap 19 from entering the forceps channel 16. In this situation, if the shaft 61 is further pushed forward to enter the forceps channel 16, the shaft 61 slides relative to the slidable ring 65, and enters in the forceps channel 16. Due to the friction between the shaft 61 and the slidable ring 65, the resistance against the inserting force is increased and may be felt by the operator of the treatment accessory 60.

The distance B indicated in FIG. 22 is set slightly shorter than the FC length L of the forceps channel 16. Preferably, the distance B is from 1 to 20 cm shorter than the FC length L.

Figure 24:
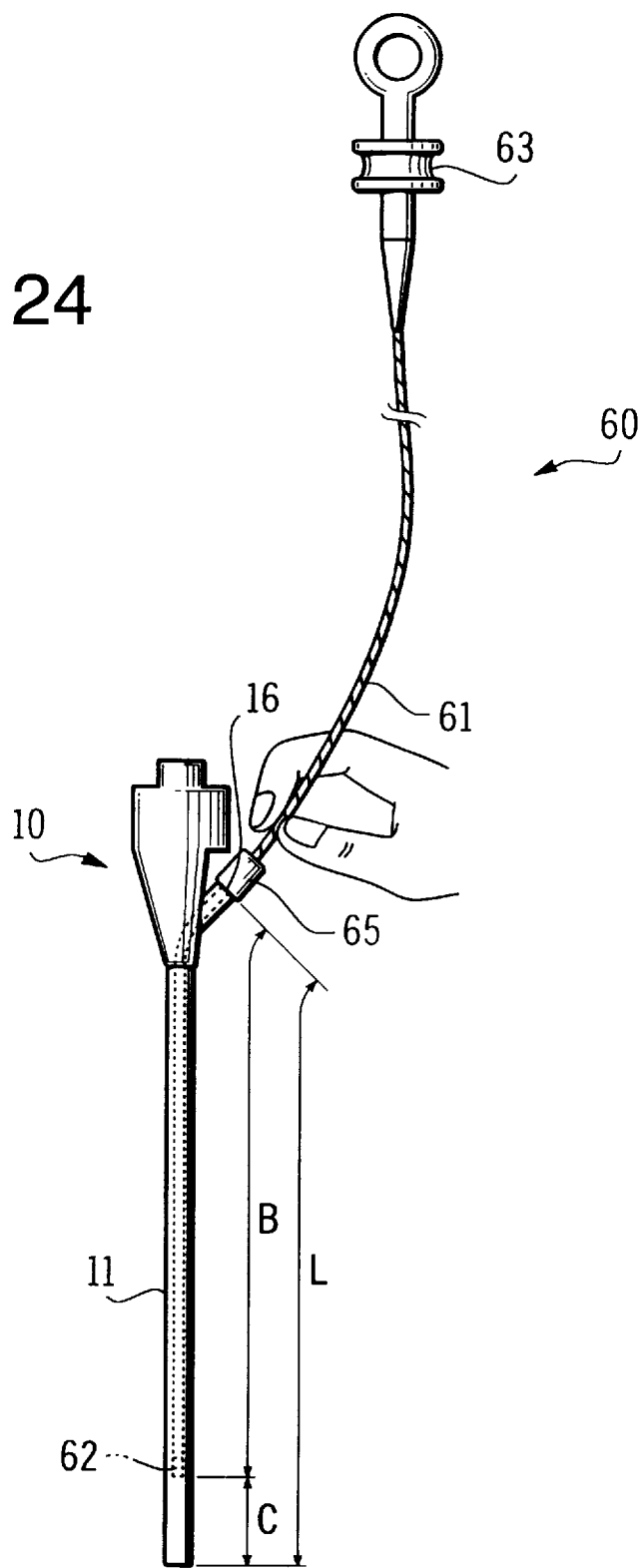
FIG. 24 shows the treatment accessory of FIG. 22 when inserted in a forceps channel of the endoscope of FIG. 20.

Accordingly, as shown in FIG. 24, when the slidable ring 65 has reached the tap 19, the treatment device 62 provided at the tip of the treatment accessory 60 is located at a position which is length C (C=L−B) away from the outlet 18 of the forceps channel 16.

When the treatment accessory 60 is inserted in the forceps channel 16, if the operator feels increased resistance, the insertion can be stopped immediately. At this stage, the distal end of the treatment accessory 60 is still located inside the forceps channel 16. Thereafter, by inserting the treatment accessory 60 slowly, the distal end of the treatment accessory 60 can be extended by an appropriate amount.

Figure 25:
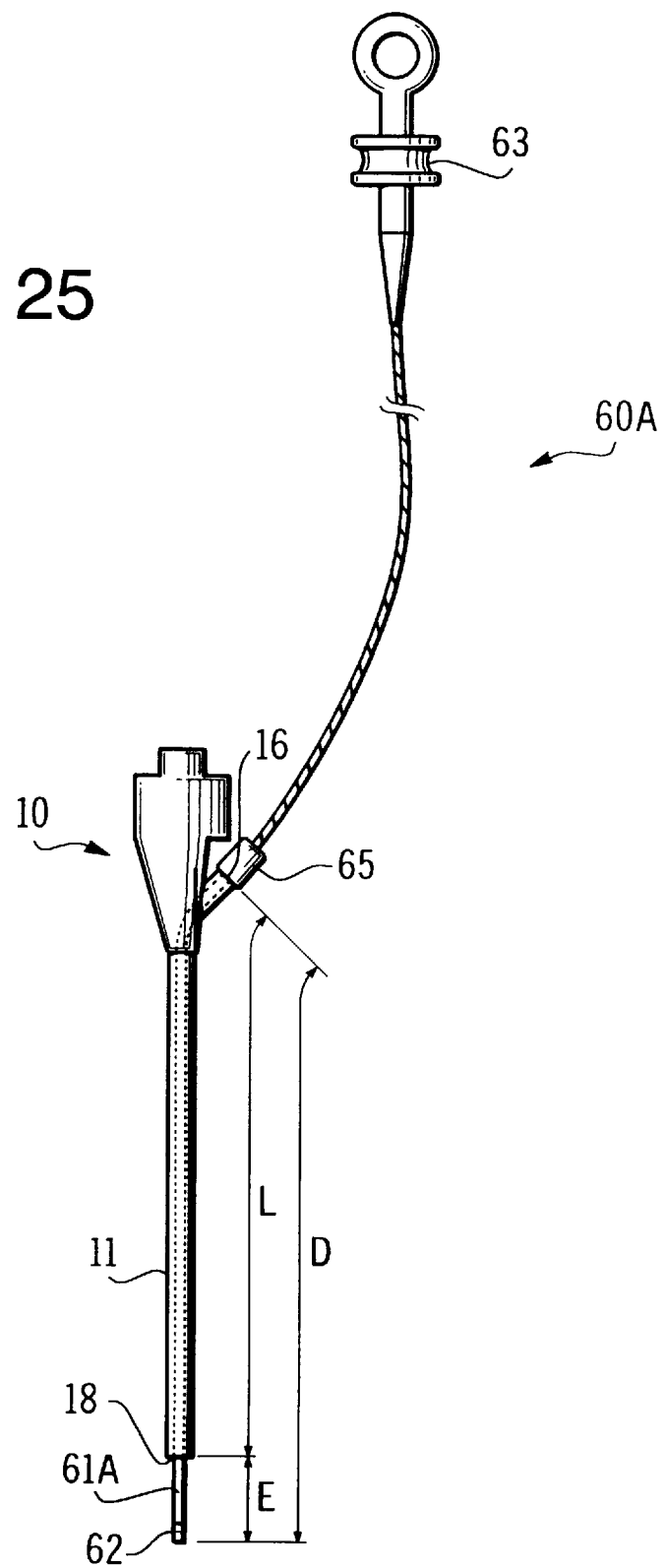
FIG. 25 shows a treatment accessory according to a ninth embodiment of the invention when inserted in a forceps channel of the endoscope of FIG. 20.

FIG. 25 shows a treatment accessory 60A according to a ninth embodiment of the invention.

The treatment accessory 60A is similar to the treatment accessory 61 shown in FIG. 24 except for the initial position of the slidable ring 65. In the treatment accessory 60A, the slidable ring 65 is initially located at a distance D from the distal end thereof. The distance D is a sum of the FC length L of the forceps channel 16, and an extending amount E of the treatment device 62 with respect to the outlet 18 of the forceps channel 16.

According to the arrangement of the treatment accessory 60A, when the operator feels increased resistance as the treatment accessory 60A is inserted, the operator knows that the distal end of the treatment accessory 60A is located at an appropriate position in which the treatment device 62 extends from the distal end of the forceps channel 16 by the extending amount E as shown in FIG. 25. This arrangement is particularly applicable to keeping an appropriate distance to the affected part or to measure a distance or size of the affected part.

Furthermore, since the slidable ring 65 can be located at any position on the shaft 61, even if the length of the insertion section 11 includes manufacturing errors, by fine adjustment of the initial position of the slidable ring 65, any manufacturing error can be compensated.

Figure 26:
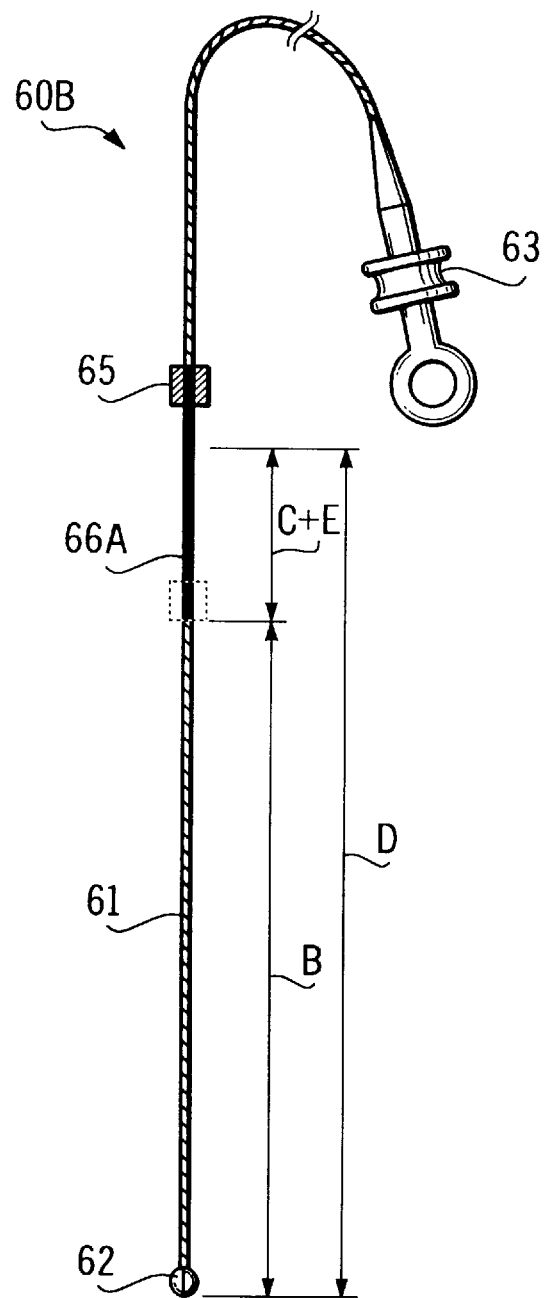
FIG. 26 shows a treatment accessory according to a tenth embodiment of the invention.

FIG. 26 shows a treatment accessory 60B according to a tenth embodiment of the invention.

The treatment accessory 60B can be used similarly to either of the above two embodiments, i.e., similar to the treatment accessory 60 or to the treatment accessory 60A. Specifically, in the treatment accessory 60B, a mark area 66A is formed such that there is a distance B between one end of the mark area 66A and the distal end of the treatment device 62 (cf. FIG. 24), and a distance D between the other end of the mark area 66A and the distal end of the treatment device 62 (cf. FIG. 25).

Alternatively, it is also possible to provide two slidable rings on a shaft similar to the shaft 61 of the treatment accessory 60B. With use of such a treatment accessory, when the first slidable ring, positioned to be a distance B from the distal end of the treatment device 62, reaches the inlet 17 of the endoscope 10, the operator detects that the treatment device 62 is approaching the outlet 18 of the forceps channel 16. By further inserting the shaft 61 in the forceps channel, the first slidable ring moves towards the second slidable ring, located at a distance D from the distal end of the treatment device 62. When the two slidable rings contact, the treatment device 62 is extended from the distal end of the forceps channel by an appropriate extended amount E.

The slidable ring 65 described above has a cylindrical shape. However, the shape of the slidable ring is not limited to cylindrical, the slidable ring may be formed to have various shapes.

Figure 27:
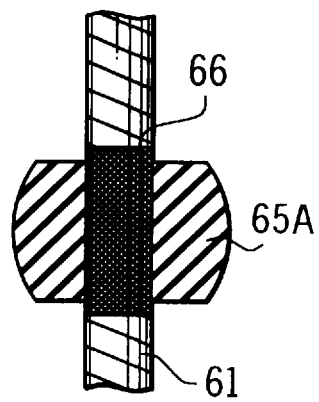
FIG. 27 shows a cross-section of a slidable ring of a treatment accessory according to an eleventh embodiment of the invention.
Figure 28:
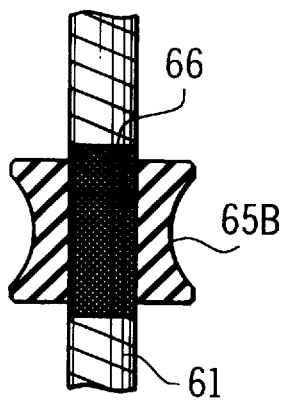
FIG. 28 shows a cross-section of a slidable ring of a treatment accessory according to a twelfth embodiment of the invention.

FIG. 27 shows a slidable ring 65A according to an eleventh embodiment which has a round convex circumferential surface. FIG. 28 shows a slidable ring 65B according to a twelfth embodiment which has a round concave circumferential surface.

Figure 29:
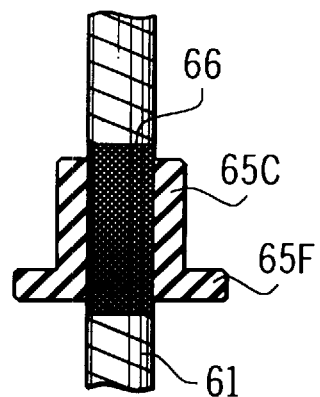
FIG. 29 shows a cross-section of a slidable ring of a treatment accessory according to a thirteenth embodiment of the invention.
Figure 30:
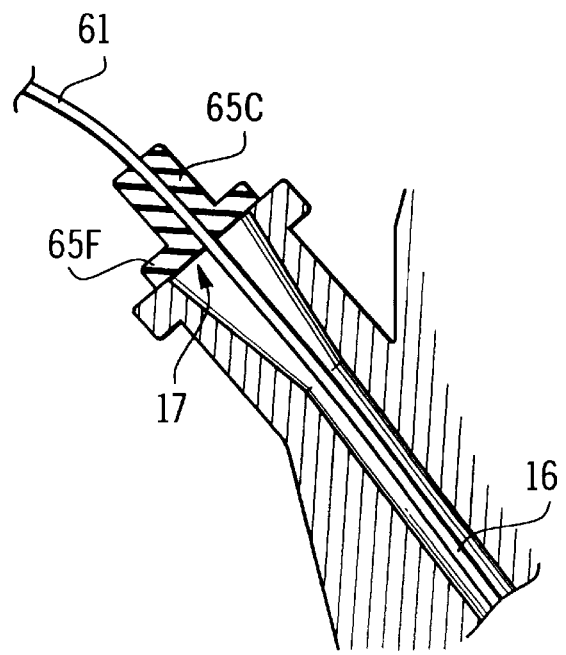
FIG. 30 shows a cross-section illustrating the use of the slidable ring of FIG. 29.

FIG. 29 shows a slidable ring 65C according to a thirteenth embodiment. The slidable ring 65C is a cylindrical member provided with a flange portion 65F at the treatment device side thereof. With use of the slidable ring 65C, even if the inlet 17 of the forceps channel 16 is not provided with a tap, and is open as shown in FIG. 30, the flange portion 65F prevents the slidable ring 65C from entering the forceps channel 16.

Figure 31:
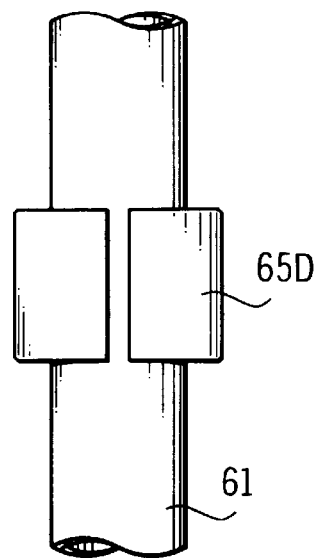
FIG. 31 shows a slidable member of a treatment accessory according to a fourteenth embodiment of the invention.

FIG. 31 shows a slidable member 65D according to a fourteenth embodiment. In this embodiment, instead of a slidable ring, a slidable member 65D which has a C-shape cross section, along a plane perpendicular to the axis of the shaft 61, is used. The slidable member 65D has elasticity and is formed to squeeze, with an elastic force, the shaft 61. The slidable member 65D may be formed from, for example, hard plastic.

Figure 32:
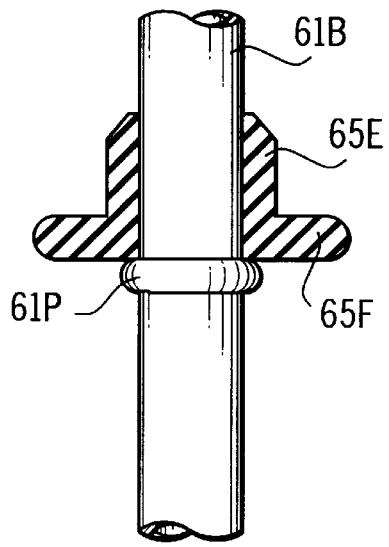
FIG. 32 shows a cross-section of a slidable member of a treatment accessory according to a fifteenth embodiment of the invention.

FIG. 32 shows a slidable member 65E and a shaft 61B according to a fifteenth embodiment of the invention.

In FIG. 32, the slidable member 65E is substantially similar to the slidable ring 65C having a cylindrical portion and a flange portion 65F. The diameter of the flange portion F is greater than the diameter of the inlet 17 of the forceps channel 16. In the fifteenth embodiment, the shaft 61B is provided with a projected portion 61P instead of a mark area. The projected portion 61P is provided on the shaft closer to the treatment device 62 than the slidable ring 65E. By positioning the slidable ring 65E such that the end surface of the slidable ring 65E (i.e., the flange portion 65F) contacts the projected portion 61P, the slidable ring 65E is accurately positioned. It should be noted that the projected portion 61P has a diameter which is smaller than the inner diameter of the forceps channel 16 so that the shaft 61B can be moved freely inside the forceps channel 16.

Figure 33:
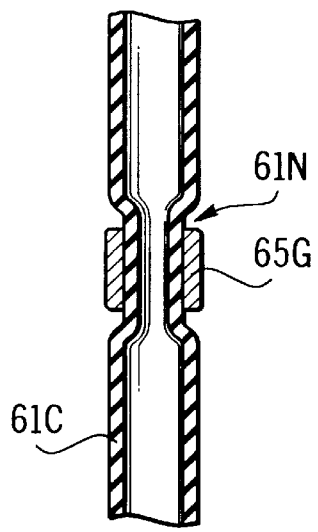
FIG. 33 shows a cross-section of a ring and a shaft of a treatment accessory according to a sixteenth embodiment of the invention.

FIG. 33 shows a ring 65G and a shaft 61C according to a sixteenth embodiment of the invention. As shown in FIG. 33, the shaft 61C is provided with a narrow part, or a small diameter part 61N instead of a marked area. At the small diameter part 61N, the ring 65G is engaged. Note that the outer diameter of the ring 65G is slightly greater than the outer diameter of the shaft 61C so that the operator can feel the passage of the ring 65G through the slit 19a of the tap 19 (see FIG. 21) provided at the inlet 17 of the forceps channel 16. It should be further noted that the outer diameter of the ring 65G is smaller than the inner diameter of the forceps channel 16 so that the shaft 61C can move freely inside the forceps channel 16. The ring 56G may be formed from hard plastic or metal.

Figure 34:
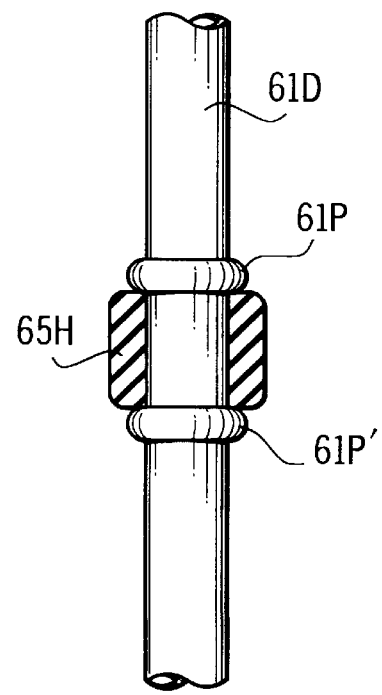
FIG. 34 shows a cross-section of a ring and a shaft of a treatment accessory according to a seventeenth embodiment of the invention.

FIG. 34 shows a ring 65H and a shaft 61D according to a seventeenth embodiment. As shown in FIG. 34, the shaft 61D is provided with a first protruded portion 61P and a second protruded portion 61P'. At an area between the first and second protruded portions 61P and 61P', the ring 65H is engaged. The outer diameter of the ring 65H as well as the outer diameter of the protruded portions 61P and 61P' are smaller than the inner diameter of the forceps channel 16. With this structure, when the ring 65H passes through the slit 19a of the tap 19, the operator can feel the resistance or click, and detect the position of the treatment device 62.

Figure 35:
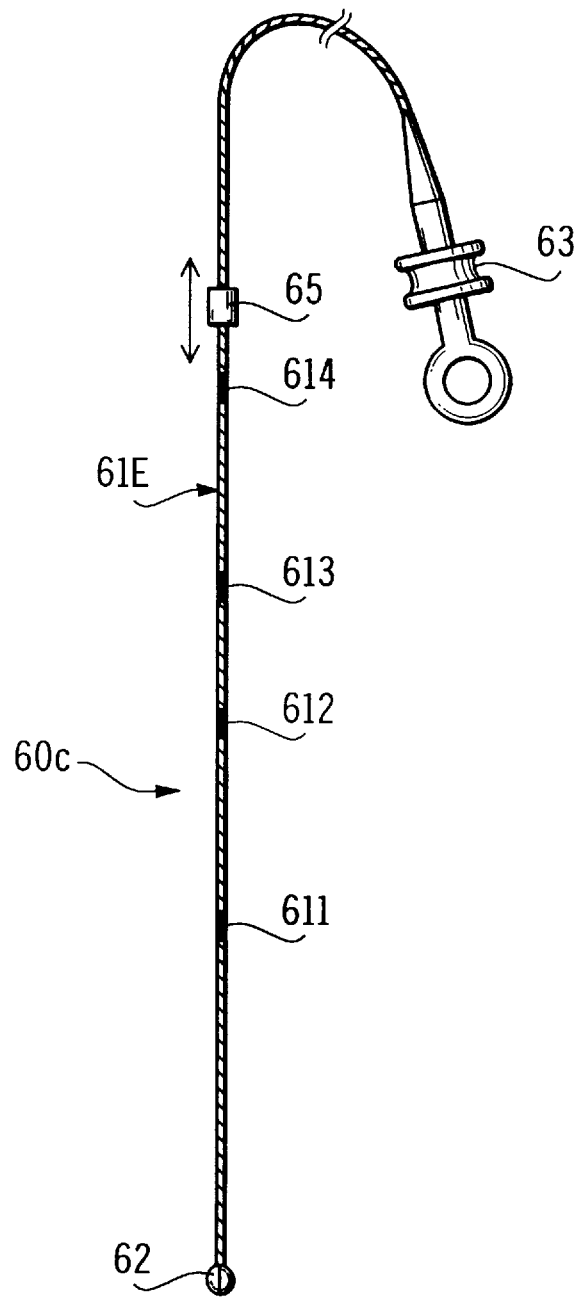
FIG. 35 shows a treatment accessory according to an eighteenth embodiment of the invention.

FIG. 35 shows a treatment accessory 60C according to an eighteenth embodiment of the invention.

The treatment accessory 60C is provided with first, second, third and fourth mark areas 611, 612, 613 and 614, similar to the treatment accessory 40 shown in FIG. 11. The mark areas 611, 612, 613 and 614 correspond to the endoscopes 10, 10A, 10B and 10C (shown in FIGS. 7 to 10). Specifically, the first mark area 611 corresponds to the endoscope 10; the second mark area 612 corresponds to the endoscope 10C; the third mark area 613 corresponds to the endoscope 10A; and the fourth mark area 614 corresponds to the endoscope 10B.

Figure 36:
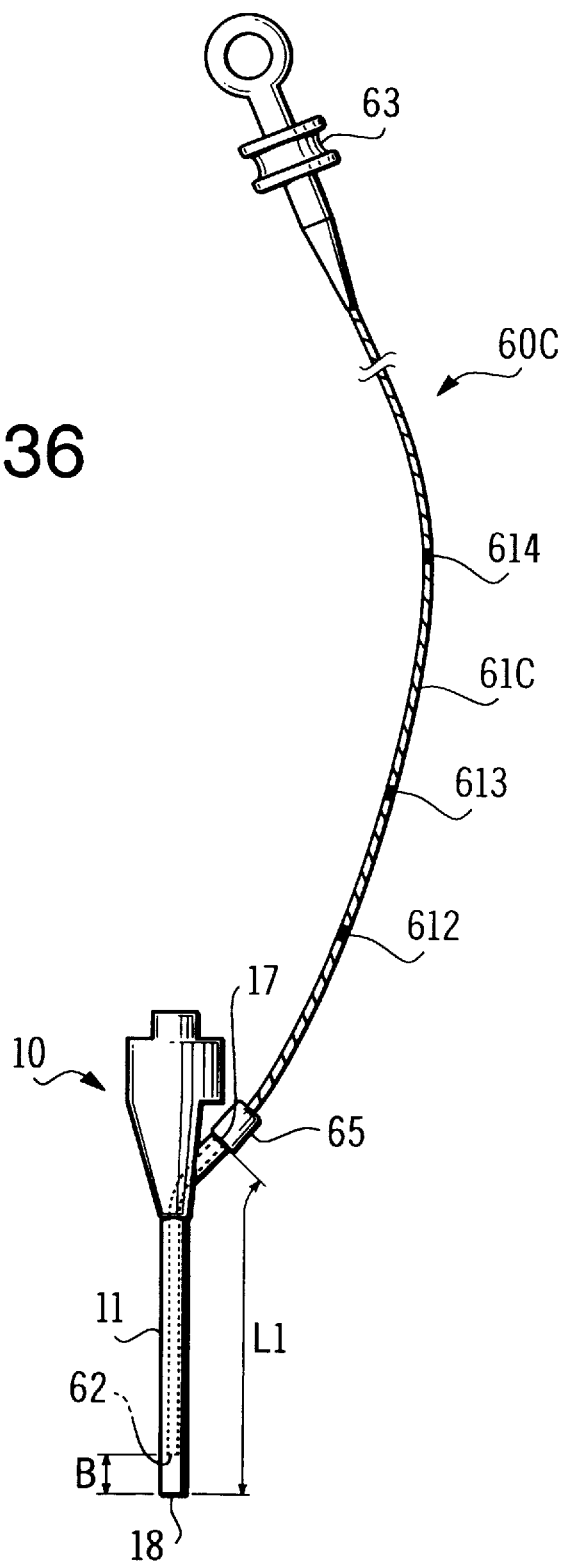
FIG. 36 shows the treatment accessory of FIG. 35 inserted in the endoscope of FIG. 7.

If the treatment accessory 60C is used for the endoscope 10 shown in FIG. 7, the slidable ring 65 is located at the first mark area 611. As the treatment accessory 60c is inserted in the forceps channel 16 of the endoscope 10 as shown in FIG. 36, the slidable ring 65 comes into contact with the inlet 17 of the forceps channel 16, and a resistance against the inserting force increases and is sensed by the operator. At this stage, the treatment device 62 is located at a position which is a distance B from the distal end of the insertion section 11 of the endoscope 10, for example, 1 to 10 cm (cf. FIG. 12). Even if the operator moves the treatment accessory 60C quickly, the operator can surely detect that the treatment device has reached a predetermined position inside the forceps channel 16, for example, before the treatment device 62 extends from the forceps channel 16. Thereafter, by further inserting, the operator can locate the treatment device 62 at a position extended from the outlet 18 of the forceps channel 16.

Figure 37:
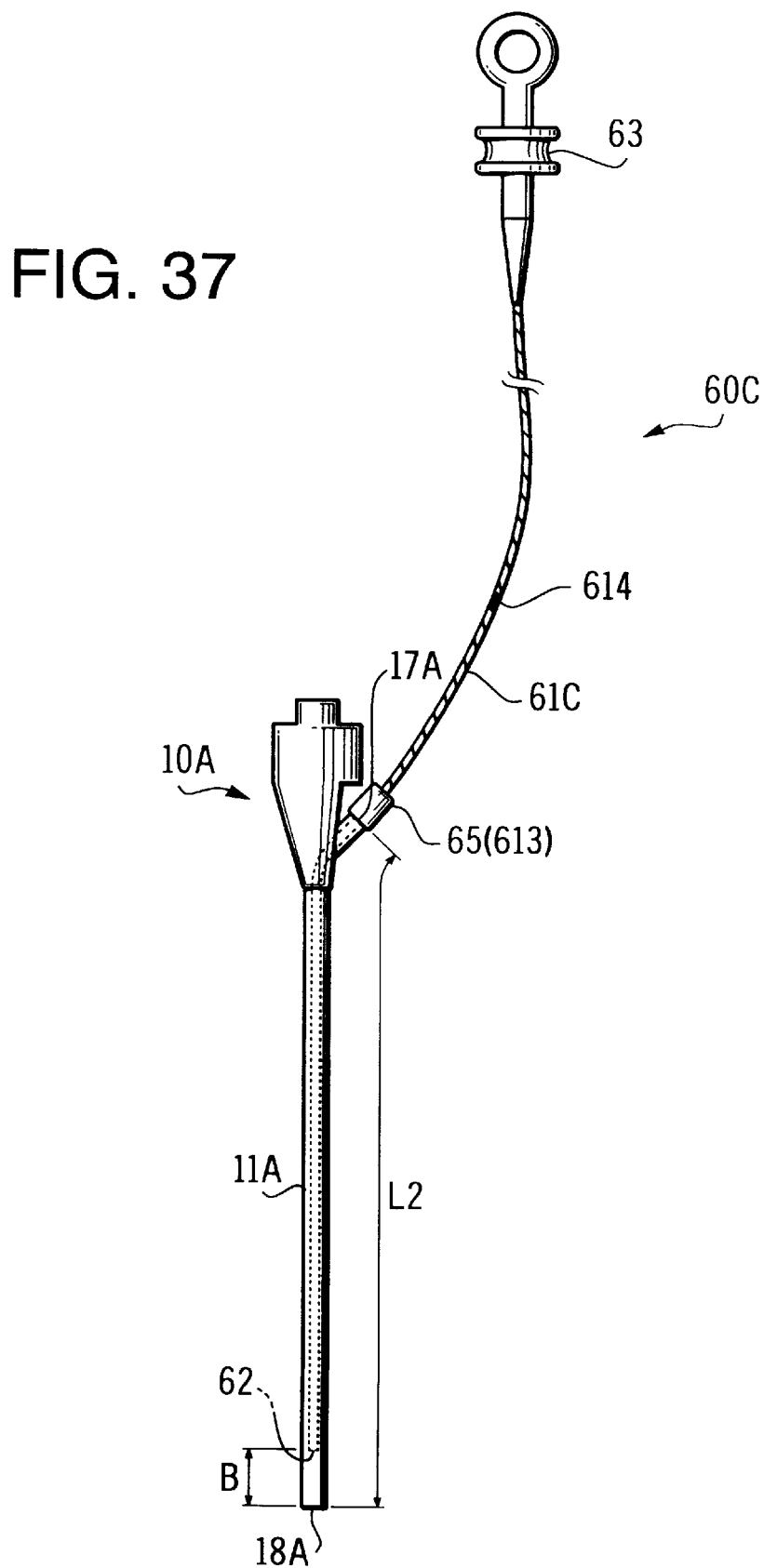
FIG. 37 shows the treatment accessory of FIG. 35 inserted in the endoscope of FIG. 8.

FIG. 37 shows the treatment accessory 60C being used in the second endoscope 10A. When the slidable ring 65 (located at the third mark 613) has come into contact with the inlet 17A, the treatment device 42 is located inside the forceps channel 16A at the distance B from the outlet 18A. Thus, the treatment accessory 60C can be quickly inserted in the forceps channel 16A and safely stopped before the treatment device 42 extends from the outlet 18A.

Figure 38:
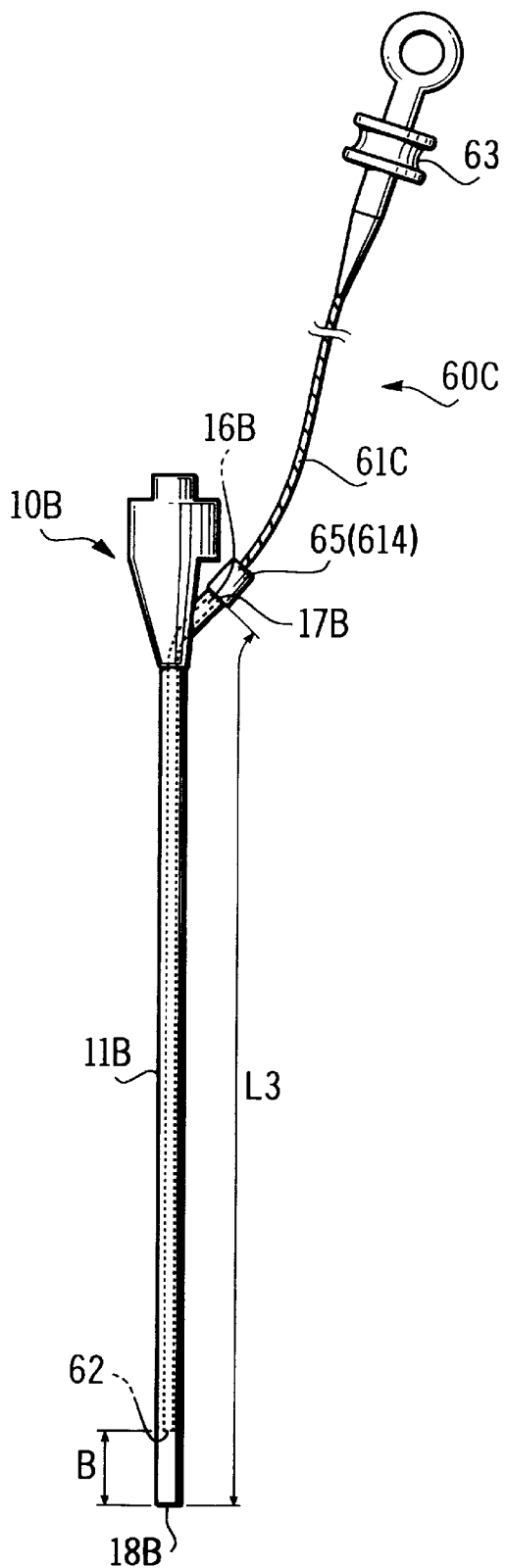
FIG. 38 shows the treatment accessory of FIG. 35 inserted in the endoscope of FIG. 9.

FIG. 38 shows the treatment accessory 60C being used in the third endoscope 10B. When the slidable ring 65 (located at the fourth mark 614) has come into contact with the inlet 17B, the operator senses increased resistance, and the treatment device 42 is located inside the forceps channel 16B at the distance B from the outlet 18B. Thus, the treatment accessory 60C can be quickly inserted in the forceps channel 16B and safely stopped before the treatment device 62 extends from the outlet 18B.

Similarly to the above, when the treatment accessory 60C is used for the fourth endoscope 10C, the slidable ring 65C is positioned at the second mark 612. When the slidable ring 65 comes into contact with the inlet 17C of the forceps channel 16C and the operator senses increased resistance, the treatment device 62 is located at the distance B from the distal end of the forceps channel 16C. Accordingly, the treatment accessory 60C can be quickly inserted in the forceps channel 16C and safely stopped before the treatment device 62 extends from the outlet 18C.

Similar to the embodiments described above, the first through fourth mark areas 611–614 are preferably formed to have colors or textures different from the other portions of the shaft 60C. Further, it is possible that the four marks 612–614 have different colors or textures from each other such that each mark indicates a type or purpose of the endoscope.

In any one of the above alternatives, it is advantageous if the inlet of the endoscope has the same color as the mark corresponding thereto.

According to the eighteenth embodiment, each of the marks corresponds to a position for locating the slidable ring 65 in order to indicate that the distal end of the treatment accessory has reached a predetermined position inside the forceps channel 16. Therefore, when the operator moves the treatment accessory quickly, he/she can stop inserting before the distal end of the treatment accessory extends from the distal end of the forceps channel whichever endoscope 10, 10A, 10B or 10C is used. Further, since the distance between the distal end of the forceps channel and the position where the treatment device is located when the slidable ring 65 has come into contact with the inlet 17 of the forceps channel 16 is relatively short, by further inserting the treatment accessory by a relatively small amount, e.g., by small pushes, the treatment device can be extended from the distal end of the forceps channel and may be located at an appropriate position. Therefore, the treatment accessory 60C can be used for various endoscopes and, in each endoscope, the treatment accessory 60C can be positioned quickly without a risk of damaging the tissue in a human cavity.

It should be noted that, in the present embodiment, four mark areas 611–614 are provided on the shaft. The number of the marks, however, is not limited to four, and could be any number greater than one. In other words, the number and positions of the mark areas should be determined in accordance with the number of types of endoscopes for which the treatment accessory is to be used.

Figure 39:
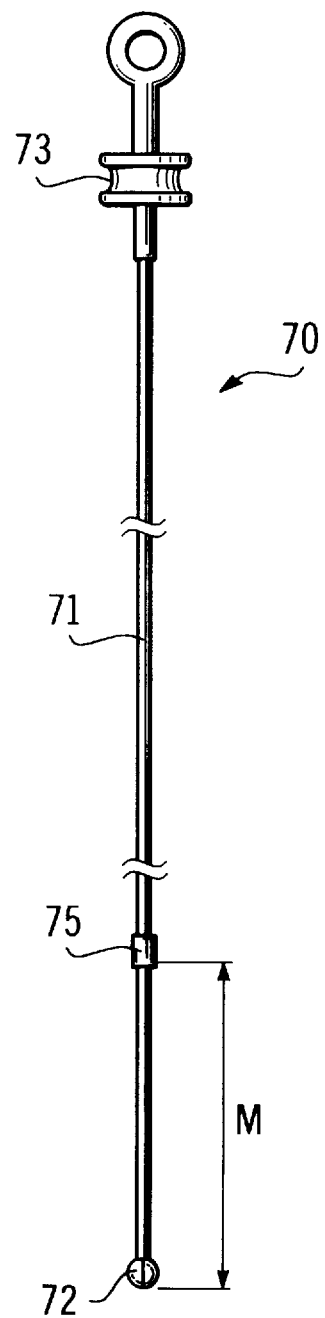
FIG. 39 shows a treatment accessory according to a nineteenth embodiment of the invention.

FIG. 39 shows a treatment accessory 70 according to a nineteenth embodiment of the invention.

The treatment accessory 70 includes a shaft 71, an operation unit 73 which is connected to the proximal end of the shaft 71, and a treatment device 72 which is provided at the distal end of the shaft 71. On the shaft, a ring 75 is fitted. The treatment accessory 70 is substantially similar to the treatment accessory 60 shown in FIG. 22, except that the ring 75 is initially located at the length M from the distal end of the treatment device 70 (cf. FIG. 15), and further the outer diameter of the ring 75 is smaller than the inner diameter of the forceps channel 16. The length M is greater than the length by which the treatment device 72 extends from the forceps channel 16 when the treatment accessory 70 is in normal use, so that the ring 75 stays inside the forceps channel when the treatment device 72 is operated.

The length M may be adjusted according to the use, i.e., a portion of a human cavity to which the treatment accessory 70 is to be used. For example, the length M may be set at approximately 30 cm if the treatment accessory 70 is used in an endoscope for inspection of a large intestine or the like, i.e., having a relatively long insertion section of approximately 150 cm. If the treatment accessory 70 is for an endoscope for bronchial inspection or the like, i.e., having a relatively short insertion section of approximately 50 cm, the length M may be set at approximately 10 cm.

Figure 40:
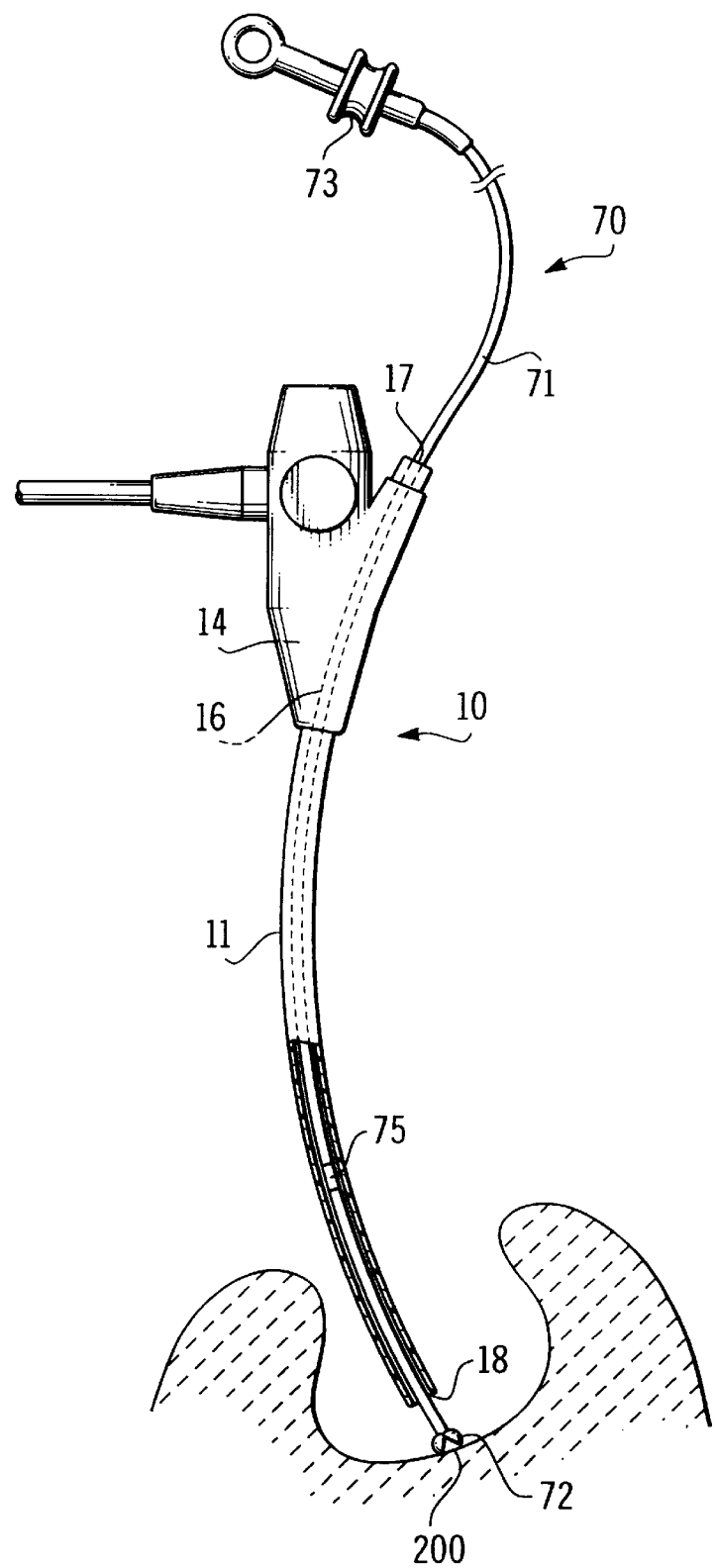
FIG. 40 shows the treatment accessory of FIG. 39 when inserted in a forceps channel of an endoscope.

FIG. 40 shows the treatment accessory 70 being inserted in a forceps channel 16 of an endoscope 10 in order to perform a treatment on an affected part 200 (cf. FIG. 17).

The treatment accessory 70 is inserted from the inlet 17 into the forceps channel 16. The treatment device 72 is extended from the outlet 18 of the insertion section 11, and press contacted onto the affected part 200. By operating the operating unit 73, the treatment device 72 is opened or closed and tissue at the affected part 200 is collected. At this stage, the ring 75 is located inside the forceps channel 16.

Figure 41:
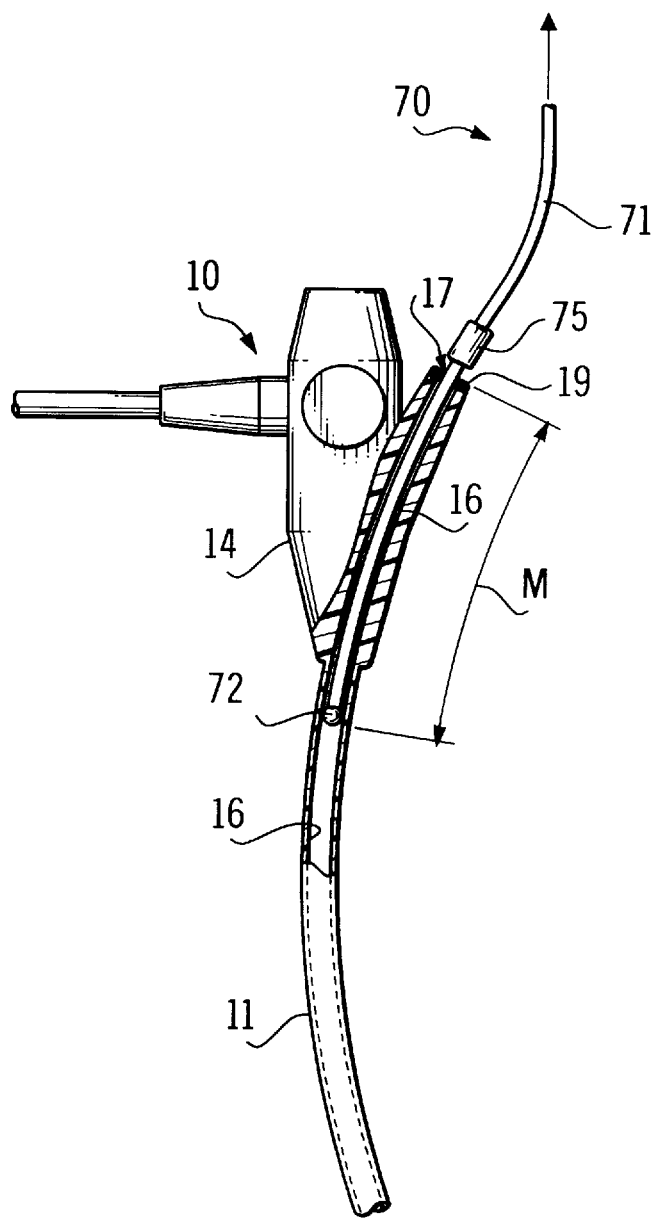
FIG. 41 shows the treatment accessory of FIG. 39 being removed from a forceps channel of an endoscope.

FIG. 41 shows the treatment accessory 70 being removed from the forceps channel 16. Specifically, FIG. 41 shows the state when the ring 75 has just been withdrawn from the forceps channel 16. In this state, an amount of the treatment accessory 70 equal to the length M remains inside the forceps channel 16. Accordingly, during removal of the treatment accessory 70, the operator can pull the treatment accessory 70 quickly until the ring 75 appears, after which, the shaft 51 may be pulled more slowly, such that the shaft 51 does not jump or whip upon exiting the forceps channel 16 and thus a loss of collected tissue, sprinkling of adhered fluid, or the like can be avoided.

Figure 42:
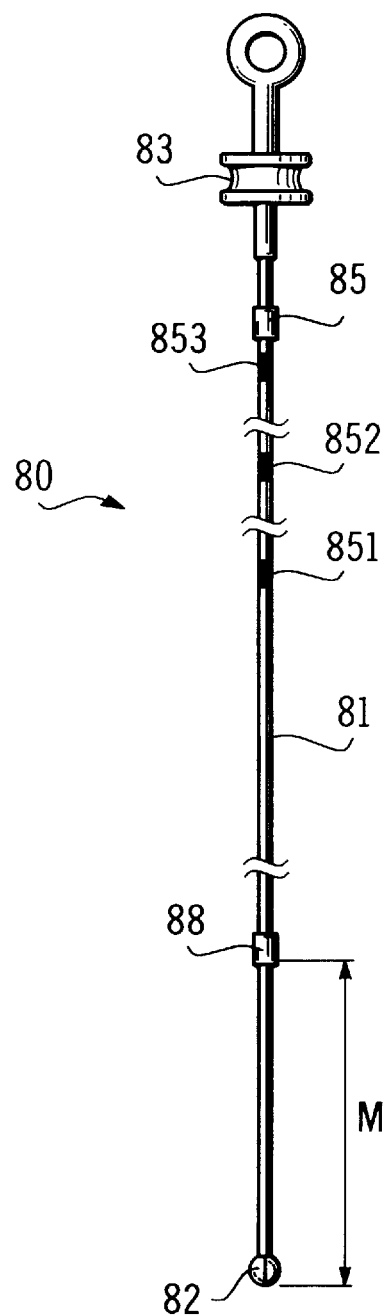
FIG. 42 shows a treatment accessory according to a twentieth embodiment of the invention.

FIG. 42 shows a treatment accessory 80 according to a twentieth embodiment of the invention.

The treatment accessory 80 is a combination of the treatment accessory 60C shown in FIG. 35 and the treatment accessory 70 shown in FIG. 39. The treatment accessory 80 is provided with a flexible shaft 81, a treatment device 82 provided at a distal end of the shaft 81, and an operation unit 83 is provided at the proximal end of the shaft 81. An operation wire (not shown) is slidably threaded inside the shaft, one end of the wire is connected to the treatment device 82 and the other end of the wire is connected to the operation unit 83.

On the shaft 81, a plurality of mark areas 851, 852, 853 are formed to indicate a position of a slidable ring 85, similar to the arrangement of the treatment accessory 61E shown in FIG. 35. Further, another ring 88 is provided at a position which is a distance M from the distal end of the treatment device 82, similar to the treatment accessory 70 shown in FIG. 39.

With this arrangement, when the treatment accessory 80 is inserted into the forceps channel 16 of the endoscope 10, the operator can appropriately stop the treatment accessory 80 before the treatment device 82 extends from the distal end of the forceps channel 16. Further, when the treatment accessory 80 is removed from the forceps channel, as the ring 88 passes through the slit 19a of the tap 19 provided at the inlet 17 of the endoscope, the operator detects that the treatment device 82 is approaching. Accordingly, the operator can control the removing speed of the treatment accessory 80.

Since there are a plurality of mark areas formed on the shaft 81, it may be advantageous that the plurality of mark areas are formed to have different colors or textures from each other so that the operator can distinguish the mark areas from each other.

Further, it should be noted that the treatment accessory 80 could be formed as various kinds of treatment accessories (i.e., perform various functions), such as a forceps instrument, a high frequency snare, and the like.

According to the eighth through twentieth embodiments, even if the operator does not watch the treatment accessory when it is being inserted or removed, the position of the treatment device can be recognized, and the operator can stop an inserting or removing operation at an appropriate time when the treatment apparatus is approaching the inlet or outlet of the forceps channel.

Figure 43:
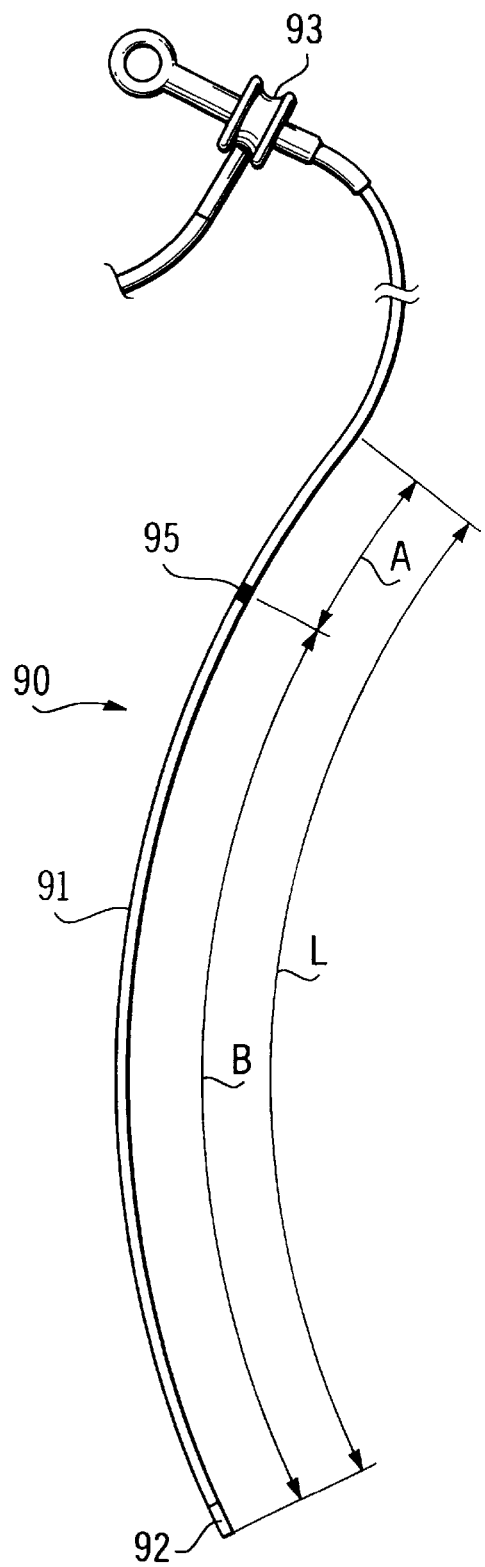
FIG. 43 shows a treatment accessory according to a twenty-first embodiment of the invention.

FIG. 43 shows a treatment accessory 90 according to a twenty-first embodiment of the invention.

The treatment accessory 90 includes a flexible shaft 91 made from, for example, tetrafluoraethylene. At the proximal end of the shaft 91, an operating unit 93 is provided. At the distal end of the shaft 91, a treatment device 92 is provided. In this embodiment, a high frequency snare is provided as the treatment device 92.

The treatment device 92 is used in the endoscope 10 as shown, for example, in FIG. 20. As described above, the tap 19, shown in FIG. 21, is attached at the inlet 17 of the forceps channel 16. The treatment device 92 is connected to the operation unit 93 by a wire (not shown) which is inserted through the shaft 91. On the shaft, at the length B from the distal end of the treatment device 92, a mark area 95 is formed.

Figure 44:
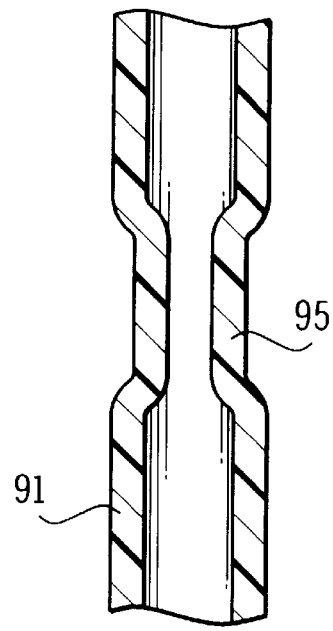
FIG. 44 shows a cross-section of a mark area and a shaft of the treatment accessory of FIG. 43.

FIG. 44 shows an enlarged cross-sectional view of the shaft 91, along its axis. As shown in FIG. 44, the mark area 95 has a smaller outer diameter with respect to the other portions of the shaft 91. Note that the mark area 95 is formed to be an evenly depressed portion at any circumferential portion thereof.

As the treatment instrument (the snare instrument) 90 is inserted in the forceps channel 16, when the mark area 95 passes through the slit 19a of the tap 19, the resistance changes, and accordingly the operator can feel the passage of the mark area 95 through the tap 19.

Similar to the embodiment shown in FIG. 1, the length B is shorter than the length L (see FIG. 20) of the forceps channel 16 such that B=L−A. Accordingly, when the distal end side of the mark area 95 has reached the tap 19, i.e., the inlet 17 of the forceps channel 16, the distal end of the treatment device 92 is located a length A from the distal end of the forceps channel 16.

Thus, the operator can know to stop inserting the treatment accessory 90 before the treatment device 92 extends from the outlet 18 of the forceps channel 16 even if the treatment accessory 90 is being inserted quickly. A further small movement of the shaft 91 then extends the treatment device 92 from the distal end of the forceps channel 16 appropriately.

Figure 45:
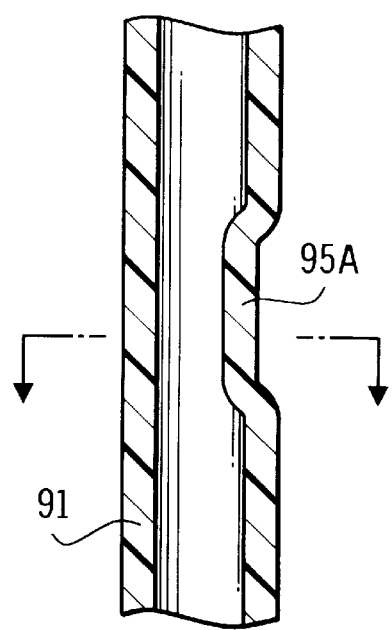
FIG. 45 shows a cross-section of a modified mark area and shaft of the treatment accessory of FIG. 43.
Figure 46:
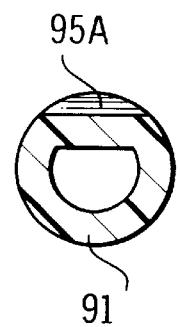
FIG. 46 shows an end cross-section of the mark area and shaft of FIG. 45.

FIGS. 45 and 46 show a modified mark area 95A. The mark area 95A is formed such that only a part of the circumferential area of the mark area 95 is formed to be depressed or cut out to form a flattened area.

Figure 47:
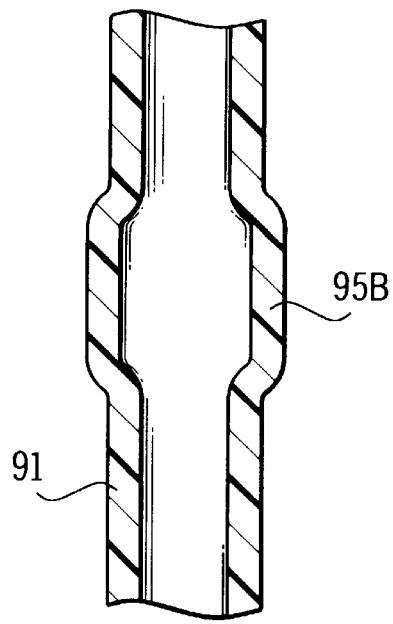
FIG. 47 shows a cross-section of another modified mark area and shaft of the treatment accessory of FIG. 43.

FIG. 47 shows another alternative mark area 95B. In this case, the mark area 95B is formed to have a larger diameter. The larger diameter may be formed by, for example, hot molding. Note that the inner diameter of the mark area 95B is also formed greater than the inner diameter of the other portions of the shaft 91.

Figure 48:
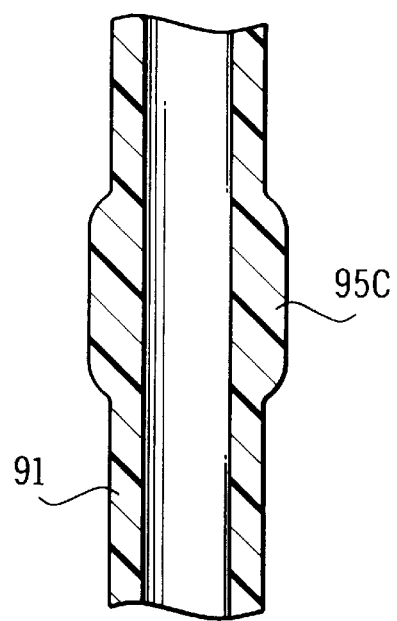
FIG. 48 shows a cross-section of yet another modified mark area and shaft of the treatment accessory of FIG. 43.

FIG. 48 shows a further alternative mark area 95C. The mark area 95C is similar to the mark area 95B, except that the inner diameter of the mark area 95C is the same as the inner diameter of the other portions of the shaft 91.

Figure 49:
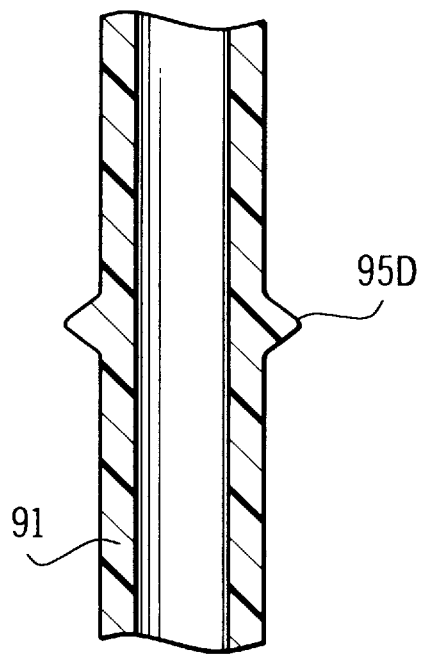
FIG. 49 shows a cross-section of yet another modified mark area and shaft of the treatment accessory of FIG. 43.

FIG. 49 shows yet a further alternative mark area 95D. The mark area 95D is formed to be a flange shape.

Figure 50:
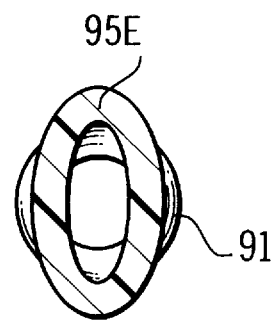
FIG. 50 shows an end cross-section of yet another modified mark area and shaft of the treatment accessory of FIG. 43.

FIG. 50 shows yet a further alternative mark area 95E. In this alternative, the mark area 95E is formed to be an oval-shape when viewed along the axis of the shaft 92. That is, the mark area 95E has a greater diameter in one direction, and smaller diameter in another direction, with respect to the diameter of the other portions of the shaft 91.

As described above, the operator can feel the change of resistance when the mark area passes through the slit 19a of the tap 19. Therefore, the operator can stop inserting the treatment accessory 90 securely before the treatment device 92 extends from the outlet 18 of the forceps channel 16.

Figure 51:
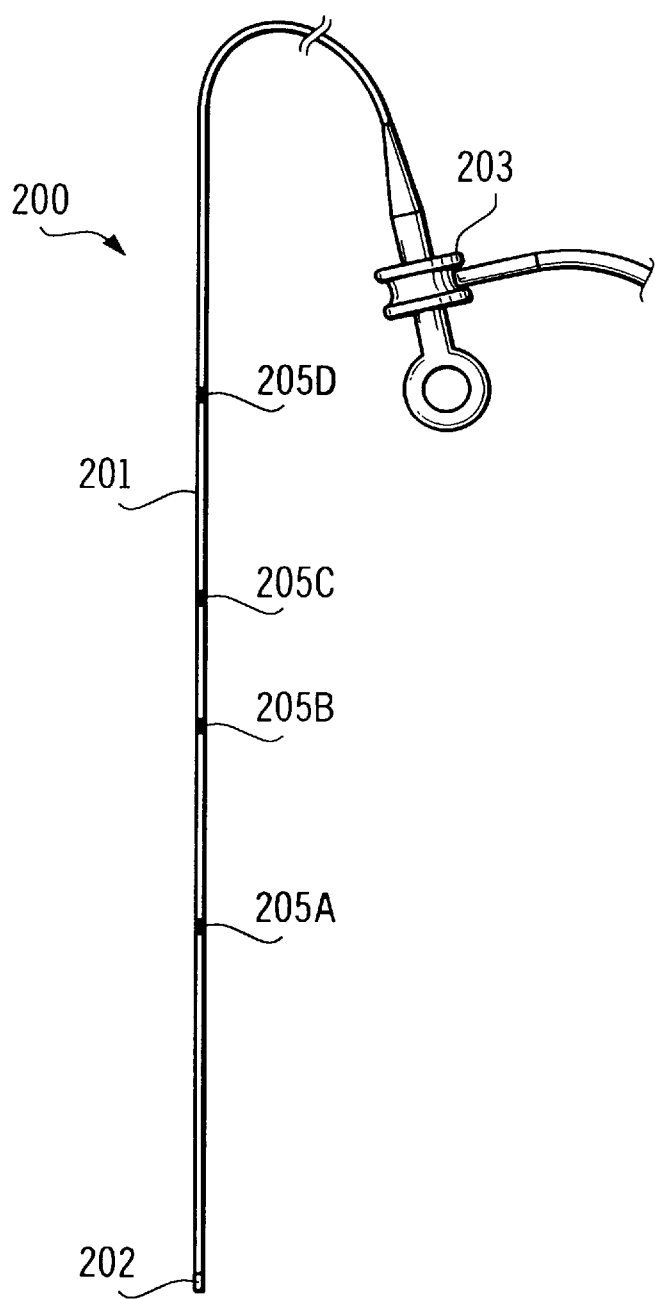
FIG. 51 shows a treatment accessory according to a twenty-second embodiment of the invention.

FIG. 51 shows a treatment accessory 200 according to a twenty-second embodiment of the invention. The treatment accessory 200 is used together with the tap 19, for the various endoscopes (first–fourth endoscopes 10, 10A, 10B and 10D) as shown in FIGS. 7–10.

The treatment accessory 200 includes a flexible shaft 201 made from synthetic resin such as tetrafluoraethylene. At the proximal end of the shaft 201, an operation unit 203. is provided, and at the distal end of the shaft 201, a treatment device 202 is provided. The treatment device 202 is remotely operated from the operation unit 201 by a wire (not shown) inserted inside the shaft 201.

On the shaft 201, four mark areas 205A, 205B, 205C and 205D are provided. The mark area 205A corresponds to the first endoscope 10 (see FIG. 7), the mark area 205B corresponds to the fourth endoscope 10C, the mark area 205C corresponds to the second endoscope 10A, and the mark area 205D corresponds to the third endoscope 10B. Each of the mark areas 205A, 205B, 205C and 205D is formed to have a shape similar to that of the twenty-first embodiment or its alternatives.

Figure 51A:
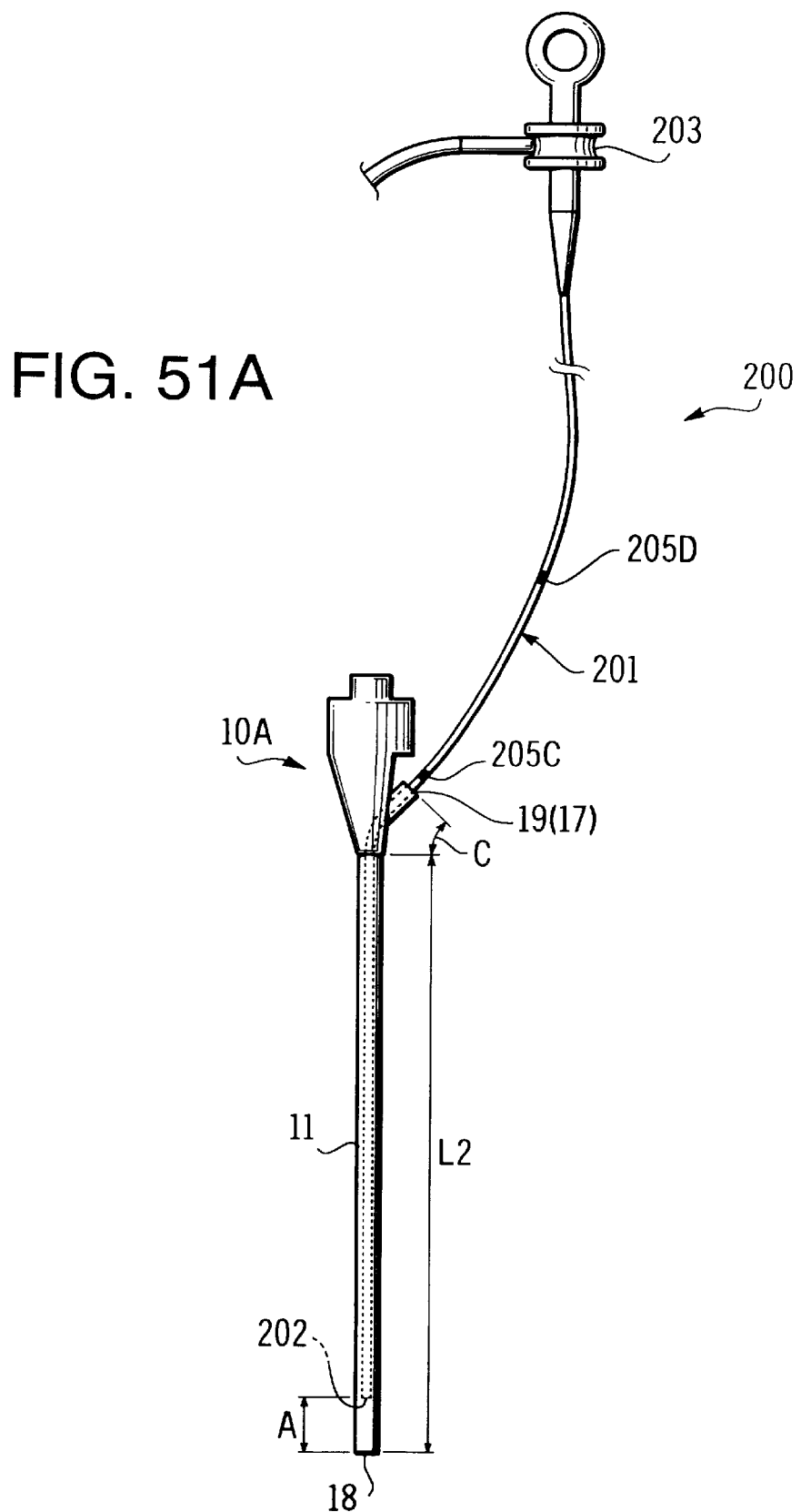
FIG. 51A shows the treatment accessory of FIG. 51 inserted in a forceps channel of an endoscope.

As shown in FIG. 51A, as an example, when the mark areas 205A, 205B, 205C and 205D pass the tap 19 of the endoscopes 10, 10C, 10A and 10B, respectively, the treatment device 202 is located, inside the forceps channel, a length A from the distal end of the outlet 18, wherein A is 1 through 10 cm.

With use of the treatment accessory 200, a single treatment accessory can be used for various types of endoscopes, or endoscopes having various lengths of forceps channels, and in any case, the operator can stop inserting the treatment accessory before the treatment device extends from the distal end of the forceps channel.

Figure 52:
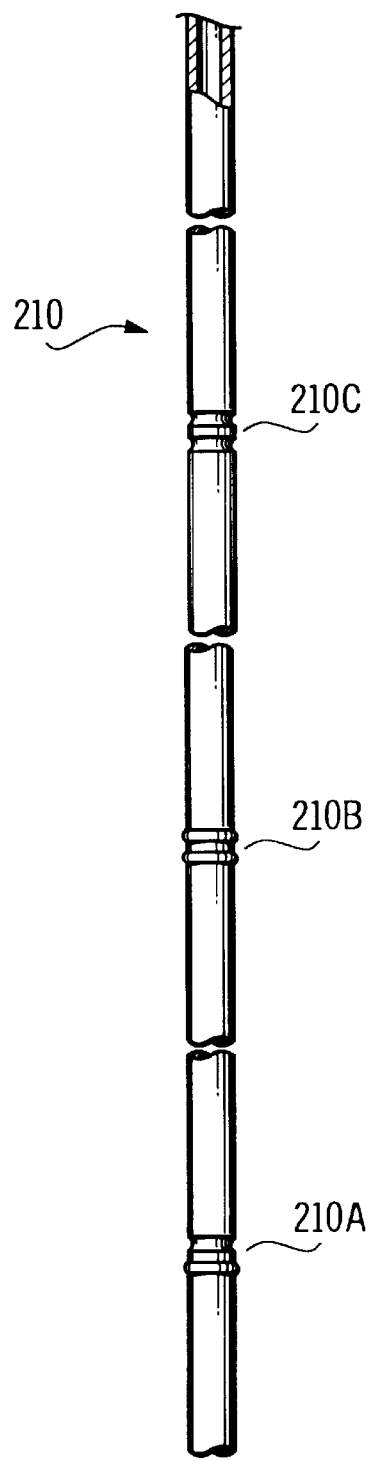
FIG. 52 shows a shaft of a treatment accessory according to a twenty-third embodiment of the invention.

The mark areas 205A–205D could be formed to have the same shape, or alternatively, as shown in FIG. 52 as a twenty-third embodiment, the mark areas could be formed to have different shapes 210A, 210B, 210C or the like. In the twenty-third embodiment, the mark area 210A has a smaller diameter portion and a greater diameter portion with respect to the diameter of the non-mark areas of the shaft 210; the mark area 210B has two greater diameter portions; and the mark area 210C has two smaller diameter portions. Any other combination of various shapes would also be applicable as long as the operator is able to feel the difference when the respective mark area passes through the slit 19a.

Figure 53:
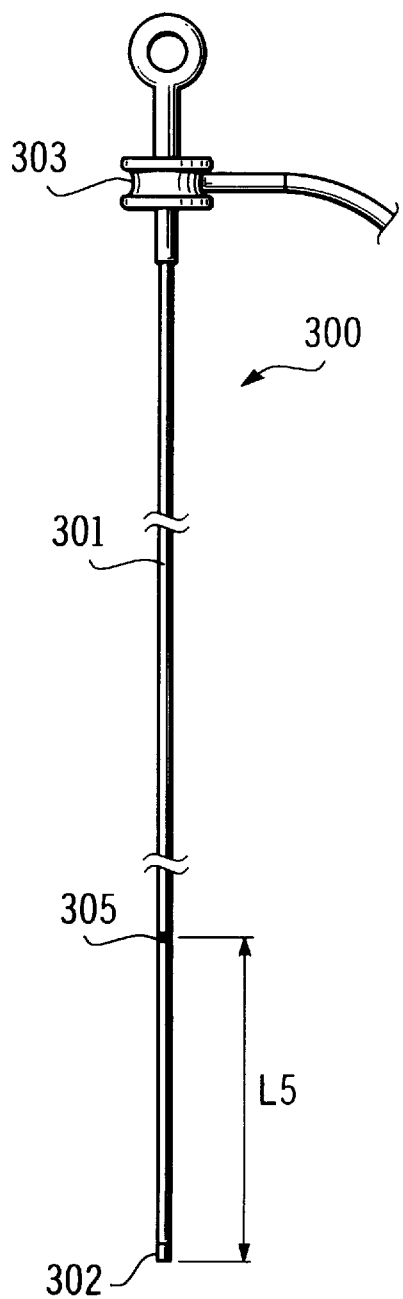
FIG. 53 shows a treatment accessory according to a twenty-fourth embodiment of the invention.

FIG. 53 shows a treatment accessory 300 according to a twenty-fourth embodiment. The treatment accessory 300 includes a flexible shaft 301 made of synthetic resin such as tetrafluoraethylene, or a closely wound wire. A treatment device 302 is provided at the distal end of the shaft 301.

The proximal end of the shaft 301 is connected to an operation unit 303 used for remotely operating the treatment device 302 by a wire (not shown) inserted through the shaft 301.

A mark area 305 is formed on the shaft 301 at a length L5 from the distal end of the treatment device 302. The mark area 305 has a similar shape to the mark area 95 described above, or its alternative.

The length L5 may be adjusted according to the use, i.e., a portion of a human cavity to which the treatment accessory 300 is to be used. For example, the length L5 may be set at approximately 30 cm if the treatment accessory 300 is used in an endoscope for inspection of a large intestine or the like, i.e., having a relatively long insertion section of approximately 150 cm. If the treatment accessory is for an endoscope for bronchial inspection or the like, i.e., having a relatively short insertion section of approximately 300 cm, the length L5 may be set at approximately 10 cm.

In any case, the length L5 is preferably set greater than the amount by which the treatment device 302 extends from the end of the forceps channel 16 when the treatment accessory 300 is used normally such that the mark area 305 remains inside the forceps channel 16 during use of the treatment accessory 300. This is in contrast to some conventional treatment accessories that are provided with graduated marks at the distal end of the shaft in order to measure the amount that a treatment accessory extends beyond an outlet of the forceps channel.

Figure 54:
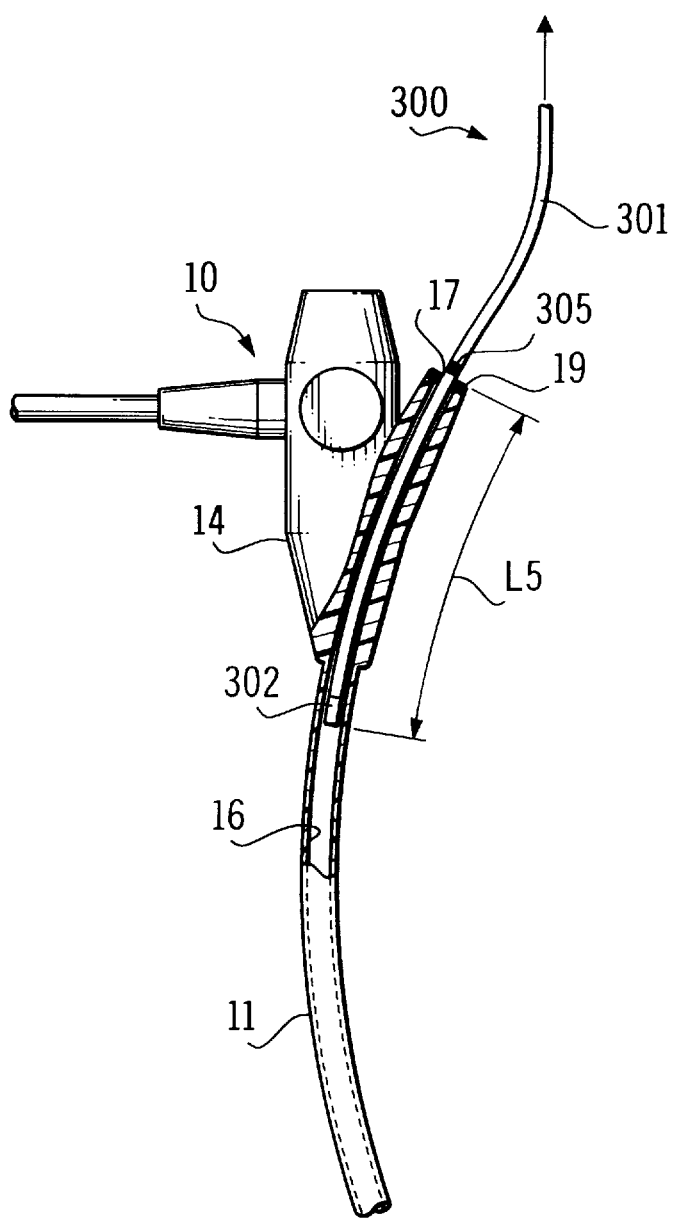
FIG. 54 shows the treatment accessory of FIG. 53 being removed from a forceps channel of an endoscope.

FIG. 54 shows the treatment accessory 300 being removed from the forceps channel 16. Specifically, FIG. 54 shows the state when the mark area 305 has just appeared from the forceps channel 16. In this state, an amount of the treatment accessory 300 equal to the length L5 remains inside the forceps channel 16. Accordingly, during removal of the treatment accessory 300, the operator can pull the treatment accessory quickly until the mark area 305 appears, after which, the shaft 301 may be pulled more slowly, such that the shaft 301 does not jump or whip upon exiting the forceps channel 16 and thus a loss of collected tissue, sprinkling of adhered fluid, and the like can be avoided.

Figure 55:
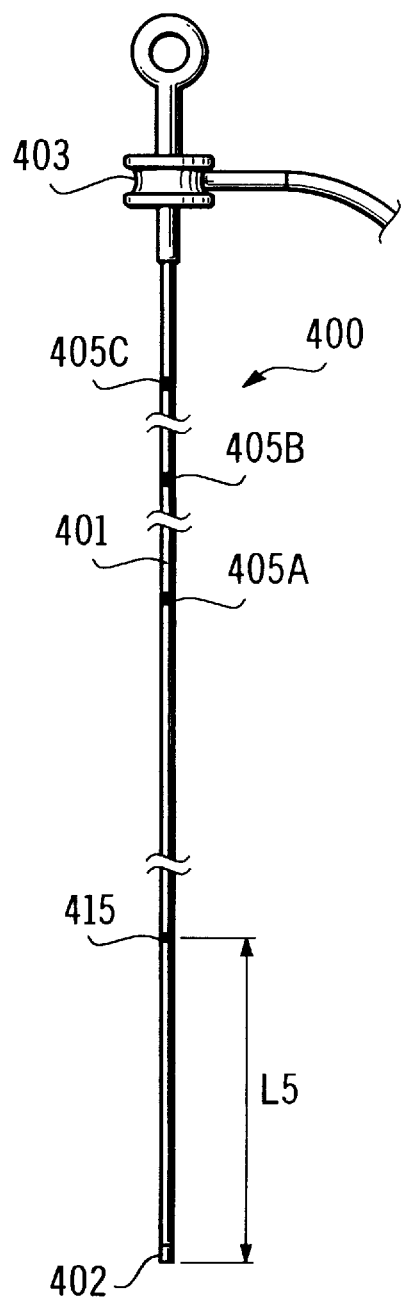
FIG. 55 shows a treatment accessory according to a twenty-fifth embodiment of the invention.

FIG. 55 shows a treatment accessory 400 according to a twenty-fifth embodiment of the invention.

The treatment accessory 400 is a combination of the treatment accessory 200 shown in FIG. 51 and the treatment accessory 300 shown in FIG. 53. The treatment accessory 400 is provided with Ma flexible shaft 401, a treatment device 402 provided at the distal end of the shaft 401, and an operation unit 403 provided at the proximal end of the shaft 401. An operation wire (not shown) is slidably threaded inside the shaft, one end of the wire is connected to the treatment device 402 and the other end of the wire is connected to the operation unit 403.

On the shaft 401, a plurality of mark areas 405A, 405B, 405C are formed, similar to the arrangement of the treatment accessory 200 shown in FIG. 51. Further, another mark area 415 is formed at a length L5 from the distal end of the treatment device 402, similar to the treatment accessory 300 shown in FIG. 53. The mark areas are similar to the mark area 90 or its alternatives.

With this arrangement, when the treatment accessory 400 is inserted into the forceps channel 16 of the endoscope 10, the operator can stop inserting the treatment accessory 400 before the treatment device 402 extends from the distal end of the forceps channel 16. Further, when the treatment accessory 400 is removed from the forceps channel 16, the operator detects that the treatment device 402 is approaching the inlet 17 when the mark area 415 appears out of the forceps channel 16. Accordingly, the operator can control the removing speed of the treatment accessory 400.

A treatment accessory 500 according to a twenty-sixth embodiment is now described. In use, the treatment accessory 500 is inserted into the endoscope 10 shown in, for example, FIGS. 1 and 3. As described above, the endoscope 10 includes an insertion section 11 that has a flexible, tubular form and the proximal end thereof is connected to a manipulating part 14. The forceps channel 16 is formed through the manipulation part 14 and the insertion section and has a length that is defined as the FC length L.

Also, as described above, the inlet 17 of the forceps channel 16 is provided with the forceps plug 19 (see, for example, FIG. 21), that prevents any air that is fed into the body cavity via the forceps channel 16 from spurting out. The forceps plug 19 is formed, for example, from a resilient, rubber plate with a slit 19a formed therein. The slit 19a closes around an inserted treatment accessory due to resilience. When the treatment accessory is drawn out, the forceps plug 19 closes completely. Depending on the type of endoscope, the forceps plug 19 may not be necessary.

Figure 56:
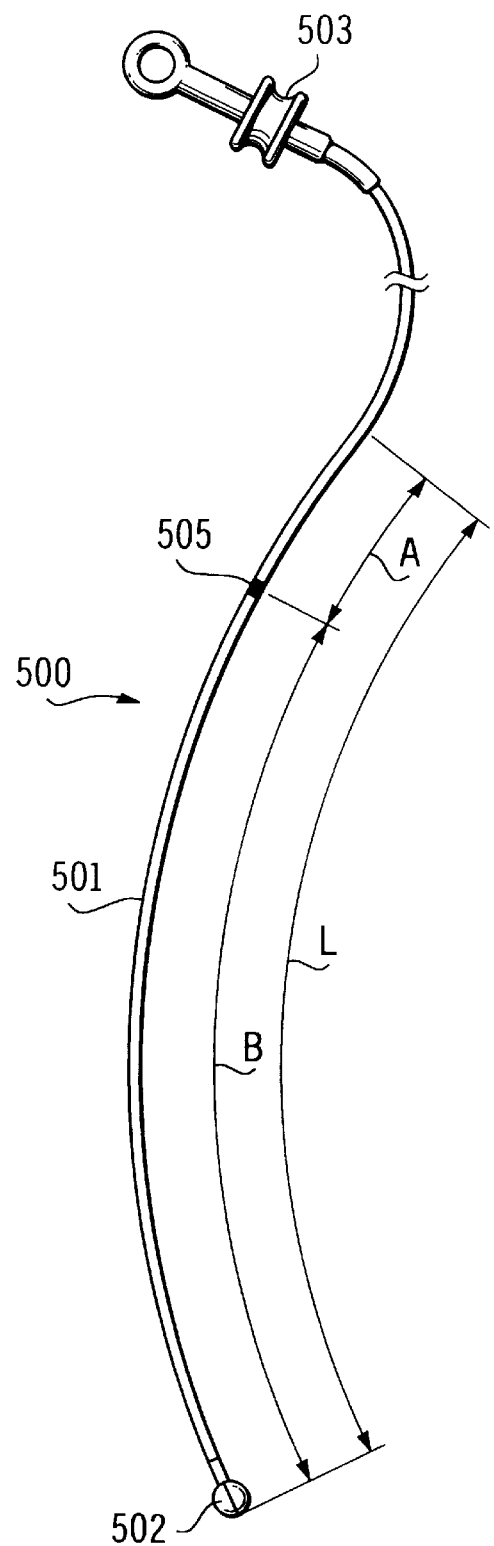
FIG. 56 shows a treatment accessory according to a twenty-sixth embodiment of the invention.

FIG. 56 shows the treatment accessory 500 according to the twenty-sixth embodiment. In this embodiment, the treatment accessory 500 is, for example, a biopsy forceps, and includes a treatment device 502 (in this example, forceps), a shaft 501, and an operating part 503. The shaft 501 connects the operating part 503 and the treatment device 502 and is formed, for example, of a flexible, closely-wound coil formed by winding stainless steel wire in a spiral of uniform diameter.

Figure 57:
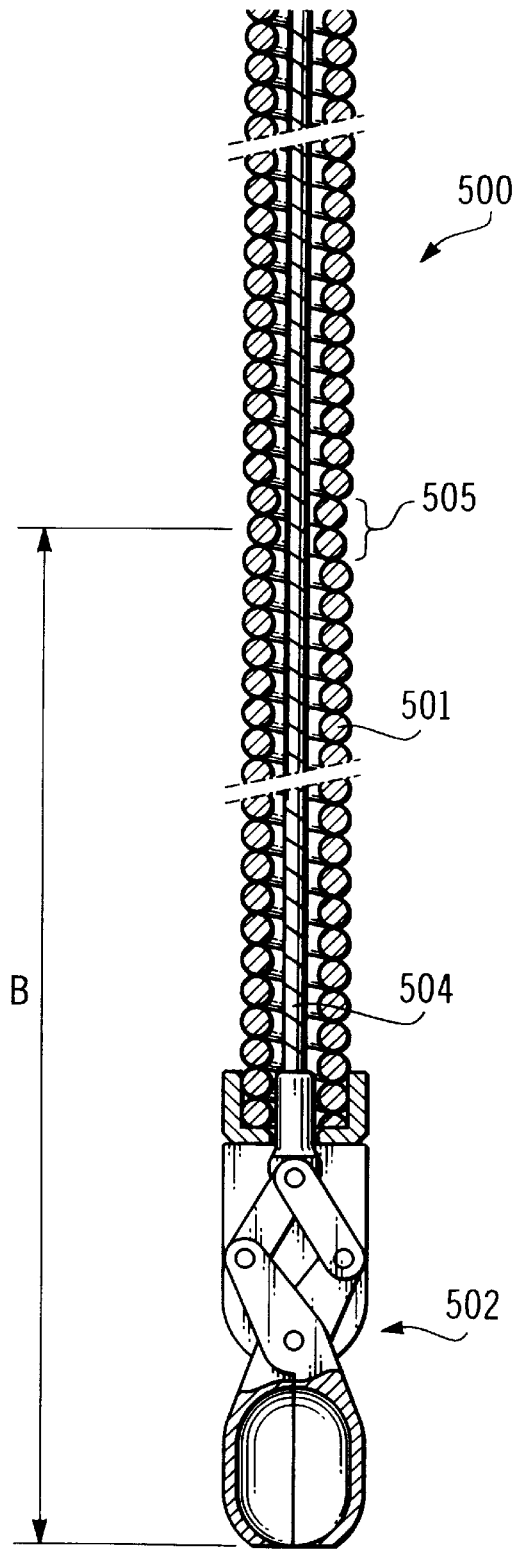
FIG. 57 shows a cross-section of a shaft of the treatment accessory of FIG. 56.

The treatment device 502 and part of the shaft 501 is inserted into the forceps channel 16 of the endoscope 10, and the treatment device 502 may be remotely manipulated via a manipulating wire 504 (shown in FIG. 57) inserted through the shaft 501.

A marked portion 505 is formed on the shaft 501 a distance B from the distal end thereof. As can be seen in the enlarged cross section of FIG. 57, the marked portion 505 is formed by making the shaft 501 smaller in diameter, for example, by making the winding diameter of the shaft 501 at this part thinner than the winding diameter of parts to the front and rear during, in this case, two turns.

In this embodiment, when the marked portion 505 of the shaft 501 passes through the forceps plug 19 in the process of inserting or removing the treatment accessory 500 from the forceps channel 16, the resistance against the insertion or removal of the shaft 501 that is received by the forceps plug 19 changes, thereby enabling the operator to detect that the marked portion 505 is passing through the forceps plug 19 due to the sensation transmitted to the operator's hand.

As shown in FIG. 56, the distance B between the marked portion 505 and the distal end of the treatment accessory 500 (that is, the distal end of the treatment device 502) is set to be about 1 cm to 20 cm shorter than the FC length L of the forceps channel 16.

Thus, when the treatment accessory 500 is inserted through the forceps channel 16 of the endoscope 10 and the front end portion of the marked portion 505 reaches the proximal inlet 17 of the forceps channel 16, the treatment device 502 will be a distance A (A=L−B) from the outlet 18 of the forceps channel 16.

Thus, the operator may tactually detect that the marked portion 505 has passed through forceps plug 19 and stop the insertion of the treatment accessory 500 into the forceps channel 16 at that point. That is, the treatment accessory 500 can be stopped before the treatment device 502 protrudes from the outlet 18 even if inserted quickly. The treatment device 502 can then be protruded from the outlet 18 slowly and precisely.

Figure 58:
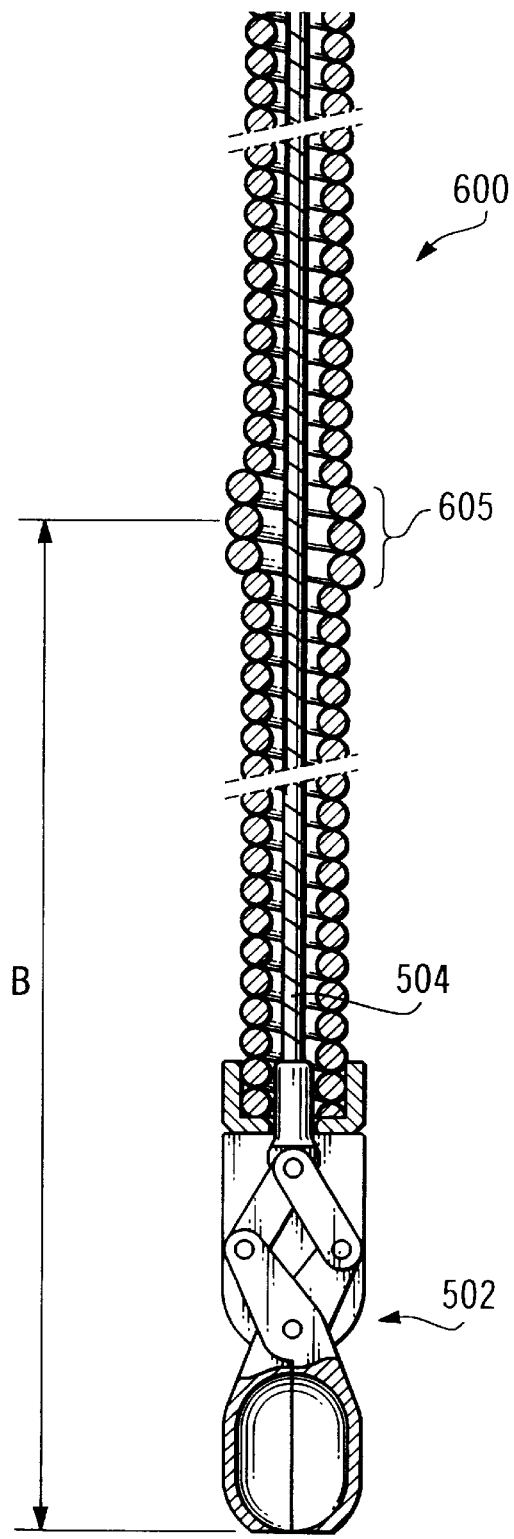
FIG. 58 shows a cross-section of a shaft of a treatment accessory according to a twenty-seventh embodiment of the invention.

FIG. 58 shows a treatment accessory 600 according to the twenty-seventh embodiment of the present invention. Here, a shaft 601 is provided with a marked portion 605, that has a larger outside dimension than the shaft 601, for example, by winding the shaft 601 at a winding diameter that is thicker for, for example, three turns, at the appropriate position a length B from the distal end of the treatment accessory 600.

Similar to the previous embodiment, by providing the marked portion 605, the resistance against insertion and removal of the shaft 601 from the forceps plug 19 will change when the marked portion 605 passes through the forceps plug 19, thereby enabling the operator to detect, through the sensation transmitted to the hand, that the marked portion 605 has passed through the forceps plug 19.

Figure 59:
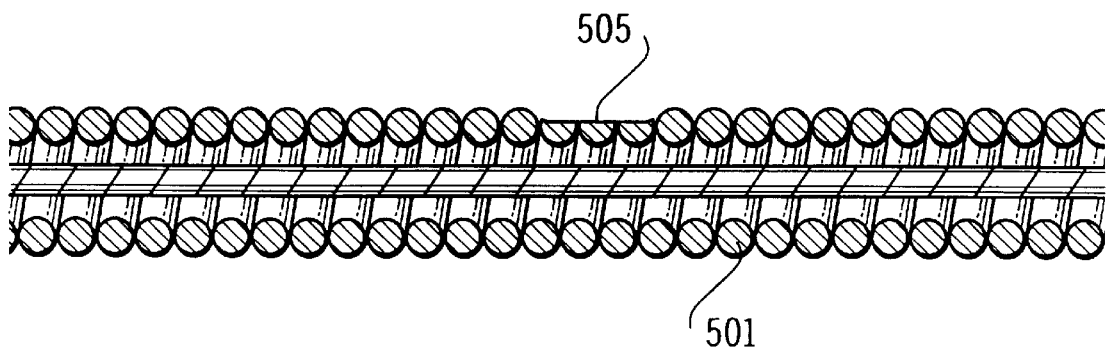
FIG. 59 shows a cross-section of an alternative of a shaft of the treatment accessory of FIG. 56.
Figure 60:
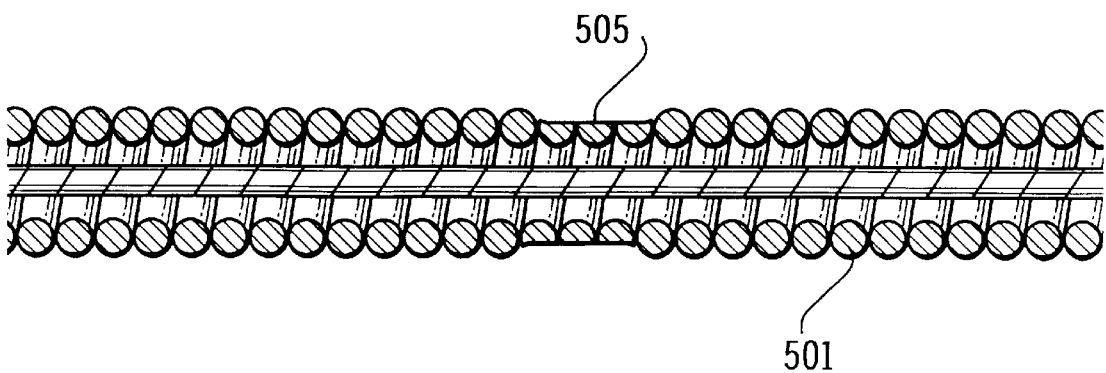
FIG. 60 shows a cross-section of another alternative of a shaft of the treatment accessory of FIG. 56.

The marked portion 505 may also be formed, for example, by grinding the surface of the shaft 501 in planar form, as shown in FIG. 59, or by grinding the surface of the shaft 501 as shown in FIG. 60.

Figure 61:
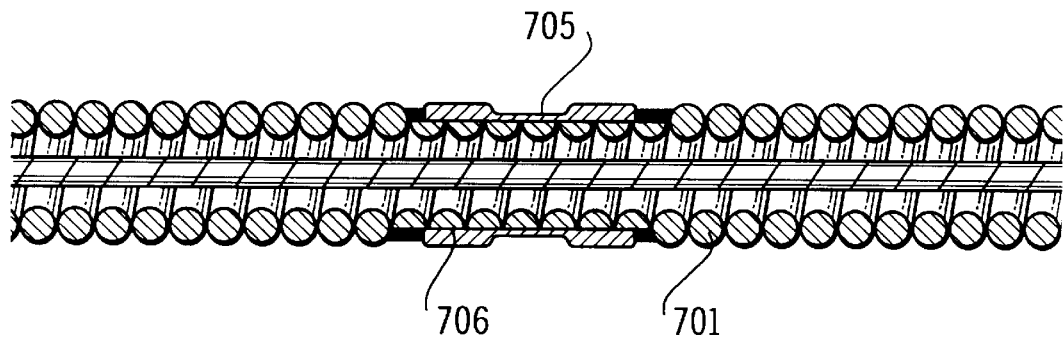
FIG. 61 shows a cross-section of a shaft of a treatment accessory according to a twenty-eighth embodiment of the invention.

As shown in FIG. 61, a treatment instrument 700 according to a twenty-eighth embodiment is provided with a connector 706 for connecting two tubes to form a shaft 701. A marked portion 705 can be formed on the outer peripheral surface of the connector 706. The connector 706 may be fixed to the shaft 701 by, for example, brazing, soldering, spot welding, or the like.

Figure 62:
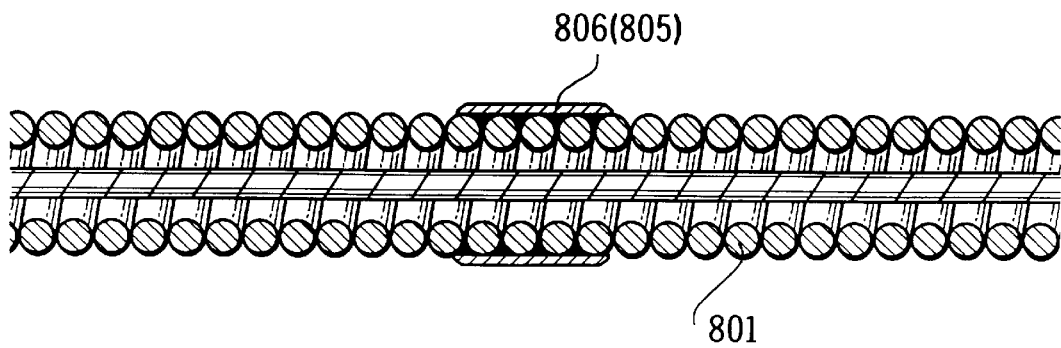
FIG. 62 shows a cross-section of a shaft of a treatment accessory according to a twenty-ninth embodiment of the invention.

Also, as shown in FIG. 62, in a twenty-ninth embodiment, a treatment accessory 800 is provided with a connector 806, that has a greater outside dimension than the shaft 801 for connecting two tubes to form the shaft 801. In this embodiment, the connecting pipe 806 serves as a marked portion 805 to allow the operator to detect the position of the treatment accessory 800. In this case, preferably the ends of the connecting pipe 806 are chamfered.

Figure 63:
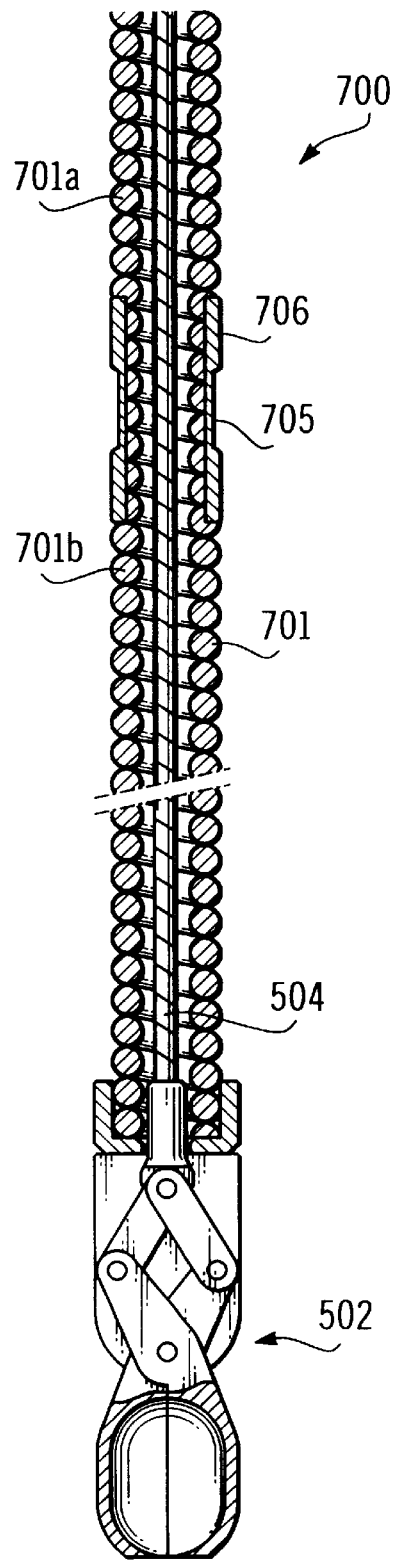
FIG. 63 shows a cross-section of a particular arrangement of a shaft of the treatment accessory of FIG. 61.

As shown in FIG. 63, in a case in which a shaft 701 is formed from a first closely-wound coil 701a and a second closely-wound coil 701b formed from wire having a smaller diameter than the second closely-wound coil 701a, it is preferable to use the connector 706 to connect the coils 701a, 701b. That is, it is preferable to form the marked portion 705 as an indent (i.e., having a smaller outside dimension).

Figure 64:
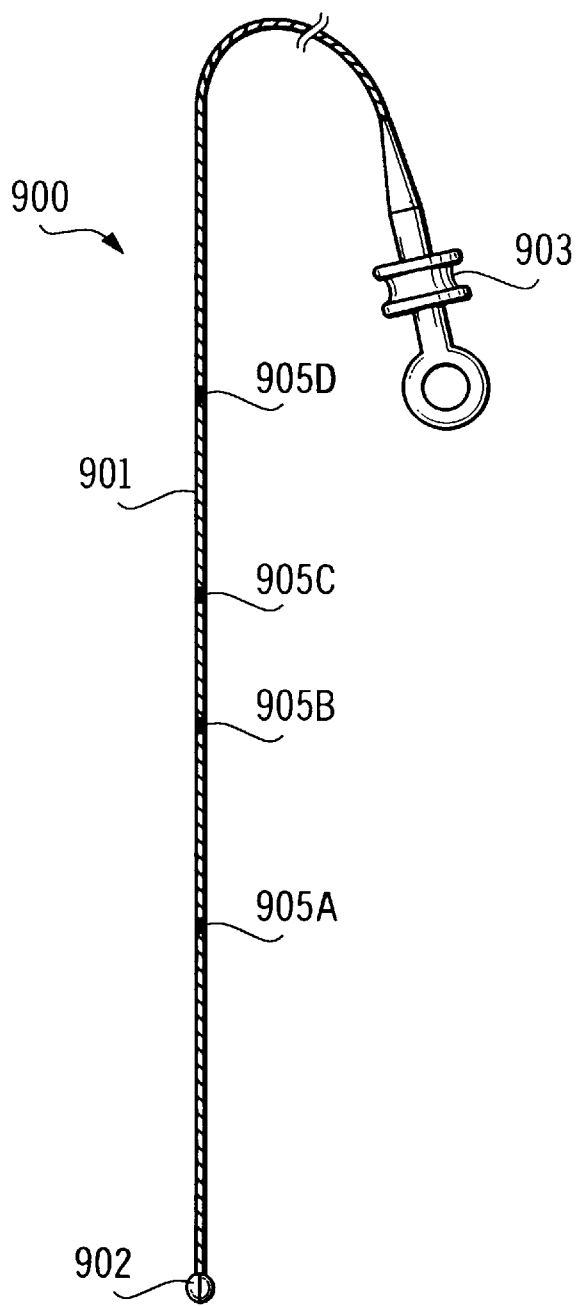
FIG. 64 shows a treatment accessory according to a thirtieth embodiment of the invention.

FIG. 64 shows a treatment accessory 900 according to a thirtieth embodiment of the invention. The treatment accessory 900 is used together with the forceps tap 19, for various endoscopes (first–fourth endoscopes 10, 10A, 10B and 10D) as shown in FIGS. 7–10.

The treatment accessory 900 includes a flexible shaft 901 made from a synthetic resin, such as tetrafluoraethylene or the like. At the proximal end of the shaft 901, an operation unit 903 is provided, and at the distal end of the shaft 901, a treatment device 902 is provided. The treatment device 902 is remotely operated by the operation unit 903 by a wire (not shown) inserted inside the shaft 901.

On the shaft 901, four mark areas 905A, 905B, 905C and 905D are provided. The mark area 905A corresponds to the first endoscope 10 (see FIG. 7); the mark area 905B corresponds to the fourth endoscope 10C, the mark area 905C corresponds to the second endoscope 10A, and the mark area 905D corresponds to the third endoscope 10B. Each of the mark areas 905A, 905B, 905C and 905D is formed to have a shape similar to one of the twenty-sixth embodiment through twenty-ninth embodiments and alternatives.

Similar to the description for the twenty-second embodiment above, when the mark areas 905A, 905B, 905C and 905D pass the forceps tap 19 of the endoscopes 10, 10C, 10A and 10B, respectively, the treatment device 902 is located, inside the forceps channel, a predetermined length from the distal end of the outlet 18, wherein the predetermined length may be set at, for example, between 1 to 10 cm.

With use of the treatment accessory 900, a single treatment accessory can be used for various types of endoscopes, or endoscopes having various lengths of forceps channels, and in any case, the operator can stop inserting the treatment accessory before the treatment device extends from the distal end of the forceps channel.

Figure 65:
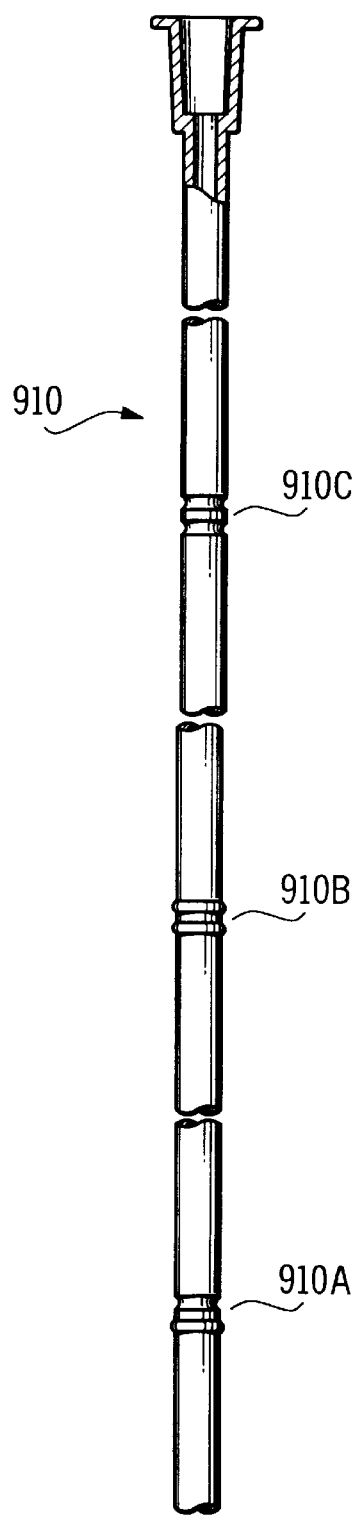
FIG. 65 shows a shaft of a treatment accessory according to a thirty-first embodiment of the invention.

The mark areas 905A–905D could be formed to have the same shape. Alternatively, as shown in FIG. 65, as a thirty-first embodiment, the mark areas could be formed to have different shapes 910A, 910B, 910C or the like. In the thirty-first embodiment, the mark area 910A has a small diameter portion and large diameter portion with respect to the diameter of the non-mark area of the shaft 910; the mark area 910B has two large diameter portions; and the mark area 910C has two small diameter portions. Other combinations of various shapes would also be applicable as long as the operator can feel a difference when the mark area passes through the slit 19a.

Figure 66:
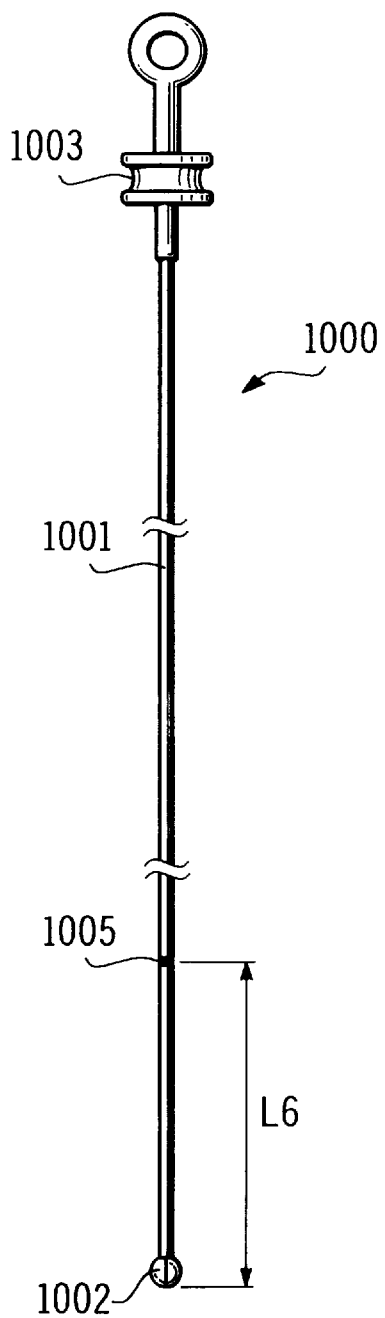
FIG. 66 shows a treatment accessory according to a thirty-second embodiment of the invention.

FIG. 66 shows a treatment accessory 1000 according to a thirty-second embodiment. The treatment accessory 1000 includes a flexible shaft 1001 made of, for example, a synthetic resin such as tetrafluoraethylene, or a closely wound wire. A treatment device 1002 is provided at the distal end of the shaft 1001.

The proximal end of the shaft 1001 is connected to an operation unit 1003 for remotely operating the treatment device 1002, by a wire (not shown) inserted through the shaft 1001.

A mark area 1005 is formed on the shaft 1001 a length L6 from the distal end of the treatment device 302. The mark area 1005 may be formed to have a shape similar to one of the twenty-sixth embodiment through twenty-ninth embodiments and alternatives.

The length L6 may be adjusted according to the use, i.e., depending on which portion of a human cavity in which the treatment accessory 1000 is to be used. For example, the length L6 may be set at approximately 30 cm if the treatment accessory 1000 is used in an endoscope for inspection of a large intestine or the like, i.e., an endoscope having a relatively long insertion section of approximately 150 cm. If the treatment accessory is for an endoscope for bronchial inspection or the like, i.e., an endoscope having a relatively short insertion section of approximately 300 cm, the length L5 may be set to, approximately 10 cm.

In any case, the length L6 is preferably set greater than the amount by which the treatment device 1002 extends from the end of the forceps channel 16 when the treatment accessory 1000 is used normally such that the mark area 1005 remains inside the forceps channel 16 during use of the treatment accessory 1000. This is in contrast to some conventional treatment accessories that are provided with graduation marks at the distal end of the shaft in order to measure the amount that a treatment accessory extends beyond an outlet of the forceps channel.

Figure 67:
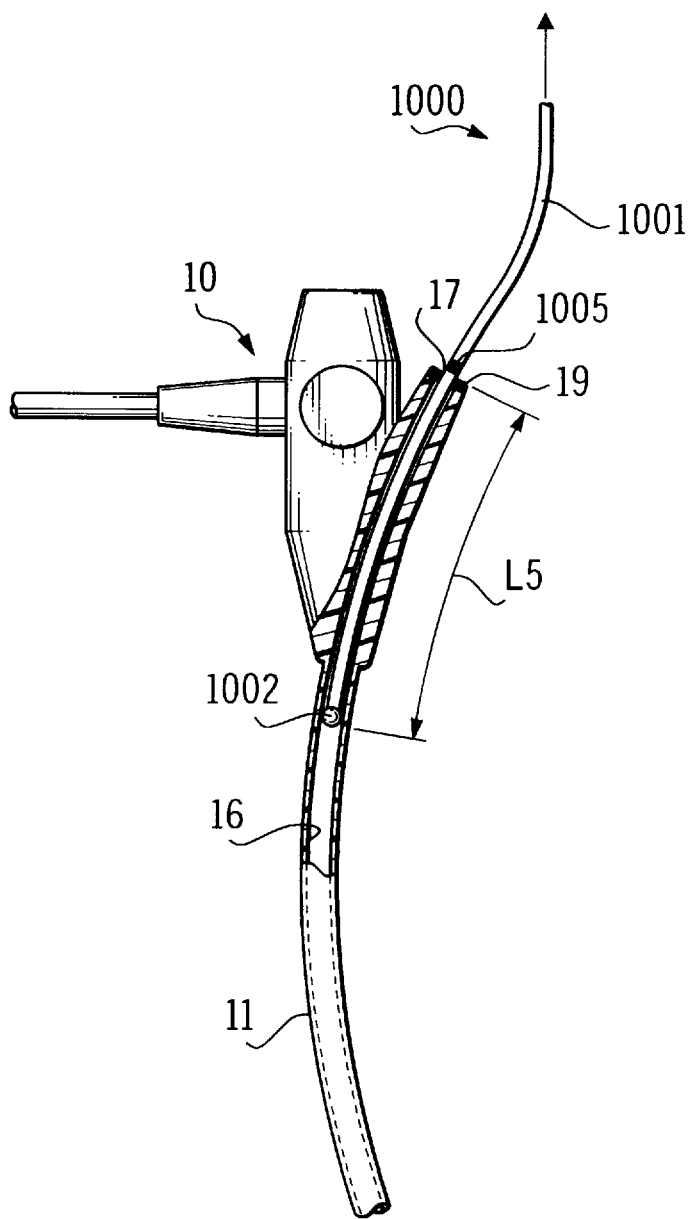
FIG. 67 shows the treatment accessory of FIG. 66 being removed from a forceps channel of an endoscope.

FIG. 67 shows the treatment accessory 1000 being removed from the forceps channel 16. Specifically, FIG. 67 shows the state when the mark area 1005 has just appeared from the forceps channel 16. In this state, an amount of the treatment accessory 1000 equal to the length L6 remains inside the forceps channel 16. Accordingly, during removal of the treatment accessory 1000, the operator can pull the treatment accessory quickly until the mark area 1005 appears, after which, the shaft 1001 may be pulled more slowly, such that the shaft 1001 does not jump or whip upon exiting the forceps channel 16 and thus a loss of collected tissue, sprinkling of adhered fluid, and the like can be avoided.

Figure 68:
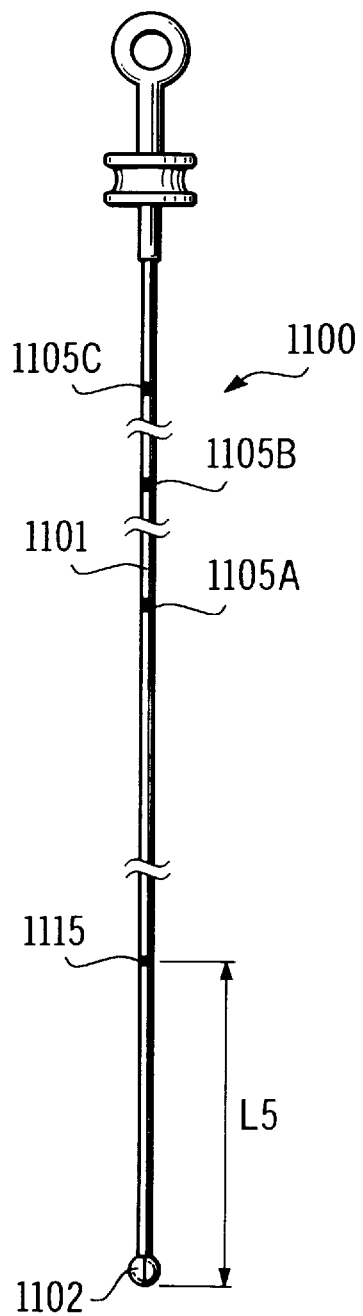
FIG. 68 shows a treatment accessory according to a thirty-third embodiment of the invention.

FIG. 68 shows a treatment accessory 1100 according to a thirty-third embodiment of the invention.

The treatment accessory 1100 is a combination of the treatment accessory 900 shown in FIG. 64 and the treatment accessory 1000 shown in FIG. 66. The treatment accessory 1100 is provided with a flexible shaft 1101, a treatment device 1102 provided at the distal end of the shaft 1101, and an operation unit 1103 provided at the proximal end of the shaft 1101. An operation wire (not shown) is slidably threaded inside the shaft connecting the treatment device 1102 to the operation unit 1103.

On the shaft 1101, a plurality of mark areas 1105A, 1105B, 1105C are formed, similar to the arrangement of the treatment accessory 900 shown in FIG. 64. Further, another mark area 1115 is formed a length L5 from the distal end of the treatment device 1102, which is similar to the treatment accessory 1000 shown in FIG. 66. The mark areas 1105A, 1105B, 1105C, and 1115 may be formed to have a shape similar to one of the twenty-sixth embodiment through twenty-ninth embodiments and alternatives.

With this arrangement, when the treatment accessory 1100 is inserted into the forceps channel 16 of the endoscope 10, the operator can stop inserting the treatment accessory 1100 before the treatment device 1102 extends from the distal end of the forceps channel 16. Further, when the treatment accessory 1100 is removed from the forceps channel 16, the operator recognizes that the treatment device 1102 is approaching when the mark area 1115 appears out of the forceps channel 16. Accordingly, the operator can also control the removal of the treatment accessory 1100.

In this case, it is preferable to form the mark areas 1105A, 1105B, 1105C, and 1115 differently so that there will be differences in the sensation transmitted to the hand.

Figure 69:
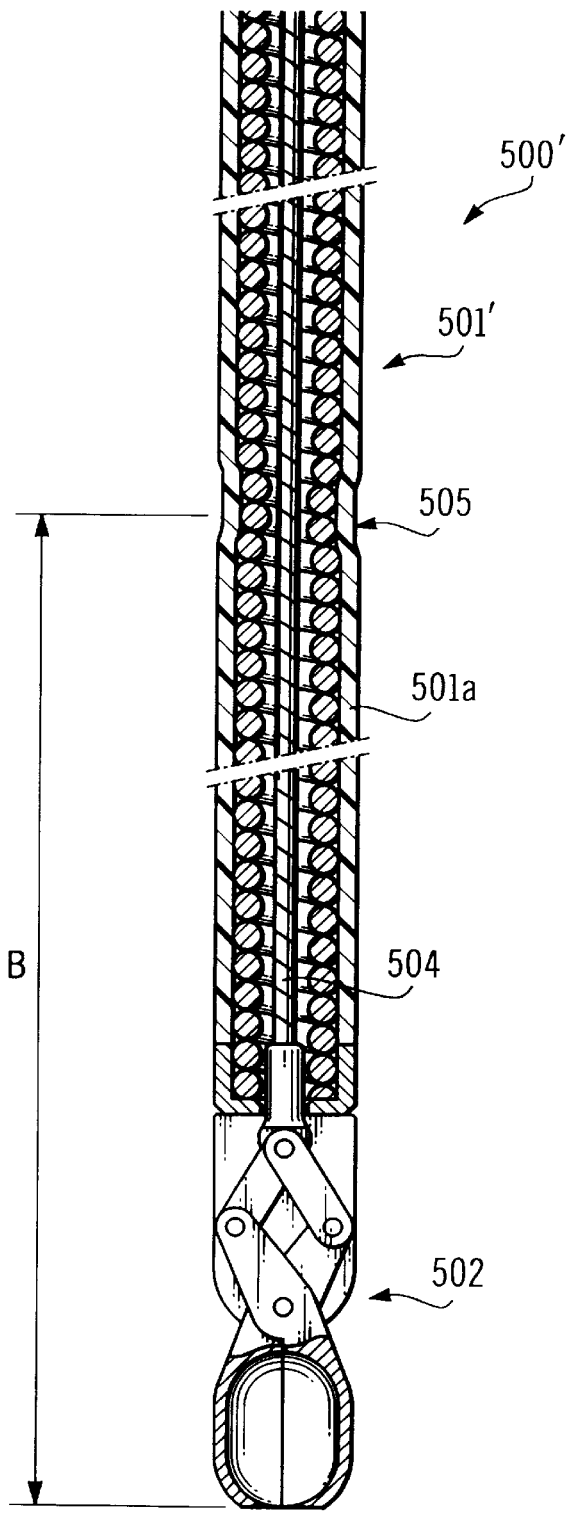
FIG. 69 shows an alternative arrangement of the treatment accessory of FIG. 57.
Figure 70:
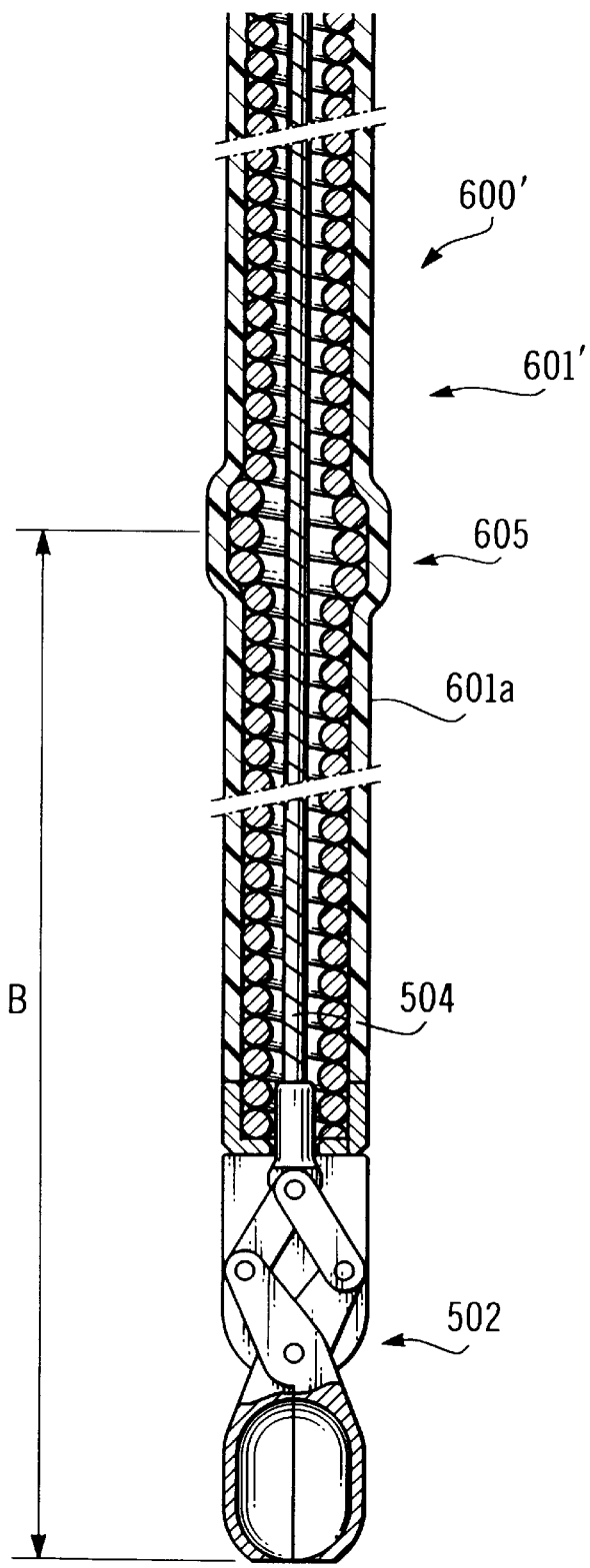
FIG. 70 shows an alternative arrangement of the treatment accessory of FIG. 58.

FIGS. 69 and 70 show modifications of the treatment accessories 500 and 600 of the twenty-sixth and twenty-seventh embodiments, respectively. These modifications apply to a high-frequency biopsy forceps in which a high-frequency current passes through the treatment instrument via the manipulating wire.

In this case, the surface of the shaft 501', 601' is covered along its entire length by an electrical insulating tube 501a, 601a. As shown in FIGS. 69 and 70, the change in the outside dimension of the closely-wound coil of the shaft 501', 601' also affects the outside dimension of the tube 501a, 601a.

A treatment accessory 1200 according to a thirty-fourth embodiment is now described. In use, the treatment accessory 1200 is inserted into the endoscope 10 shown in, for example, FIGS. 1 and 3. As described above, the endoscope 10 includes an insertion section 11 that has a flexible, tubular form and the proximal end thereof is connected to a manipulating part 14. The forceps channel 16 is formed through the manipulation part 14 and the insertion section and has a length that is defined as the FC length L.

Also, as described above, the inlet 17 of the forceps channel 16 is provided with the forceps plug 19 (see, for example, FIG. 21), that prevents any air that is fed into the body cavity via the forceps channel 16 from spurting out. The forceps plug 19 is formed, for example, from a resilient, rubber plate with a slit 19a formed therein. The slit 19a closes around an inserted treatment accessory due to resilience. When the treatment accessory is drawn out, the forceps plug 19 closes completely. Depending on the type of endoscope, the forceps plug 19 may not be necessary.

Figure 71:
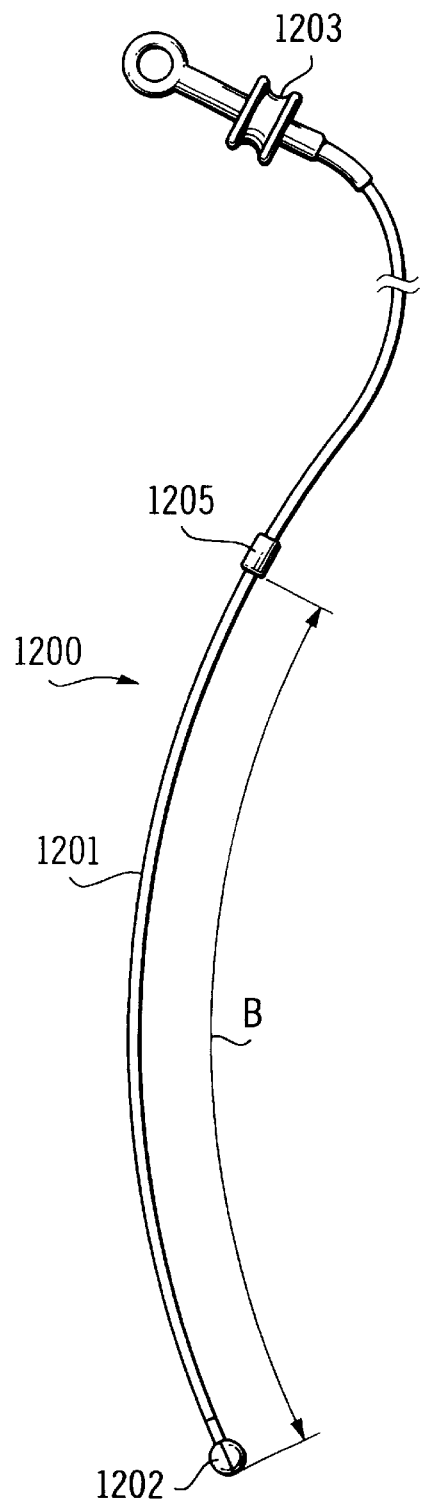
FIG. 71 shows a treatment accessory according to a thirty-fourth embodiment of the invention.

FIG. 71 shows the treatment accessory 1200 according to the thirty-fourth embodiment. In this embodiment, the treatment accessory 1200 is, for example, a biopsy forceps, and includes a treatment device 1202 (in this example, forceps), a shaft 1201, and operating part 1203. The shaft 1201 connects the operating part 1203 and the treatment device 1202 and is formed, for example, of a flexible, closely-wound coil formed by winding stainless steel wire in a spiral of uniform diameter.

The treatment device 1202 and part of the shaft 1201 is inserted into the forceps channel 16 of the endoscope 10, and the treatment device 1202 may be remotely manipulated via a manipulating wire 1204 (shown in FIG. 72) inserted through the shaft 1201.

An indication member 1205 is provided on the shaft 1201 a distance B from the distal end thereof. The distance B is less than the FC length L. The distance B is set to be about 1 cm to 20 cm shorter than the FC length L of the forceps channel 16.

The indication member 1205 is formed of a synthetic resin or the like that is heat-shrunk to be fixed on the shaft 1201. The indication member 1205 may preferably be formed from a synthetic resin having a lower friction coefficient, such as tetrafluoraethylene, polyethylene, polyolefine, nylon or the like to allow the indication member 1205 to slide inside the forceps channel 16 more easily. Further, the indication member 1205 rather than a heat-shrink material the indication member 1205 could be a rubber lining, a flexible tube adhered thereto, a coated synthetic resin, or the like.

In this embodiment, when the indication member 1205 of the shaft 1201 passes through the forceps plug 19 in the process of inserting or removing the treatment accessory 1200 from the forceps channel 16, the resistance against the insertion or removal of the shaft 1201 that is received by the forceps plug 19 changes, thereby enabling the operator to detect that the indication member 1205 is passing through the forceps plug 19 due to the sensation transmitted to the operator's hand.

Since the distance B is less than the FC length L, when the treatment accessory 1200 is inserted through the forceps channel 16 of the endoscope 10 and the front end portion of the indication member 1205 reaches the proximal inlet 17 of the forceps channel 16, the treatment device 1202 will be a distance A (A=L−B) from the outlet 18 of the forceps channel 16.

Thus, the operator may visually or tactually detect that the indication member 1205 has passed through forceps plug 19 and stop the insertion of the treatment accessory 1200 into the forceps channel 16 at that point. That is, the treatment accessory 1200 can be stopped before the treatment device 1202 protrudes from the outlet 18 even if inserted quickly. The treatment device 1202 can then be protruded from the outlet 18 slowly and precisely.

Figure 73:
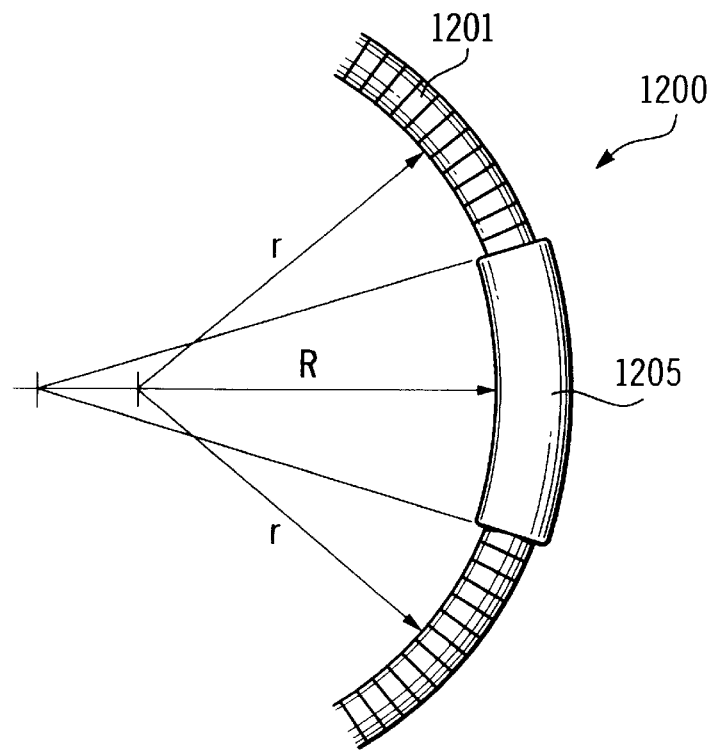
FIG. 73 illustrates the bending of the shaft of FIG. 72.

Further, since the indication member 1205 is formed using a flexible synthetic resin or the like, the indication member 1205 easily bends as shown in FIG. 73. Specifically, it is preferable that, when the shaft 1201 is curved at a radius r, the indication member 1205 curve at a radius R that is only slightly greater than r.

Figure 74:
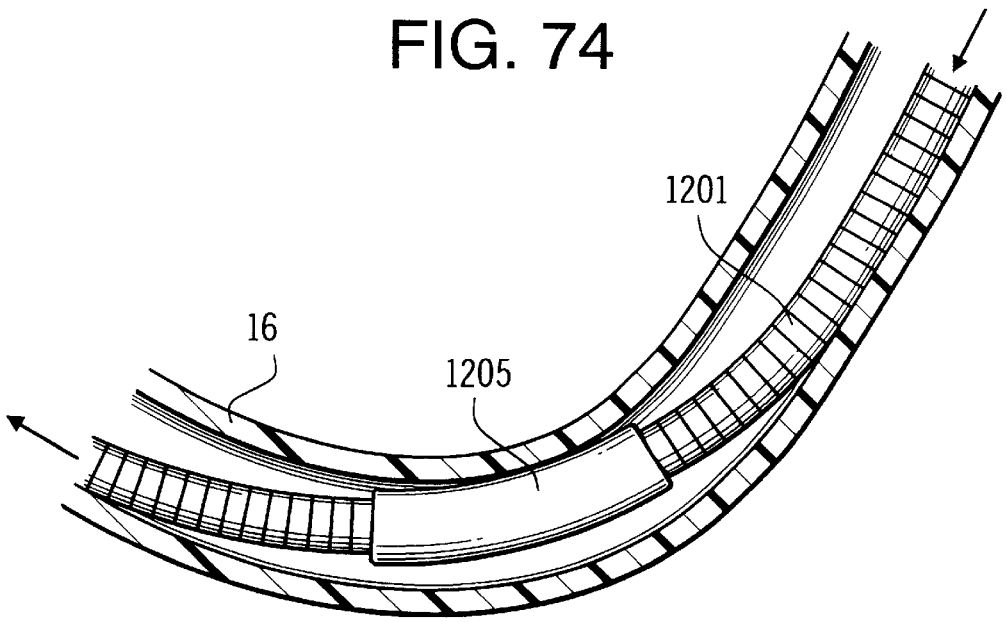
FIG. 74 illustrates the insertion of the shaft of FIG. 72 in a forceps channel.

As shown in FIG. 74, when the shaft 1201 is inserted in the curved forceps channel 16, even if the curvature of the forceps channel 16 is relatively great, the indication member 1205 follows the shape of the forceps channel 16, and therefore can pass through the forceps channel 16 smoothly.

Figure 81:
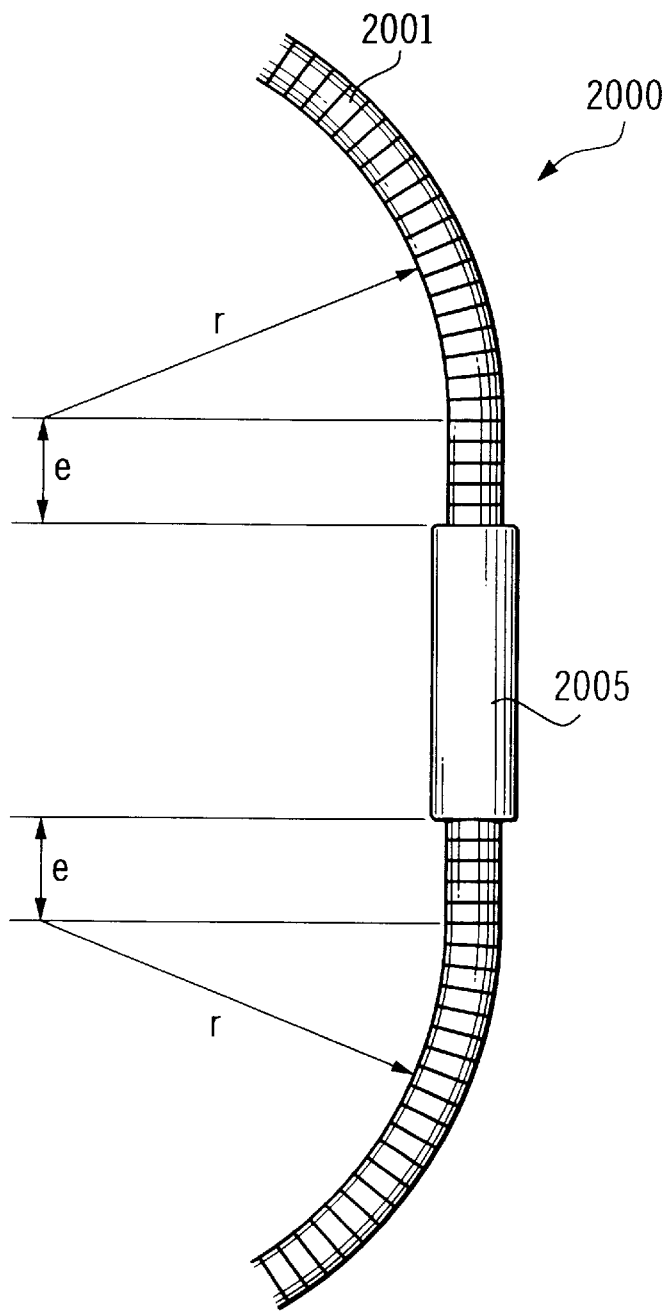
FIG. 81 shows a shaft of a treatment accessory provided with a metal indication member.
Figure 82:
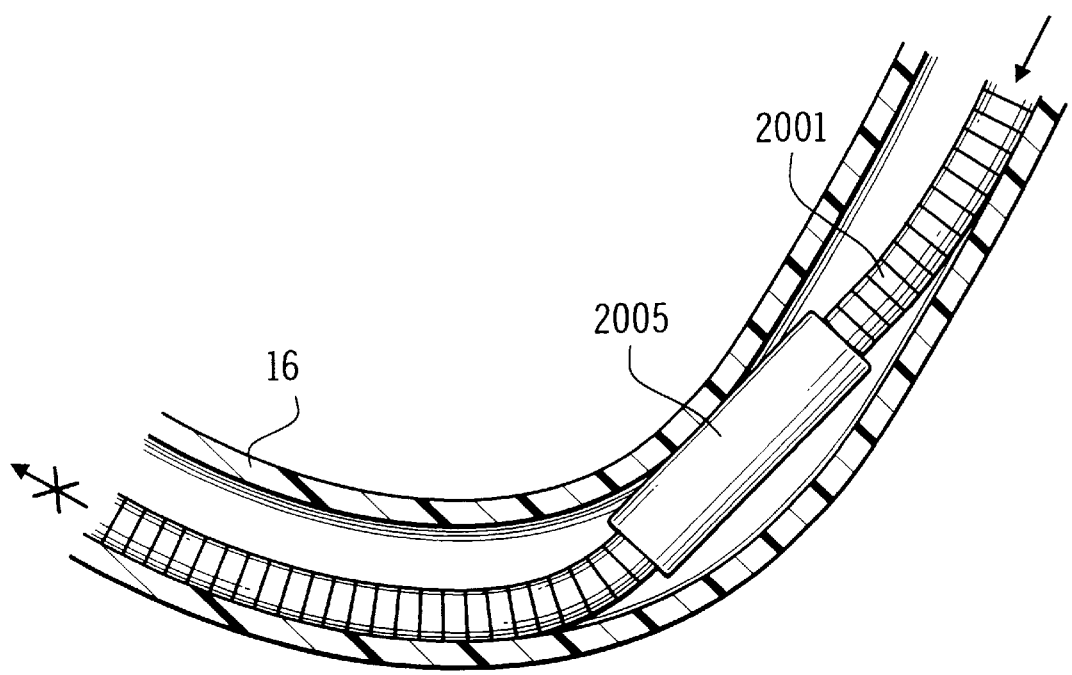
FIG. 82 illustrates the insertion of the shaft of FIG. 81 in a forceps channel.

In this regard, the indication member 1205 may be contrasted with a treatment instrument 2000, as shown in FIG. 81, having a shaft 2001 and an indication member 2005 formed of a relatively inflexible material such as metal. In this case, when the shaft 2001 is curved at a radius r, the indication member 2005 and a portion of the shaft next to the indication member 2005 will not bend appreciably preventing the smooth passage of the accessory through a curved forceps channel 16, as shown in FIG. 82.

As a practical example of the indication member 1205 of the present embodiment, preferably, if the diameter of the shaft is 1.5–2.0 mm, the length K of the indication member 1205 may be 3–12 mm. However, even if the length K is greater, for example, 50 mm, the indication member 1205 may still be used. Further, depending on the intended use of the treatment instrument 1200 or of the endoscope 10, the length K may be shorter.

Figure 75:
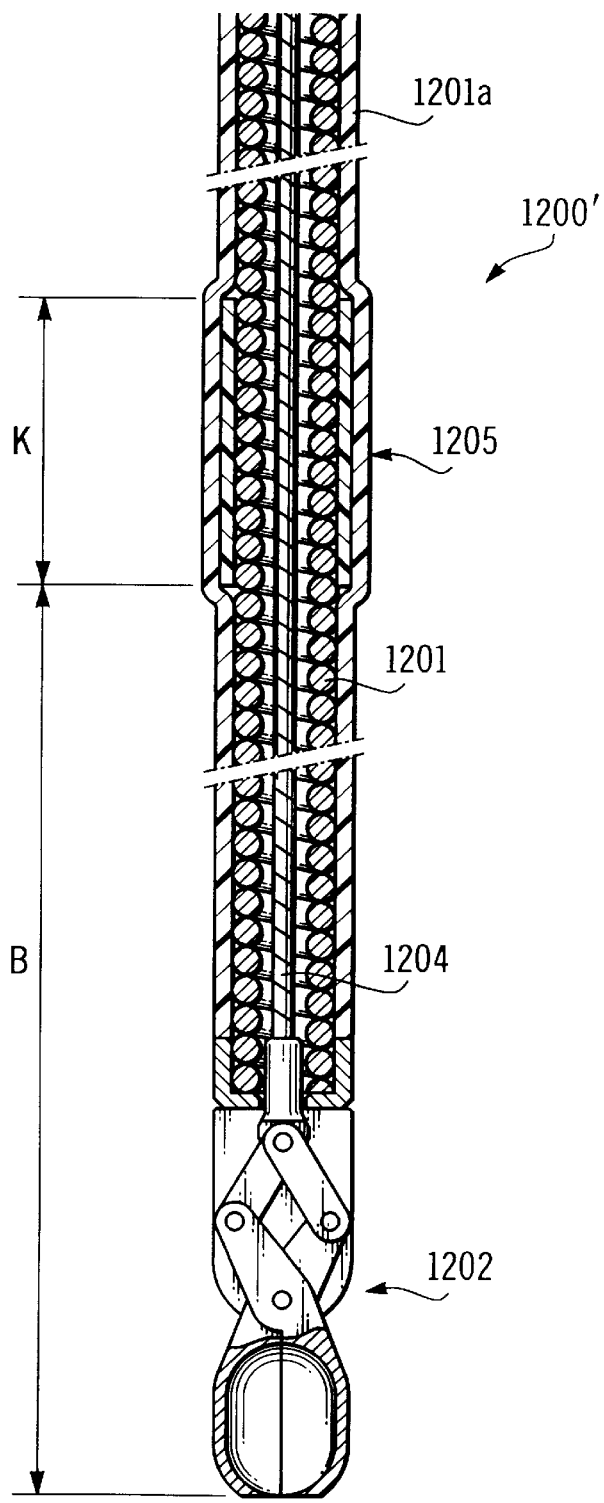
FIG. 75 shows a cross-section of an alternative arrangement of a shaft of the treatment accessory of FIG. 71.

FIG. 75 shows a modified treatment accessory 1200' of the treatment accessory 1200. The modification applies, in particular, to a high-frequency biopsy forceps in which a high-frequency current passes through the treatment instrument via the manipulating wire but may be applied to any treatment accessory.

Figure 72:
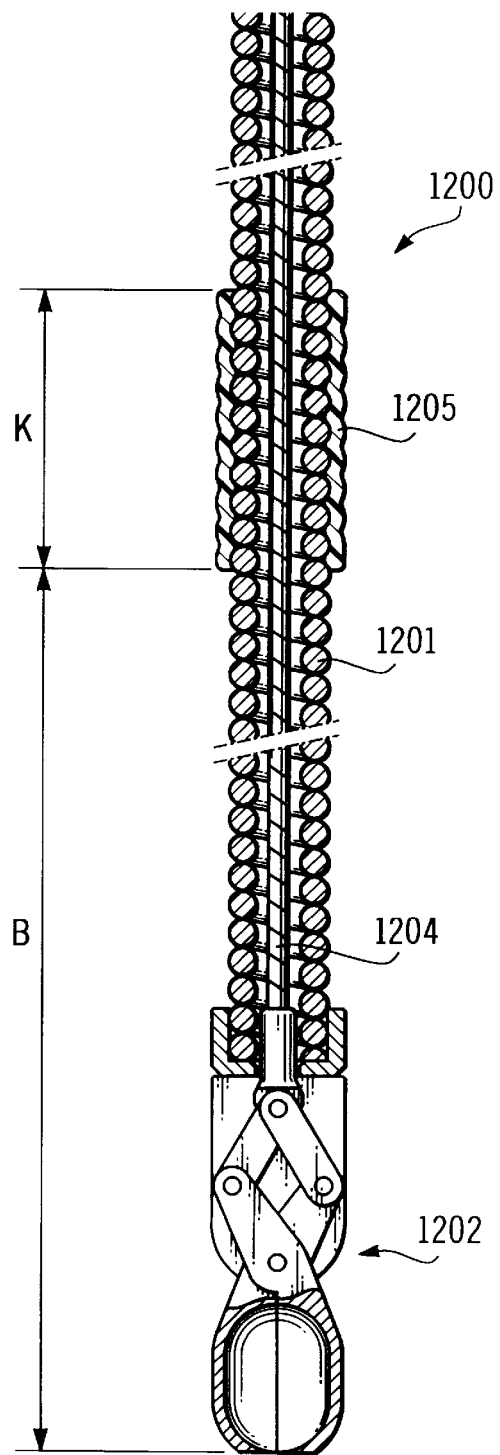
FIG. 72 shows a cross-section of a shaft of the treatment accessory of FIG. 71.

In this case, the surface of the shaft 1201 is covered along its entire length by an electrical insulating tube 1201a. The insulating tube 1201a may be formed by heat-shrinking or other known methods. Note that, in FIG. 75, for simplicity, the surfaces of the insulating tube 1201a and the indication member 1205 are illustrated as smooth, even thought they actually may be uneven, as shown in FIG. 72.

As shown in FIG. 75, the provision of the indication member 1205 causes the outside dimension of the insulating tube 1201a to change such that the operator may still visually or tactually detect the indication member 1205.

Further, the provision of the insulating tube 1201a creates a smoother external surface at the ends of the indication member 1205 such that the treatment accessory 1200' is easier to insert in the forceps channel.

Figure 76:
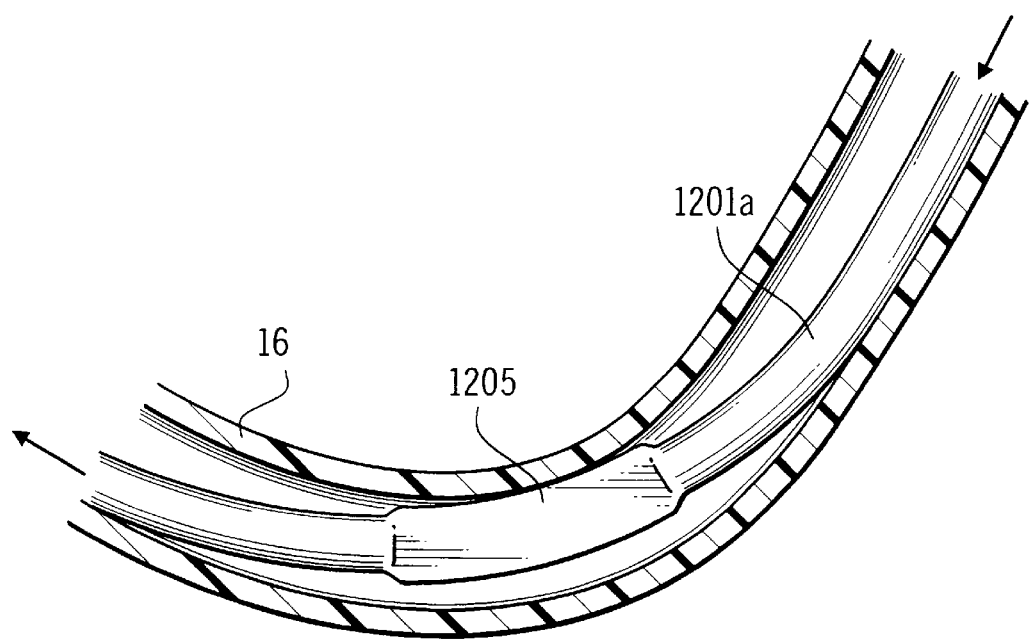
FIG. 76 illustrates the insertion of the shaft of FIG. 75 in a forceps channel.

As shown in FIG. 76, and similar to the description above, the treatment accessory 1200' is inserted easily into even a bent forceps channel 16. Also as described above, in this modification, the length K of the indication member 1205 is preferably 3–12 mm if the diameter of the shaft is 1.5–2.0 mm.

Figure 77:
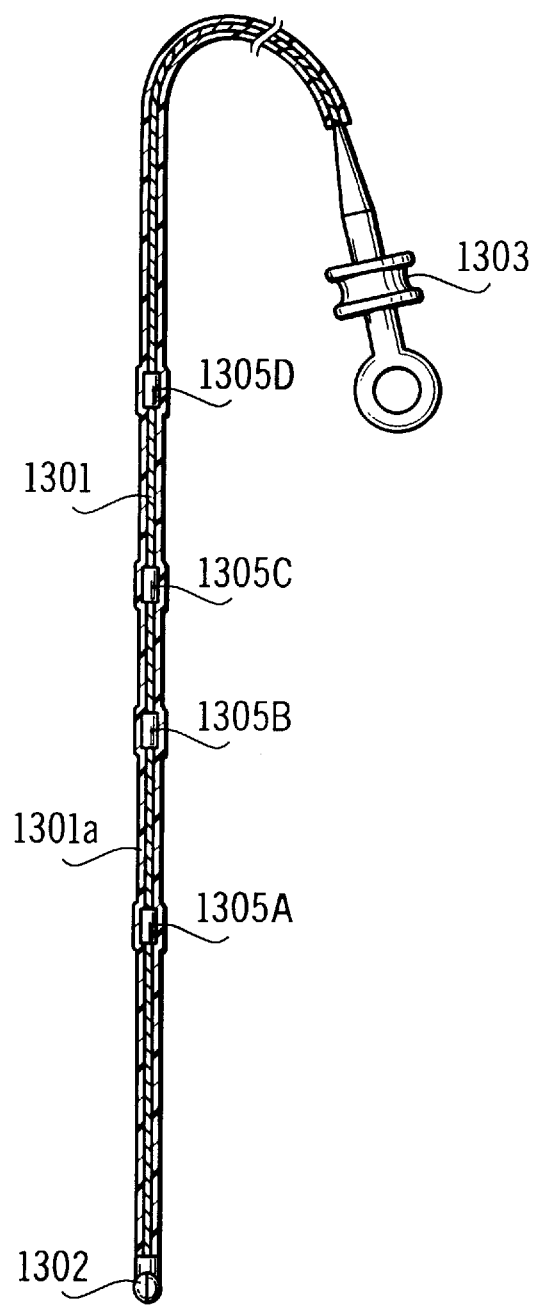
FIG. 77 shows a treatment accessory according to a thirty-fifth embodiment of the invention.

FIG. 77 shows a treatment accessory 1300 according to a thirty-fifth embodiment of the invention. The treatment accessory 1300 is used together with the forceps tap 19, for various endoscopes (first–fourth endoscopes 10, 10A, 10B and 10D) as shown in FIGS. 7–10.

The treatment accessory 1300 includes a flexible shaft 1301 made from a synthetic resin, such as tetrafluoraethylene or the like. At the proximal end of the shaft 1301, an operation unit 1303 is provided, and at the distal end of the shaft 1301, a treatment device 1302 is provided. The treatment device 1302 is remotely operated from the operation unit 1303 by a wire (not shown) inserted inside the shaft 1301. Similar to the modification of the previous embodiment, the shaft 1301 is covered by an insulating tube 1301a.

On the shaft 1301, four indication members 1305A, 1305B, 1305C and 1305D are provided. The indication members 1305A, 1305B, 1305C and 1305D are formed as described above for the previous embodiment. The indication member 1305A corresponds to the first endoscope 10 (see FIG. 7); the indication member 1305B corresponds to the fourth endoscope 10C, the indication member 1305C corresponds to the second endoscope 10A, and the indication member 1305D corresponds to the third endoscope 10B.

Similar to the description for the thirty-fourth embodiment above, when the indication members 1305A, 1305B, 1305C and 1305D pass the forceps tap 19 of the endoscopes 10, 10C, 10A and 10B, respectively, the treatment device 1302 is located, inside the forceps channel, a predetermined length from the distal end of the outlet 18, wherein the predetermined length may be set at, for example, between 1 to 10 cm.

With use of the treatment accessory 1300, a single treatment accessory can be used for various types of endoscopes, or endoscopes having various lengths of forceps channels, and in any case, the operator can stop inserting the treatment accessory before the treatment device extends from the distal end of the forceps channel.

Figure 78:
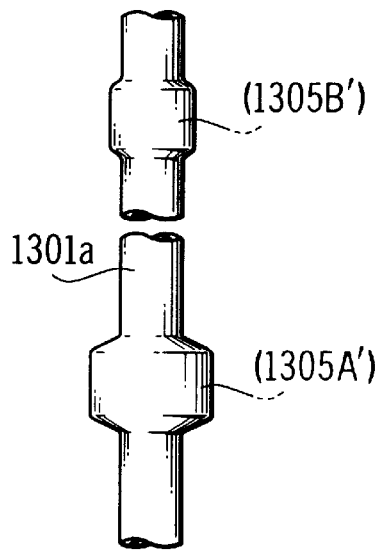
FIGS. 78 to 80 illustrate alternative arrangements of a shaft of the treatment accessory of FIG. 77.
Figure 79:
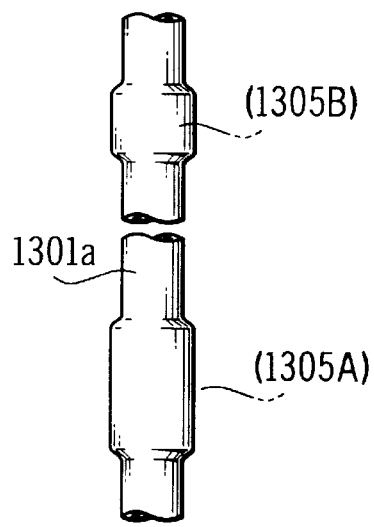

The indication members 1305A–1305D could each be formed to have the same shape. Alternatively, as shown in FIGS. 78 and 79 using the indication members 1305A and 1305B as examples, the indication members 1305A–1305D could each be formed to have a different shape or the like. For example, as shown in FIG. 78, an indication member 1305B' may have a smaller outside diameter than an indication member 1305A', or as show in FIG. 79, the indication member 1305B' may have a smaller length along the axis of the insulation tube 1301a than the indication member 1305A'.

Figure 80:
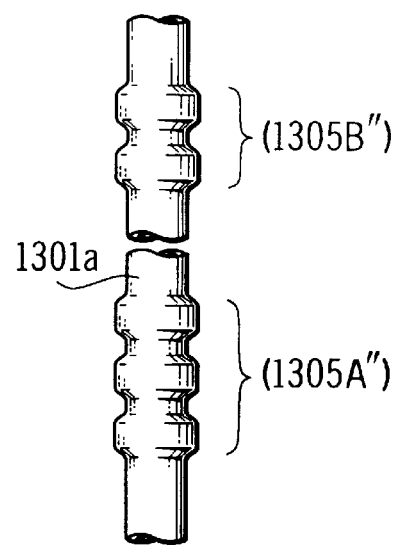

Further alternatively, as shown in FIG. 80, again using the indication members 1305A and 1305B as examples, the indication members 1305A–1305D could each be formed to have a series of different shapes or the like. For example, as shown in FIG. 80, an indication member 1305B" may be formed to have two portions that have a larger diameter than the shaft 1301 and the indication member 1305A" may be formed to have three portions that have a larger diameter than the shaft 1301.

Of course, other alternatives are also possible, as long as the operator may detect, visually and tactually, that a particular indication member has entered or been removed from the forceps channel 16.

Although the structure and operation of treatment accessories have been described herein with respect to the preferred embodiments, many modifications and changes can be made without departing from the spirit and scope of the invention.

The present disclosure relates to subject matters contained in Japanese Patent Applications No. HEI 08-234945, filed on Sep. 5, 1996, No. HEI 08-234946, filed on Sep. 5, 1996, No. HEI 08-239083, filed on Sep. 10, 1996, No. HEI 09-54437, filed on Mar. 10, 1997, No. HEI 09-54438, filed on Mar. 10, 1997, No. HEI 09-41720, filed on Feb. 26, 1997, No. HEI 09-66398, filed on Mar. 19, 1997, No. HEI 09-71064, filed on Mar. 25, 1997, and No. HEI 9-71065, filed on Mar. 25, 1997, which are expressly incorporated herein by reference in their entirety.

What is claimed is:

1. A treatment accessory in combination with an endoscope, said endoscope including a forceps channel having an inlet and an outlet separated by a predetermined distance, said treatment accessory being inserted in or removed from said forceps channel of said endoscope through an inlet of said forceps channel, said treatment accessory comprising:

a treatment device; and a flexible shaft, said treatment device being provided at a first end of said flexible shaft, said flexible shaft being provided with a marking at a predetermined portion thereof, said predetermined portion being located such that the distance between said marking and the distal end of said treatment device is less than the predetermined distance between said inlet and said outlet of said forceps channel by 1 to 20 cm, said treatment device being located at a predetermined position inside said forceps channel when said marking is located at said inlet of said forceps channel.

2. The treatment accessory according to claim 1, wherein when said treatment device is located at a position within a predetermined position range inside said forceps channel, said marking is located at said inlet.

3. The treatment accessory according to claim 2, wherein said marking has a predetermined length along an axis of said flexible shaft, and wherein when any portion of said marking is located at said inlet, said treatment device is located inside said forceps channel.

4. The treatment accessory according to claim 2, wherein said marking has a predetermined length along an axis of said flexible shaft, and wherein said predetermined portion is an end, along said axis of said flexible shaft, of said marking having said predetermined length.

5. The treatment accessory according to claim 2, wherein said marking has a predetermined length along an axis of said flexible shaft, and wherein when one end of said marking is located at said inlet, said treatment device is located inside said forceps channel, and wherein when the other end of said marking is located at said inlet, said treatment device is extended from said outlet of said forceps channel.

6. The treatment accessory according to claim 2, wherein at least one of a color, texture, thickness, and shape of said marking is different from the other portion of said flexible shaft.

7. The treatment accessory according to claim 2, wherein said flexible shaft is provided with at least one other marking, said at least one other marking corresponding to at least one other forceps channel having a length different from said forceps channel.

8. The treatment accessory according to claim 2, wherein said marking comprises a ring-like member slidably fitted on said flexible shaft, a predetermined frictional force being generated between said ring-like member and said flexible shaft when said ring-like member is slid on said flexible shaft.

9. The treatment accessory according to claim 8, wherein at least a part of an outer diameter of said ring-like member is greater than an inner diameter of said forceps channel.

10. The treatment accessory according to claim 8, wherein an outer diameter of said ring-like member is smaller than an inner diameter of said forceps channel.

11. The treatment accessory according to claim 8, wherein said flexible shaft is provided with at least one position indicating area, said at least one position indicating area being formed at a portion where said ring-like member is to be initially located.

12. The treatment accessory according to claim 11, wherein said position indicating area is different from the other portion of said flexible shaft by at least one of a color, thickness, texture, and a shape.

13. The treatment accessory according to claim 12, wherein said flexible shaft is provided with a plurality of position indicating areas corresponding to a plurality of forceps channels having different lengths.

14. The treatment accessory according to claim 13, wherein said plurality of position indicating areas are different from each other by at least one of a color, texture, thickness, and a shape.

15. The treatment accessory according to claim 2, wherein said flexible shaft comprises a coil shaft formed from a wound coil, and wherein said marking comprises a tube member covering said coil shaft, said tube member being made from resin.

16. A treatment accessory in combination with an endoscope, said endoscope including a forceps channel having an inlet and an outlet separated by a predetermined distance, said treatment accessory being inserted in said forceps channel of said endoscope, said treatment accessory having a shaft and a treatment device provided at a distal end of said shaft, said treatment device being extended from a distal end of said forceps channel when treatment is performed, said shaft being provided with a marking at a position such that the distance between said marking and the distal end of said treatment device is less than the predetermined distance between said inlet and said outlet of said forceps channel by 1 to 20 cm, said marking being located at said inlet of said forceps channel when said treatment device is located at a position close to said distal end of said forceps channel and inside said forceps channel.

17. The treatment accessory according to claim 16, wherein said shaft is provided with another marking which is located at said inlet of said forceps channel when said treatment device is located at said distal end of said forceps channel.

18. The treatment accessory according to claim 16, wherein said marking comprises a visually recognizable portion.

19. The treatment accessory according to claim 16, wherein said marking comprises a portion recognizable by a sense of touch.

20. A treatment accessory in combination with endoscopes having forceps channels of different lengths, said treatment accessory being inserted in a selected one of said forceps channels of said endoscopes, said treatment accessory having a shaft, and a treatment device provided at a distal end of said shaft, said treatment device being extended from a distal end of each of said forceps channels when treatment is performed, said shaft being provided with a plurality of markings, each of said plurality of markings being located at an inlet of a respective one of said forceps channels when said treatment device is located at a position close to said distal end of a respective one of said forceps channels and inside said forceps channel.

21. The treatment accessory according to claim 20, wherein said plurality of markings comprise visually recognizable portions.

22. The treatment accessory according to claim 20, wherein said plurality of markings have different characteristics from each other.

23. A treatment accessory in combination with an endoscope, said treatment accessory having a shaft which is to be inserted in and removed from a forceps channel of said endoscope, a treatment device being provided at a distal end of said shaft, said shaft being provided with a marking, said marking appearing from an end of said forceps channel when said shaft is being withdrawn from said forceps channel and when a length of said treatment accessory remaining in said forceps channel is within a range of 10 cm through 30 cm.

24. The treatment accessory according to claim 23, wherein said marking is located inside said forceps channel when said treatment device is extended from said forceps channel and used for treating.

25. The treatment accessory according to claim 23, wherein said marking has a color different from a color of the other portion of said shaft.

26. The treatment accessory according to claim 23, wherein said marking has a hardness different from a hardness of the other portion of said shaft.

27. The treatment accessory according to claim 23, wherein said marking comprises a portion which has an outer diameter different from that of the other portion of said shaft.

28. The treatment accessory according to claim 1, wherein said shaft is provided with a slidable member fitted thereon, said slidable member, when contacting said inlet of said forceps channel, applies a predetermined resistance to said shaft when said shaft is being inserted in said forceps channel.

29. The treatment accessory according to claim 28, wherein said slidable member is slidable on said shaft along an axial direction of said shaft, a predetermined friction existing between said slidable member and said shaft, said predetermined friction causing said predetermined resistance to said shaft.

30. The treatment accessory according to claim 28, wherein said slidable member is formed from elastic material, an inner diameter of said slidable member being smaller than an outer diameter of said shaft.

31. The treatment accessory according to claim 28, wherein said shaft is provided with a marking which indicates a position where said slidable member is to be initially located.

32. The treatment accessory according to claim 28, wherein said slidable member is formed to have a cylindrical shape.

33. A treatment accessory in combination with an endoscope, said treatment accessory being provided with a shaft to be inserted in or withdrawn from a forceps channel of said endoscope, said shaft being provided with a slidable member fitted thereon, said slidable member, when contacting an inlet of said forceps channel, applies a predetermined resistance to said shaft when said shaft is being inserted in said forceps channel, wherein said slidable member is formed to have a cylindrical shape and wherein said slidable member is further provided with a flange portion which has a greater diameter than the inner diameter of the inlet of the forceps channel.

34. A treatment accessory in combination with an endoscope, said treatment accessory being provided with a shaft to be inserted in or withdrawn from a forceps channel of said endoscope, said shaft being provided with a slidable member fitted thereon, said slidable member, when contacting an inlet of said forceps channel, applies a predetermined resistance to said shaft when said shaft is being inserted in said forceps channel, wherein said slidable member is formed to have substantially a cylindrical shape, a diameter of an end portion of said cylindrical shape being smaller than a diameter of a central portion of said cylindrical shape.

35. The treatment accessory according to claim 23, wherein said shaft is provided with a fitted member fitted thereon at a predetermined portion, said fitted member causing a predetermined resistance when said fitted member passes through a slit of a forceps tap.

36. The treatment device according to claim 35, further comprising at least one other fitted member.

37. The treatment device according to claim 36, wherein said fitted member and said at least one other fitted member are visibly distinguishable.

* * * * *